US012590138B2

(12) United States Patent
Wu et al.

(10) Patent No.: US 12,590,138 B2
(45) Date of Patent: Mar. 31, 2026

(54) TREATMENTS ADMINISTERING CHIMERIC IgG Fc RECEPTOR COMPRISING AN EXTRACELLULAR DOMAIN OF CD64

(71) Applicant: Regents of the University of Minnesota, Minneapolis, MN (US)

(72) Inventors: Jianming Wu, Plymouth, MN (US); Bruce Kenneth Walcheck, Lino Lakes, MN (US); Robert Harrison Hullsiek, Minneapolis, MN (US); Yungfang Li, Minneapolis, MN (US); Hemant Kumar Mishra, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 107 days.

(21) Appl. No.: 18/474,781

(22) Filed: Sep. 26, 2023

(65) Prior Publication Data

US 2024/0124550 A1      Apr. 18, 2024

Related U.S. Application Data

(62) Division of application No. 16/758,142, filed as application No. PCT/US2018/057689 on Oct. 26, 2018, now abandoned.

(60) Provisional application No. 62/577,425, filed on Oct. 26, 2017.

(51) Int. Cl.
| | |
|---|---|
| *A61K 40/11* | (2025.01) |
| *A61K 40/15* | (2025.01) |
| *A61K 40/31* | (2025.01) |
| *A61K 40/33* | (2025.01) |
| *A61K 40/42* | (2025.01) |
| *C07K 14/735* | (2006.01) |
| *C07K 16/30* | (2006.01) |
| *C12N 5/0783* | (2010.01) |

(52) U.S. Cl.
CPC ........ *C07K 14/70535* (2013.01); *A61K 40/11* (2025.01); *A61K 40/15* (2025.01); *A61K 40/31* (2025.01); *A61K 40/33* (2025.01); *A61K 40/42* (2025.01); *A61K 40/421* (2025.01); *A61K 40/4224* (2025.01); *C07K 16/30* (2013.01); *C12N 5/0636* (2013.01); *C12N 5/0646* (2013.01); *A61K 2239/17* (2023.05); *A61K 2239/21* (2023.05); *C07K 2317/24* (2013.01); *C07K 2319/00* (2013.01); *C07K 2319/03* (2013.01); *C07K 2319/74* (2013.01)

(58) Field of Classification Search
CPC .. A61K 38/177; A61K 38/1774; A61K 40/11; A61K 40/15; A61K 40/31; A61K 40/33; A61K 40/42; A61K 40/4224; A61K 2239/15; A61K 2239/21; A61K 2239/22; C07K 14/70503; C07K 14/70535; C07K 19/00; C07K 2319/00; C07K 2319/50; C07K 2319/02; C07K 2319/03; C07K 2319/74; C07K 16/30; C12N 5/0637; C12N 5/0646

See application file for complete search history.

(56) References Cited

U.S. PATENT DOCUMENTS

| | | | |
|---|---|---|---|
| 7,618,817 | B2 | 11/2009 | Cambell |
| 10,640,570 | B2 | 5/2020 | Kaufman et al. |
| 2004/0101519 | A1 | 5/2004 | June et al. |
| 2006/0034810 | A1 | 2/2006 | Riley et al. |
| 2006/0292156 | A1 | 12/2006 | Campbell |
| 2008/0003225 | A1 | 1/2008 | Vie et al. |
| 2009/0196870 | A1 | 8/2009 | Ledbetter et al. |
| 2012/0070819 | A1 | 3/2012 | Hengel et al. |
| 2014/0322183 | A1 | 10/2014 | Milone et al. |
| 2015/0139943 | A1 | 5/2015 | Campana et al. |
| 2016/0009813 | A1 | 1/2016 | Themeli et al. |
| 2016/0355566 | A1 | 12/2016 | Li et al. |
| 2017/0081411 | A1 | 3/2017 | Engels et al. |
| 2017/0174743 | A1 | 6/2017 | Walcheck et al. |
| 2018/0002438 | A1 | 1/2018 | Kaufman et al. |
| 2018/0085399 | A1 | 3/2018 | Ahmed et al. |
| 2020/0017570 | A1 | 1/2020 | Walcheck et al. |

(Continued)

FOREIGN PATENT DOCUMENTS

| | | |
|---|---|---|
| CN | 104136458 | 11/2014 |
| CN | 105601746 | 5/2016 |
| CN | 106459918 | 2/2017 |

(Continued)

OTHER PUBLICATIONS

Shim et al. One target, different effects: a comparison of distinct therapeutic antibodies against the same targets. Exp Mol Med 43(10): 539-549, 2011.*

(Continued)

*Primary Examiner* — Bridget E Bunner
(74) *Attorney, Agent, or Firm* — Fish & Richardson P.C.

(57) ABSTRACT

A recombinant immune cell expresses a heterologous IgG Fc receptor. In some embodiments, the heterologous IgG Fc receptor can be a chimeric IgG Fc receptor. Generally, the chimeric IgG Fc receptor includes an extracellular domain, a transmembrane domain, and an intracellular domain. The extracellular domain generally includes a sufficient portion of CD64 to bind to an IgG Fc region. The intracellular domain of the chimeric IgG Fc receptor includes a sufficient portion of an Fc receptor allowing immunoreceptor tyrosine-based activation motif (ITAM) to initiate cell signaling when an IgG Fc region binds to the extracellular domain.

9 Claims, 20 Drawing Sheets

Specification includes a Sequence Listing.

(56) References Cited

U.S. PATENT DOCUMENTS

2020/0283501 A1     9/2020   Wu et al.

FOREIGN PATENT DOCUMENTS

| CN | 106715467 | 5/2017 |
|---|---|---|
| EP | 1734119 | 12/2006 |
| JP | H11511649 | 10/1999 |
| JP | 2007528194 | 3/2007 |
| JP | 2008005722 | 1/2008 |
| JP | 2017503510 | 2/2017 |
| WO | WO 1996034953 | 11/1996 |
| WO | WO 2005017148 | 2/2005 |
| WO | WO 2005044996 | 5/2005 |
| WO | WO 2006023148 | 3/2006 |
| WO | WO 2010040091 | 4/2010 |
| WO | WO 2010105817 | 9/2010 |
| WO | WO 2013126729 | 8/2013 |
| WO | WO 2014145252 | 9/2014 |
| WO | WO 2014153270 | 9/2014 |
| WO | WO 2014179759 | 11/2014 |
| WO | WO 2015148926 | 10/2015 |
| WO | WO 2015168613 | 11/2015 |
| WO | WO 2015179833 | 11/2015 |
| WO | WO 2016040441 | 3/2016 |
| WO | WO 2016123333 | 8/2016 |

OTHER PUBLICATIONS

Abate-Daga et al., "CAR models: next-generation CAR modifications for enhanced T-cell function," Mol. Ther.—Oncolytics, 2016, 3:16014, 7 pages.

Ahmed et al., "Human Epidermal Growth Factor Receptor 2 (HER2)-Specific Chimeric Antigen Receptor-Modified T Cells for the Immunotherapy of HER2-Positive Sarcoma," J. Clin. Oncol., May 20, 2015, 33(15):1688-1696.

Aker et al., "Extended core sequences from the cHS4 insulator are necessary for protecting retroviral vectors from silencing position effects," Hum Gene Ther., Apr. 2007, 18(4):333-343.

Alderson et al., "Clinical cancer therapy by NK cells via antibody-dependent cellmediated cytotoxicity," J Biomed Biotechnol., 2011, 2011:379123, 7 pages.

Altvater et al., "2B4 (CD244) signaling by recombinant antigen-specific chimeric receptors costimulates natural killer cell activation to leukemia and neuroblastoma cell," Clin. Canc Res., Aug. 1, 2009, 15(15):4857-4866.

Altvater et al., "2B4 (CD244) signaling via chimeric receptors costimulates tumor-antigen specific proliferation and in vitro expansion of human T cells," Cancer Immunol Immunother., 2009, 58(12):1991-2001.

Anderson et al., "Fcγ receptor type III (CD16) is included in the ζ NK receptor complex expressed by human natural killer cells," Proc. Natl. Acad. Sci. USA, Mar. 1990, 87(6):2274-2278.

Angelos et al., "Pluripotent stem cell applications for regenerative medicine," Curr. Opin. Organ Transplant., Dec. 2015, 20(6):663-670.

Argument and Amendment in Response to the First CN Office Action in Chinese Appln. No. 201880084483.4, dated Mar. 16, 2023, 18 pages (with English translation).

Argument and Amendment in Response to the First JP Office Action in Japanese Appln. No. 2020-543244, dated Oct. 5, 2023, 12 pages (with English translation).

Argument and Amendment in Response to the First JP Office Action in Japanese Appln. No. 2022-035778, dated Aug. 14, 2023, 11 pages (with English translation).

Argument and Amendment in Response to the Second CN Office Action in Chinese Appln. No. 201880084483.4, dated Oct. 8, 2023, 22 pages (with English translation).

Argument and Amendment in Response to the Second JP Office Action in Japanese Appln. No. 2022-035778, dated Mar. 1, 2024, 10 pages (with English translation).

Bachanova et al., "Clearance of acute myeloid leukemia by haploidentical natural killer cells is improved using IL-2 diphtheria toxin fusion protein," Blood., 2014, 123(25):3855-3863.

Bachanova., "NK Cells in Therapy of Cancer," Crit Rev Oncog., 2014, 19(1-2):133-141.

Baghbaderani et al., "cGMP-manufactured human induced pluripotent stem cells are available for pre-clinical and clinical applications," Stem Cell Reports, Oct. 2015, 5(4):647-659.

Baghbaderani et al., "Manufacturing human induced-pluripotent stem cells for clinical application," BioProcess International, Oct. 2015, 13(9)s, 8 pages.

Barrett et al., "Chimeric Antigen Receptor Therapy for Cancer," Annual Rev Med., Jan. 2014, 65:333-347.

Battella et al., "Natural killer (NK) cells and anti-tumor therapeutic mAb: unexplored interactions," J. Leukoc. Biol., Jan. 2016, 99(1):87-96.

Beatty et al., "Mesothelin-Specific Chimeric Antigen Receptor mRNA-Engineered T Cells Induce Antitumor Activity in Solid Malignancies," Canc Immunol Res., Feb. 2014, 2(2):112-120.

Bergeron et al., "Comparative functional characterization of canine IgG subclasses," Vet. Immunol. Immunopathology, Jan. 15, 2014, 157:31-41.

Bhat et al., "Serial killing of tumor cells by human natural killer cells—enhancement by therapeutic antibodies," PLoS One, Mar. 2007, 2(3):e326.

Bhattacharya et al. Impact of genetic variation on three dimensional structure and function of proteins. PLoS ONE 12(3): e0171355, 2017.

Binyamin et al., "Blocking NK cell inhibitory self-recognition promotes antibody-dependent cellular cytotoxicity in a model of anti-lymphoma therapy," J Immunol., May 1, 2008, 180(9):6392-6401.

Bollino et al., "Chimeric antigen receptor-engineered natural killer and natural killer T cells for cancer immunotherapy," Transl Res., Sep. 2017, 187:32-43.

Bork, P. Go hunting in sequence databases but watch out for the traps. Trends in Genetics 12(10): 425-427, 1996.

Bork, P. Powers and pitfalls in sequence analysis: the 70% hurdle. Genome Res 10: 398-400, 2000.

Brenner. S.E. Errors in genome annotation. Trends in Genetics 15:132-133, 1999.

Bruhns et al., "Specificity and affinity of human Fcγ receptors and their polymorphic variants for human IgG subclasses," Blood, Apr. 2009, 113(16):3716-3725.

Bryant et al., "Calculation of lytic units for the expression of cell-mediated cytotoxicity," J Immunol Methods., 1992, 146(1):91-103.

Bryceson et al., "Activation, coactivation, and costimulation of resting human natural killer cells," Immunol Rev., Dec. 2006, 214(1):73-91.

Bryceson et al., "Molecular mechanisms of natural killer cell activation," J Innate Immun., 2011, 3:216-226.

Bryceson et al., "Synergy among receptors on resting NK cells for the activation of natural cytotoxicity and cytokine secretion," Blood., Jan. 2006, 107(1):159-166.

Burgess-Beusse et al., "The insulation of genes from external enhancers and silencing chromatin," PNAS., Dec. 10, 2002, 99(suppl 4):16433-16437.

Caescu et al., "Active-site determinants of substrate recognition by the metalloproteinases TACE and ADAMI O," Biochem J., Oct. 2009, 424(1):79-88.

Caligiuri., "Human natural killer cells," Blood., Aug. 1, 2008, 112(3):461-469.

Carlsten et al., "Genetic manipulation of NK cells for cancer immunotherapy: techniques and clinical implications," Front Immunol., Jun. 10, 2015, 6(Article 266), 9 pages.

Carotta, "Targeting NK Cells for Anticancer Immunotherapy: Clinical and Preclinical Approaches," Front. Immunol., Apr. 2016, 7:152.

Chae et al. Qualitatively differential regulation of T cell activation and apoptosis by T cell receptor zeta chain ITAMs and their tyrosine residues. Int Immunol 16(9): 1225-1236, 2004.

(56) References Cited

OTHER PUBLICATIONS

Chang et al., "A Chimeric Receptor with NKG2D Specificity Enhances Natural Killer Cell Activation and Killing of Tumor Cells," Cancer Res., Mar. 15, 2013, 73(6):1777-1786.

Chen et al., "Gene-modified NK-92MI cells expressing a chimeric CD16-BB-ζ or CD64-BB-ζ receptor exhibit enhanced cancer-killing ability in combination with therapeutic antibody," Oncotarget, Mar. 15, 2017, 8(23):37128-37139.

Cheng et al., "NK cell-based immunotherapy for malignant diseases," Cell Mol. Immunol., 2013, 10:230-252.

Childs et al., "Therapeutic approaches to enhance natural killer cell cytotoxicity against cancer: the force awakens," Nat. Rev. Drug Disc., 2015, 14:487-498.

Choi et al., "Hematopoietic and endothelial differentiation of human induced pluripotent stem cells," Stem Cells, 2009, 27:559-567.

Chowdhury et al., "Isolation of a high-affinity stable single-chain Fv specific for mesothelin from DNA-immunized mice by phage display and construction of a recombinant immunotoxin with anti-tumor activity," PNAS, Jan. 20, 1998, 95(2):669-674.

CN Decision of Rejection in Chinese Appln. No. 201880084483.4, dated Nov. 10, 2023, 17 pages (with English translation).

CN Office Action in Chinese Appln. No. 201880084483.4, dated Jul. 14, 2023, 17 pages (with English translation).

CN Office Action in Chinese Appln. No. 201880084483.4, dated Nov. 2, 2022, 11 pages (with English translation).

Coenon et al. From CD16a biology to antibody-dependent cell-mediated cytotoxicity improvement. Front Immunol 13: 913215, 2022.

Cox et al., "Tumor-associated and immunochemotherapy-dependent long-term alterations of the peripheral blood NK cell compartment in DLBCL patients," Oncoimmunology, Jan. 2015, 4(3):e990773.

Coxon et al., "Fcγ RIII mediates neutrophil recruitment to immune complexes, a mechanism for neutrophil accumulation in immune-mediated inflammation," Immunity, Jun. 2001, 14(6):693-704.

Deguine et al., "Cutting edge: tumor-targeting antibodies enhance NKG2D-mediated NK cell cytotoxicity by stabilizing NK cell-tumor cell interactions," J Immunol., Dec. 2012, 189(11):5493-5497.

Denman et al., "Membrane-Bound IL-21 Promotes Sustained Ex Vivo Proliferation of Human Natural Killer Cells," Plos One, Jan. 2012, 7(1):e30264, 13 pages.

Dhar et al., "NKG2D and its ligands in cancer," Curr. Opinion Immunol., Apr. 2018, 51:55-61.

Dietrich et al., "Identification of the kinesin KifC3 as a new player for positioning of peroxisomes and other organelles in mammalian cells," Biochimica et Biophysica Acta (BBA)-Molecular Cell Research, Dec. 2013, 1833(12):3013-24.

Doedens et al., "Stimulation-induced down-regulation of tumor necrosis factor-alpha converting enzyme," J Biol Chem., 2000, 275:14598-14607.

Doerks et al. Protein annotation: detective work for function prediction. Trends in Genetics 14:248-250, 1998.

Dolstra et al., "Successful Transfer of Umbilical Cord Blood CD34+ Hematopoietic Stem and Progenitor-derived NK Cells in Older Acute Myeloid Leukemia Patients," Clin Cancer Res., Aug. 2017, 23(15):4107-4118.

Dong et al., "Fcγ receptor IIIa single-nucleotide polymorphisms and haplotypes affect human IgG binding and are associated with lupus nephritis in African Americans," Arthritis Rheumatol., May 2014, 66(5):1291-1299.

Dotti et al., "Design and development of therapies using chimeric antigen receptor- expressing T cells," Immunol. Review, Jan. 2014, 257(1):107-126.

Eagle et al., "Promiscuity and the single receptor: NKG2D," Nat Rev Immunol., 2007, 7:737-744.

Eguizabal et al., "Natural killer cells for cancer immunotherapy: pluripotent stem cells-derived NK cells as an immunotherapeutic perspective," Front Immunol., 2014, 5:439, 10 pages.

Ellsworth et al. Generation of a high-affinity Fcgamma receptor by Ig-domain swapping between human CD64A and CD16A. Protein Eng Design Selection 23(4): 299-309, 2010.

Feehan et al., "Shedding of the lymphocyte L-selectin adhesion molecule is inhibited by a hydroxamic acid-based protease inhibitor. Identification with an L-selectinalkaline phosphatase reporter," J Biol Chem., 1996, 271:7019-7024.

Fenton et al. Rheostat positions: a new classification of protein positions relevant to pharmacogenomics. Medicinal Chem Res 29:1133-1146,2020.

Fesnak et al., "Engineered T cells: the promise and challenges of cancer immunotherapy," Nat Rev Canc., 2016, 16:566-581.

Figueroa et al., "Chimeric Antigen Receptor Engineering: A Right Step in the Evolution of Adoptive Cellular Immunotherapy," Int Rev Immunol., 2015, 34(2):154-187.

Galon et al., "Identification of the cleavage site involved in production of plasma soluble Fcγ receptor type III (CD16)," Eur J Immunol., 1998, 28:2101-2107.

Garrity et al., "The activating NKG2D receptor assembles in the membrane with two signaling dimers into a hexameric structure," PNAS, May 24, 2005, 102(21):7641-7646.

Geller et al., "A phase II study of allogeneic natural killer cell therapy to treat patients with recurrent ovarian and breast cancer," Cytotherapy, Jan. 2011, 13(1):98-107.

Geller et al., "Intraperitoneal delivery of human natural killer cells for treatment of ovarian cancer in a mouse xenograft model," Cytotherapy, 2013, 15:1297-1306.

Geller et al., "Use of allogeneic NK cells for cancer immunotherapy," Immuno Ther., Decmber 2011, 3(12):1445-1459.

Giudice et al., "Genetic Modification of Human Embryonic Stem Cells for Derivation of Target Cells," Cell Stem Cell, May 8, 2008, 2(5):422-433.

Gong et al., "Characterization of a human cell line (NK-92) with phenotypical and functional characteristics of activated natural killer cells," Leukemia., 1994, 8:652-658.

Granzin et al., "Fully automated expansion and activation of clinical-grade natural killer cells for adoptive immunotherapy," Cytotherapy, May 2015, 17(5):621-632.

Grupp et al., "Chimeric Antigen Receptor-Modified T Cells for Acute Lymphoid Leukemia," N. Engl. J. Med., Apr. 18, 2013, 368:1509-1518.

Guillerey et al., "Targeting natural killer cells in cancer immunotherapy," Nat Immunol., 2016, 17:1025-1036.

Guo et al. Protein tolerance to random amino acid change. Proc Natl Acad Sci USA 101(25): 9205-9210, 2004.

Handgretinger et al., "Exploitation of natural killer cells for the treatment of acute leukemia," Blood, Jun. 30, 2016, 127:3341-3349.

Harrison et al., "High affinity IgG binding by FcγRI (CD64) is modulated by two distinct IgSF domains and the transmembrane domain of the receptor," Protein Eng., Mar. 1998, 11(3):225-232.

Harrison et al., "Involvement of a metalloprotease in spontaneous and phorbol ester-induced release of natural killer cell-associated Fcγ RIii (CD 16-11)," J Immunol., Nov. 15, 1991, 147(10):3459-3465.

Hassan et al., "Mesothelin targeted cancer immunotherapy," Euro. J. Canc., Jan. 2008, 44(1):46-53.

Hellstrom et al., "Overexpression of HER-2 in ovarian carcinomas," Cancer Res., 2001, 61:2420-2423.

Hermanson et al., "Induced Pluripotent Stem Cell-Derived Natural Killer Cells for Treatment of Ovarian Cancer," Stem Cells, Jan. 2016, 34(1):93-101.

Hermanson et al., "Utilizing chimeric antigen receptors to direct natural killer cell activity," Front Immunol, Apr. 2015, 6:195, 6 pages.

Hermanson et al., "Utilizing chimeric antigen receptors to direct natural killer cell activity," Front. Immunol., Apr. 28, 2015, 6(Article 195), 6 pages.

Ho et al., "Costimulation of Multiple NK Cell Activation Receptors by NKG2D," J Immunol., Oct. 1, 2002, 169(7):3667-3675.

Horowitz et al., "Genetic and Environmental Determinants of Human NK Cell Diversity Revealed by Mass Cytometry," Sci. Transl. Med., Oct. 2013, 5(208):208ra145.

(56) References Cited

OTHER PUBLICATIONS

Hou et al., "The Cytoplasmic Tail of FcγRIIIAα Is Involved in Signaling by the Low Affinity Receptor for Immunoglobulin G," J. Biol. Chemistry, Sep. 13, 1996, 271(37):22815-22822.

Hsu et al., "NK cells converge lytic granules to promote cytotoxicity and prevent bystander killing," J. Cell. Biol., Dec. 2016, 215(6):875-889.

Huizinga et al., "Soluble Fcγ receptor III in human plasma originates from release by neutrophils," J Clin Invest., Aug. 1990, 86(2):416-423.

Hulett et al. The second and third extracellular domains of FcyRI (CD64) confer the unique high affinity binding of IgG2a. Mol Immunol 35: 989-996, 1998.

Imai et al., "Genetic modification of primary natural killer cells overcomes inhibitory signals and induces specific killing of leukemic cells," Blood, 2005, 106:376-383.

Jewett et al., "Tumor induced inactivation of natural killer cell cytotoxic function; implication in growth, expansion and differentiation of cancer stem cells," J Cancer, 2011, 2:443-457.

Jing et al., "Identification of an ADAM17 Cleavage Region in Human CD16 (FcγRIII) and the Engineering of a Non-Cleavable Version of the Receptor in NK Cells," PLoS One, Mar. 27, 2015, 10(3):e0121788, 14 pages.

JP Office Action in Japanese Appln. No. 2020-543244, dated Jul. 5, 2023, 18 pages (with English translation).

JP Office Action in Japanese Appln. No. 2022-035778, dated May 15, 2023, 9 pages (with English translation).

JP Office Action in Japanese Appln. No. 2022-035778, dated Oct. 16, 2023, 7 pages (with English translation).

JP Trial and Appeal Decision in Japanese Appln. No. 2020-543244, dated Nov. 27, 2023, 23 pages (with English translation).

Kahn et al., "Membrane proximal cleavage of L-selectin: identification of the cleavage site and a 6-kD transmembrane peptide fragment of L-selectin," J Cell Biol., 1994, 125:461-470.

Kaufman, "Toward clinical therapies using hematopoietic cells derived from human pluripotent stem cells," Blood, 2009, 114:3513-3523.

Kirkwood et al., "Immunotherapy of cancer in 2012," CA Cancer J Clin., 2012, 62:309-335.

Kiyoshi et al., "Structural basis for binding of human IgG1 to its high-affinity human receptor FcγRI," Nat. Commun., Apr. 2015, 6:6866.

Klingemann et al., "Natural Killer Cells for Immunotherapy—Advantages of the NK-92 Cell Line over Blood NK Cells," Front Immunol., Mar. 14, 2016, 7(Article 91), 7 pages.

Klingemann, "Are natural killer cells superior CAR drivers?" OncoImmunology, Apr. 2014, 3(4):e28147, 5 pages.

Knorr et al., "Clinical-Scale Derivation of Natural Killer Cells From Human Pluripotent Stem Cells for Cancer Therapy," Stem Cells Transl. Medicine, Apr. 2013, 2(4):274-283.

Knorr et al., "Clinical-Scale Derivation of Natural Killer Cells From Human Pluripotent Stem Cells for Cancer Therapy," Stem Cells Transl Med, Apr. 2013, 2(4):274-283.

Knorr et al., "Engineered human embryonic stem cell-derived lymphocytes to study in vivo trafficking and immunotherapy," Stem Cells and Development, Feb. 19, 2013, 22:1861-1869.

Koch et al., "Activating natural cytotoxicity receptors of natural killer cells in cancer and infection," Trends in Immunology, Apr. 2013, 34(4):182-91.

Koehl et al., "Advances in clinical NK cell studies: Donor selection, manufacturing and quality control," OncoImmunology, 2016, 5(4):e1115178, 12 pages.

Koene et al., "FcγRIIIa-158V/F Polymorphism Influences the Binding of IgG by Natural Killer Cell FcγRIIIa, Independently of the FcγRIIIa-48L/R/H Phenotype," Blood, Aug. 1997, 90(3):1109-1114.

Koneru et al., "IL-12 secreting tumor-targeted chimeric antigen receptor T cells eradicate ovarian tumors in vivo," OncoImmunology, 2015, 4(3):e994446, 12 pages.

Kruse et al., "Natural cytotoxicity receptors and their ligands," Immunology and Cell Biology, Mar. 2014, 92(3):221-229.

Kwon et al., "Stepwise phosphorylation of p65 promotes NF-κB activation and NK cell responses during target cell recognition," Nature Comm., 2016, 7:11686, 15 pages.

Lai et al., "Alterations in expression and function of signal-transducing proteins in tumor-associated T and natural killer cells in patients with ovarian carcinoma," Clin Cancer Res., 1996, 2:161-173.

Lajoie et al., "ADAM17-mediated shedding of FcγRIIIA on human NK cells: identification of the cleavage site and relationship with activation," J Immunol., 192(2):741-751, Jan. 15, 2014.

Lanier et al., "Co-association of CD3ζ with a receptor (CD16) for IgG Fc on human natural killer cells," Nature, Dec. 14, 1989, 342:803-805.

Lanier., "Up on the tightrope: natural killer cell activation and inhibition, " Nature Immunology, 2008, 9:495-502.

Lanitis et al., "Primary human ovarian epithelial cancer cells broadly express HER2 at immunologically-detectable levels," PLOS ONE, 2012, 7:e49829, 12 pages.

Le Bouteiller et al., "Engagement of CD160 receptor by HLA-C is a triggering mechanism used by circulating natural killer (NK) cells to mediate cytotoxicity," PNAS, Dec. 24, 2002, 99(26):16963-16968.

Le Garff-Tavernier et al., "Human NK cells display major phenotypic and functional changes over the life span," Aging Cell., 2010, 9:527-535.

Letourneur et al., "Characterization of the family of dimers associated with Fc receptors (Fc epsilon RI and Fc gamma RIII)," J. Immunol., Oct. 1991, 147(8):2652-2656.

Li et al., "ADAMI17 deficiency by mature neutrophils has differential effects on L-selectin shedding," Blood, 2006, 108:2275-2279.

Li et al., "Expression of chimeric antigen receptors in natural killer cells with a regulatory-compliant non-viral method," Cancer Gene Therapy, 2010, 17:147-154.

Li et al., "Human iPSC-derived natural killer cells engineered with chimeric antigen receptors enhance anti-tumor activity," Cell Stem Cell, 2018, 23:181-192.

Li et al., "The Unique Cytoplasmic Domain of Human FcγRIIIA Regulates Receptor-Mediated Function," J. Immunology, Nov. 2012, 189(9):4284-4294.

Lin-Moshier et al., "Re-evaluation of the role of calcium homeostasis endoplasmic reticulum protein (CHERP) in cellular calcium signaling," J. Biol. Chem., 2013, 288:355-367.

Liu et al., "Cord blood NK cells engineered to express IL-15 and a CD19-targeted CAR show long-term persistence and potent antitumor activity," Leukemia, 2018, 32:520-531.

Long et al., "ADAM17 activation in circulating neutrophils following bacterial challenge impairs their recruitment," J. Leukoc. Biol., Sep. 2012, 92(3):667-672.

Long et al., "Controlling Natural Killer Cell Responses: Integration of Signals for Activation and Inhibition," Annual Rev. Immunol., 2013, 31:227-258.

Long et al., "In vivo role of leukocyte ADAM17 in the inflammatory and host responses during E. coli-mediated peritonitis," J. Leukoc. Biol., Jun. 2010, 87(6):1097-1101.

Long, "Negative signaling by inhibitory receptors: the NK cell paradigm," Immunol Rev., Aug. 2008, 224(1):70-84.

Louis et al., "Cloning and sequencing of the cellular-viral junctions from the human adenovirus type 5 transformed 293 cell line," Virology, 1997, 233:423-429.

Love et al., "ITAM-mediated Signaling by the T-Cell Antigen Receptor," Cold Spring Harb. Perspect. Biol., 2010, 2:a002485, 12 pages.

Lu et al. Structure of FcyRI in complex with Fc reveals the importance of glycan recognition for high-affinity IgG binding. Proc Natl Acad Sci USA: 112(3): 833-838, 2015.

Maccio et al., "Inflammation and ovarian cancer," Cytokine., 2012, 58:133-147.

Matala et al., "The cytoplasmic domain of L-selectin participates in regulating L-selectin endoproteolysis," J Immunol., Aug. 1, 2001, 167(3):1617-1623.

(56)         References Cited

OTHER PUBLICATIONS

Maude et al., "CD19-targeted chimeric antigen receptor T-cell therapy for acute lymphoblastic leukemia," Blood, Jun. 25, 2015, 125(26):4017-4023.

Mezyk et al., "Structure and functions of tumor necrosis factor-alpha converting enzyme," Acta Biochim Pol., 2003, 50:625-645.

Migaki et al., "Mutational analysis of the membrane-proximal cleavage site of L-selectin: relaxed sequence specificity surrounding the cleavage site," J Exp Med., 1995, 182:549-557.

Miller et al., "Successful adoptive transfer and in vivo expansion of human haploidentical NK cells in patients with cancer," Blood, 2005, 105(8):3051-3057.

Miller, "Therapeutic applications: natural killer cells in the clinic," ASH Education Program Book, Dec. 2013, 2013(1):247-53.

Mishra et al., "Anti-ADAM17 monoclonal antibody MEDI3622 increases IFNγ production by human NK cells in the presence of antibody-bound tumor cells," Cancer Immunol. Immunotherapy, Sep. 2018, 67(9):1407-1416.

Montaldo et al., "Human NK cell receptors/markers: a tool to analyze NK cell development, subsets and function," Cytometry A., 2013, 83:702-713.

Moriarity et al., "Modular assembly of transposon integratable multigene vectors using RecWay assembly," Nucleic Acids Res., Apr. 1, 2013, 41(8):e92, 12 pages.

Morvan et al.., "NK cells and cancer: you can teach innate cells new tricks," Nat Rev Cancer, 2016, 16:7-19.

Nakajima et al., "Activating interactions in human NK cell recognition: the role of 2B4-CD48," Eur. J. Immunol., May 1999, 29(5):1676-1683.

Nakamura et al., "Presence and primary sequence of a high-affinity IgG receptor on canine mastocytoma (CM-MC) cells," Immunogenetics, Jun. 17, 2003, 55:271-274.

Ng et al., "A protocol describing the use of a recombinant protein-based, animal product-free medium (APEL) for human embryonic stem cell differentiation as spin embryoid bodies," Nat Protoc., 2008, 3:768-776.

Ng et al., "Forced aggregation of defined Nos. of human embryonic stem cells into embryoid bodies fosters robust, reproducible hematopoietic differentiation," Blood, 2005, 106:1601-1603.

Ngo et al. Computational complexity, protein structure prediction, and the Levinthal paradox. in The Protein Folding Problem and Tertiary Structure Prediction, pp. 492-495, 1994.

Ni et al., "Expression of Chimeric Receptor CD4ζ by Natural Killer Cells Derived from Human Pluripotent Stem Cells Improves In Vitro Activity but Does Not Enhance Suppression of HIV Infection In Vivo," Stem Cells, Apr. 2014, 32(4):1021-1031.

Ni et al., "Hematopoietic and Nature Killer Cell Development from Human Pluripotent Stem Cells," Methods Mol. Biol., Embryonic Stem Cell Immunobiology: Methods and Protocols, Jun. 2013, 1029:33-41.

Ni et al., "Human pluripotent stem cells produce natural killer cells that mediate anti-HIV-1 activity by utilizing diverse cellular mechanisms," J Viral, 2011, 85:43-50.

Nimmerjahn et al., "Fcγ receptors as regulators of immune responses," Nat. Rev. Immunol., Jan. 2008, 8(1):34-47.

Ory et al., "Sequences of complementary DNAs that encode the NA1 and NA2 forms of Fc receptor III on human neutrophils," J. Clin. Invest., Nov. 1989, 84(5):1688-1691.

Ott et al., "Potent, exceptionally selective, orally bioavailable inhibitors of TNF-alpha Converting Enzyme (TACE): novel 2-substituted-1H-benzo[d]imidazol-1-yl)methyl)benzamide Pl' substituents," Bioorg. Med. Chem. Lett., 2008, 18:1577-1582.

PCT International Preliminary Report on Patentability in International Appln. No. PCT/US2018/057689, dated Apr. 28, 2020, 5 pages.

PCT International Search Report and Written Opinion in International Appln. No. PCT/US2018/057689, dated Jan. 28, 2019, 8 pages.

Peruzzi et al., "Membrane-type 6 matrix metalloproteinase regulates the activation-induced downmodulation of CD16 in human primary NK cells," J Immunol., Aug. 15, 2013, 191(4):1883-1894.

Peschon et al., "An essential role for ectodomain shedding in mammalian development," Science, 1998, 282:1281-1284.

Porter et al., "Chimeric Antigen Receptor-Modified T Cells in Chronic Lymphoid Leukemia," N. Engl. J. Med., 2011, 365:725-733.

Qasim et al., "Molecular remission of infant B-ALL after infusion of universal TALEN gene-edited CAR T cells," Sci. Transl. Med., Jan. 25, 2017, 9(374):eaaj2013, 9 pages.

Ramos et al., "CAR-T Cell Therapy for Lymphoma," Annu. Rev. Med., 2016, 67:165-183.

Ran et al., "RUNXla enhances hematopoietic lineage commitment from human embryonic stem cells and inducible pluripotent stem cells," Blood, 2013, 121:2882-2890.

Ravetch et al., "Alternative membrane forms of Fcγ RIII(CD16) on human natural killer cells and neutrophils. Cell type-specific expression of two genes that differ in single nucleotide substitutions," J. Exp. Med., Aug. 1, 1989, 170(2):481-497.

Reiss et al., "The "a disintegrin and metalloprotease" (ADAM) family of sheddases: physiological and cellular functions," Semin. Cell. Dev. Biol., 2009, 20:126-137.

Remington's Pharmaceutical Sciences, 17th ed., Gennaro (ed), Jan. 1, 1985, 1984 pages.

Request for Reexamination in Response to the CN Decision of Rejection in Chinese Appln. No. 201880084483.4, dated Feb. 27, 2024, 23 pages (with English translation).

Romee et al., "Cytokine-induced memory-like natural killer cells exhibit enhanced responses against myeloid leukemia," Sci. Transl. Med., Sep. 21, 2016, 8(357):357ra123, 13 pages.

Romee et al., "NK cell CD16 surface expression and function is regulated by a disintegrin and metalloprotease-17 (ADAM17)," Blood, May 1, 2013, 121(18):3599-3608.

Rosen et al., "A Structural Basis for the Association of DAP12 with Mouse, but Not Human, NKG2D," J. Immunol., Aug. 15, 2004, 173(4):2470-2478.

Sadelain et al., "The basic principles of chimeric antigen receptor design," Cancer Discovery, Apr. 2013, 3(4):388-98.

Sakamoto et al., "Phase I clinical trial of autologous NK cell therapy using novel expansion method in patients with advances digestive cancer," J. Transl. Med., Aug. 25, 2015, 13:277, 13 pages.

Seidel et al., "Natural killer cell mediated antiboy-dependent cellular cytotoxicity in tumor immunotherapy with therapeutic antibodies," Front. Immunology, Mar. 27, 2013, 4:76, 9 pages.

Selvaraj et al., "The major Fc receptor in blood has a phosphatidylinositol anchor and is deficient in paroxysmal noctural hemoglobinuria," Nature, Jun. 9, 1988, 333(6173):565-567.

Sentman et al., "NKG2D CARs as cell therapy for cancer," Cancer J., Mar./Apr. 2014, 20(2):156-159.

Shemesh et al., "Splice variants of human natural cytotoxicity receptors: novel innate immune checkpoints," Cancer Immunology, Immunotherapy, Dec. 2017, 67(3), 13 pages.

Shilov et al., "The Paragon Algorithm, a next generation search engine that uses sequence temperature values and feature probabilities to identify peptides from tandem mass spectra," Mal. Cell Proteomics., Sep. 2007, 6(9):1638-1655.

Shimasaki et al., "A clinically adaptable method to enhance the cytotoxicity of natural killer cells against B-cell malignancies," Cytotherapy, Aug. 1, 2012, 14(7):830-840.

Siegel et al., "Cancer statistics, 2012" CA Cancer J. Clin., 2012, 62:10-29.

Sivori et al., "2B4 functions as a co-receptor in human NK cell activation," Eur. J. Immunol., 2000, 30(3):787-793.

Skolnick et al. From genes to protein structure and function: novel applications of computational approaches in the genomic era. Trends Biotechnol 18(1):34-39 2000.

Smith et al. The challenges of genome sequence annotation or the devil is in the details. Nature Biotechnol 15: 1222-1223, 1997.

Smyth et al., "Activation of NK cell cytotoxicity," Mol. Immunol., Feb. 2005, 42(4):501-510.

(56)     References Cited

OTHER PUBLICATIONS

Snyder et al., "Expression of a Recombinant High Affinity IgG Fc Receptor by Engineered NK Cells as a Docking Platform for Therapeutic mAbs to Target Cancer Cells," Front. Immunology, Dec. 6, 2018, 9:2873, 11 pages.

Song et al., "Chimeric NKG2D CAR-Expressing T Cell-Mediated Attack of Human Ovarian Cancer Is Enhanced by Histone Deacetylase Inhibition," Hum. Gene Ther., Mar. 2013, 24(3):295-305.

Song et al., "In Vivo Persistence, Tumor Localization, and Antitumor Activity of CAR-Engineered T Cells Is Enhanced by Costimulatory Signaling through CD137 (4-1BB)," Cancer Res., Jul. 2011, 71(13):4617-4627.

Srpan et al., "Shedding of CD16 disassembles the NK cell immune synapse and boosts serial engagement of target cells," J. Cell. Biol., Sep. 2018, 217(9):3267-3283.

Stawikowska et al., "Activity of ADAM17 (a disintegrin and metalloprotease 17) is regulated by its noncatalytic domains and secondary structure of its substrates," J. Biol. Chem., Aug. 2, 2013, 288:22871-22879.

Strauss-Albee et al., "Coordinated regulation of natural killer receptor expression in the maturing human immune system," J. Immunol., Nov. 2014, 193(10):4871-4879.

Strauss-Albee et al., "Human NK cell repertoire diversity reflects immune experience and correlates with viral susceptibility," Sci. Transl. Med., Jul. 2015, 7(297):297ra115.

Tatusova et al., "BLAST 2 Sequences, a new tool for comparing protein and nucleotide sequences," FEMS Microbiol. Letters, May 15, 1999, 174:247-250.

Teachey et al., "Identification of Predictive Biomarkers for Cytokine Release Syndrome after Chimeric Antigen Receptor T-cell Therapy for Acute Lymphoblastic Leukemia," Canc. Disc., Jun. 2016, 6(6):664-679.

Teillaud et al., "Natural and recombinant soluble low-affinity Fc γ R: detection, purification, and functional activities," Immunomethods., Feb. 1994, 4(1):48-64.

Teillaud et al., "Soluble CD16 binds peripheral blood mononuclear cells and inhibits pokeweed-mitogen-induced responses," Blood, Nov. 15, 1993, 82(10):3081-3090.

Themeli et al., "Generation of tumor-targeted human T lymphocytes from induced pluripotent stem cells for cancer therapy," Nature Biotechnol, Oct. 2013, 31(10):928-933.

Themeli et al., "New Cell Sources for T Cell Engineering and Adoptive Immunotherapy," Cell Stem Cell, Apr. 2, 2015, 16(4):357-366.

Thorp et al., "Shedding of the Mer tyrosine kinase receptor is mediated by ADAM17 protein through a pathway involving reactive oxygen species, protein kinase Cdelta, and p38 mitogen-activated protein kinase (MAPK)," J Biol Chem., 2011, 286:33335-33344.

Tian et al., "Bioluminescent imaging demonstrates that transplanted human embryonic stem cell-derived CD34(+) cells preferentially develop into endothelial cells," Stem Cells, 2009, 27:2675-2685.

Tokuriki et al. Stability effects of mutations and protein evolvability. Curr Opin Structural Biol 19: 596-604, 2009.

Topfer et al., "DAP12-Based Activating Chimeric Antigen Receptor for NK Cell Tumor Immunotherapy," J Immunol., Apr. 1, 2015, 194(7):3201-3212.

Tosi et al., "Surface expression of Fcγ receptor III (CD16) on chemoattractant-stimulated neutrophils is determined by both surface shedding and translocation from intracellular storage compartments," J. Clin. Invest., Aug. 1992, 90(2):462-470.

Tucher et al., "LC-MS based cleavage site profiling of the proteases ADAM10 and ADAM17 using proteome-derived peptide libraries," J. Proteome Res., 2014, 13:2205-2214.

Vanherberghen et al., "Classification of human natural killer cells based on migration behavior and cytotoxic response," Blood, Feb. 2013, 121(8):1326-1334.

Veeramani et al., "Rituximab infusion induces NK activation in lymphoma patients with the high-affinity CD16 polymorphism," Blood, Sep. 2011, 118(12):3347-3349.

Vivier et al., "Natural Killer Cell Signaling Pathways," Science., Nov. 26, 2004, 306(5701):1517-1519.

Vogelpoel et al. Control of cytokine production by human Fc gamma receptors: implications for pathogen defense and autoimmunity. Front Immunol 6: 79, 2015.

Walcheck et al., "ADAM-17-independent shedding of L-selectin," J. Leukoc. Biol., 2003, 74:389-394.

Walcheck et al., "iNK-CD64/16A cells: a promising approach for ADCC", Expert Opinion on Biological Therapy, Sep. 2019, 19(12):1229-1232.

Wang et al., "ADAM17 cleaves CD16b (FcγRIIIb) in human neutrophils," Biochim. Biophys. Acta., Mar. 2013, 1833(3):680-685.

Wang et al., "Different signaling pathways stimulate a disintegrin and metalloprotease-17 (ADAM 7) in neutrophils during apoptosis and activation," J. Biol. Chem., 2011, 286:38980-38988.

Wang et al., "Natural killer cell-produced IFN-γ and TNF-α induce target cell cytolysis through up-regulation of ICAM-1," J. Leukoc. Biol., Feb. 2012, 91(2):299-309.

Wang et al., "NK cell-mediated antibody-dependent cellular cytotoxicity in cancer immunotherapy," Front. Immunology, Jul. 27, 2015, 6:368, 15 pages.

Wang et al., "Regulation of mature ADAM17 by redox agents for L-selectin shedding," J. Immunol., Feb. 15, 2009, 182(4):2449-2457.

Warburton et al., "Treatment of HER-2/neu overexpressing breast cancer xenograft models with trastuzumab (Herceptin) and gefitinib (ZD1839): drug combination effects on tumor growth, HER-2/neu and epidermal growth factor receptor expression, and viable hypoxic cell fraction," Clin. Canc. Res., Apr. 1, 2004, 10:2512-2524.

Wells, J.A. Additivity of mutational effects in proteins. Biochemistry 29(37): 8509-8517, 1990.

Wiemik et al., "Targeting natural killer cells to acute myeloid leukemia in vitro with a CD16 x 33 bispecific killer cell engager and ADAM17 inhibition," Clin. Canc. Res., Jul. 2013, 19(14): 3844-3855.

Wikipedia.org [online], "Chimeric antigen receptor T cell" retrieved on Jul. 16, 2019, retrieved from URL<https://en.wikipedia.org/wiki/Chimeric_antigen_receptor_T_cell>, 13 pages.

Wilber et al., "Efficient and stable transgene expression in human embryonic stem cells using transposon-mediated gene transfer," Stem Cells, Nov. 2007, 25(11):2919-2927.

Wilken et al., "Trastuzumab Sensitizes Ovarian Cancer Cells to EGFR-targeted Therapeutics," J. Ovarian Res., 2010, 3:7, 9 pages.

Wolan et al., "Crystal structure of the murine NK cell-activating receptor NKG2D at 1.95 A" Nat. Immunology, Mar. 2001, 2(3):248-254.

Woll et al., "Human Embryonic Stem Cell-Derived NK Cells Acquire Functional Receptors and Cytolytic Activity," J Immunol., Oct. 15, 2005, 175(8):5095-5103.

Woll et al., "Human embryonic stem cells differentiate into a homogeneous population of natural killer cells with potent in vivo antitumor activity," Blood, Jun. 11, 2009, 113(24):6094-6101.

Wu et al., "A novel polymorphism of FcγRIIIa (CD16) alters receptor function and predisposes to autoimmune disease," J. Clin. Invest., Sep. 1997, 100(5):1059-1070.

Wu et al., "DNAM-1-based chimeric antigen receptors enhance T cell effector function and exhibit in vivo efficacy against melanoma," Cancer Immunology, Immunotherapy, Apr. 2015, 64(4):409-418.

Xie et al., "Seamless gene correction of β-thalassemia mutations in patient-specific iPSCs using CRISPR/Cas9 and piggyBac," Genome Res., 2014, 24:1526-1533.

Yahata et al., "cHS4 Insulator-mediated Alleviation of Promoter Interference during Cell-based Expression of Tandemly Associated Transgenes," J. Mol. Biol., Nov. 30, 2007, 374(3):580-590.

Yang et al., "Phase I Study of Random Healthy Donor-Derived Allogeneic Natural Killer Cell Therapy in Patients with Malignant Lymphoma or Advanced Solid Tumors," Canc. Immunol. Res., Mar. 2016, 4(3):215-224.

Zeng et al., "Generation of 'Off-the-Shelf' Natural Killer Cells from Peripheral Blood Cell-Derived Induced Pluripotent Stem Cells," Stem Cell Reports, Dec. 2017, 9(6):1796-1812.

(56)     References Cited

OTHER PUBLICATIONS

Zhang et al., "Cancer Immunotherapy Using a Bispecific NK Receptor Fusion Protein that Engages both T Cells and Tumor Cells," Canc. Res., Mar. 2011, 71(6):2066-2076.

Zhang et al., "Chimeric Antigen Receptor-Engineered NK-92 Cells: An Off-the-Shelf Cellular Therapeutic for Targeted Elimination of Cancer Cells and Induction of Protective Antitumor Immunity," Front. Immunol., May 2017, 8:533.

Zhang et al., "Generation of antitumor responses by genetic modification of primary human T cells with a chimeric NKG2D receptor," Cancer Research, Jun. 2006, 66(11):5927-5933.

* cited by examiner

FIG. 4
A
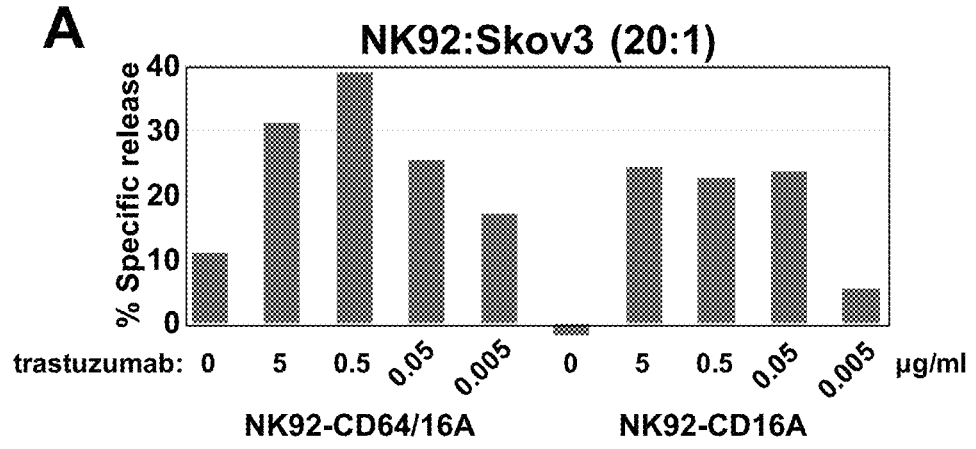
B
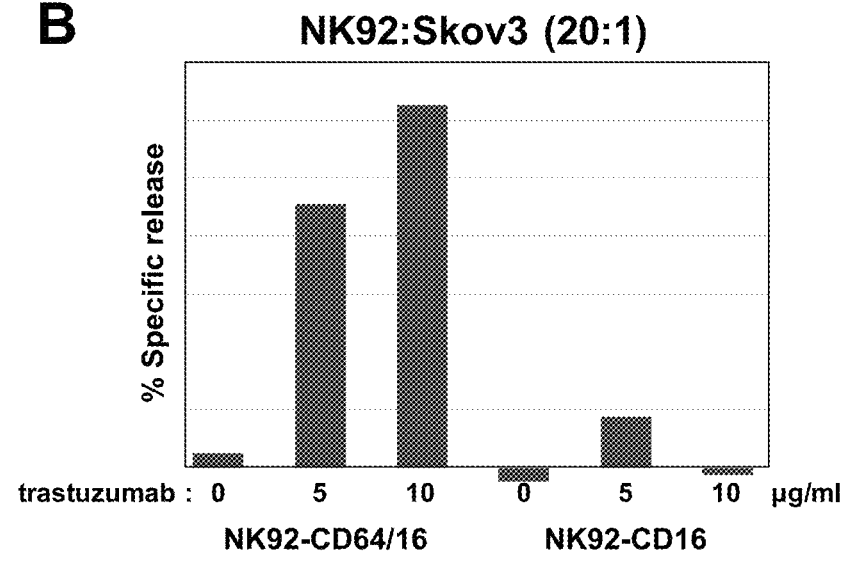

FIG. 9

```
MMFLTTLLLW VPVDGQVDTT KAVISLQPPW VSVFQEETVT    40
LHCEVLHLPG SSSTQWFLNG TATQTSTPSY RITSASVNDS    80
GEYRCQRGLS GRSDPIQLEI HRGWLLLQVS SRVFTEGEPL   120
ALRCHAWKDK LVYNVLYYRN GKAFKFFHWN SNLTLKTNI    160
SHNGTYHCSG MGKHRYTSAG ISVTVKELFP APVLNASVTS   200
PLLEGNLVTL SCETKLLLQR PGLQLYFSFY MGSKTLRGRN   240
TSSEYQILTA RREDSGLYWC EAATEDGNVL KRSPELELQV   280
LGFFPPGYQV SFCLVMVLLF AVDTGLYFSV KTNIRSSTRD   320
WKDHKFKWRK DPQDK.     336
```

FIG. 10

```
MWFLTTLLLW VPVDGQVDTT KAVISLQPPW VSVFQEETVT 40
LHCEVLHLPG SSSTQWFLNG TATQTSTPSY RITSASVNDS 80
GEYRCQRGLS GRSDPIQLEI HRGWLLLQVS SRVFTEGEPL 120
ALRCHAWKDK LVYNVLYYRN GKAFKFFHWN SNLTILKTNI 160
SHNGTYHCSG MGKHRYTSAG ISVTVKELFP APVLNASVTS 200
PLLEGNLVTL SCETKLLLQR PGLQLYFSFY MGSKTLRGRN 240
TSSEYQILTA RREDSGLYWC EAATEDGNVL KRSPELELQV 280
LGLQLPTPVW FHVLFYLAVG IMFLVNTVLW VTIRKELKRK 320
KKWDLEISLD SGHEKKVTSS LQEDRHLEEE LKCQEQKEEQ 360
LQEGVHRKEP QGAT. 375
```

FIG. 11

```
MWQLLLPTAL  LLLVSAGMRT  EDLPKAVVFL  EPQWYRVLEK   40
DSVTLKCQGA  YSPEDNSTQW  FHNESLISSQ  ASSYFIDAAT   80
VDDSGEYRCQ  TNLSTLSDPV  QLEVHIGWLL  LQAPRWVFKE  120
EDPIHLRCHS  WKNTALHKVT  YLQNGKGRKY  FHHNSDFYIP  160
KATLKDSGSY  FCRGLFGSKN  VSSETVNITI  TQGLAVSTIS  200
SFFPPGYQVS  FCLVMVLLFA  VDTGLYFSVK  TNIRSSTRDW  240
KDHKFKWRKD  PQDKRSKRSR  LLHSDYMNMT  PRRPGPTRKH  280
YQPYAPPRDF  AAYRSKRGRK  KLLYIFKQPF  MRPVQTTQEE  320
DGCSCRFPEE  EEGGCELRVK  FSRSADAPAY  QQGQNQLYNE  360
LNLGREEYD   VLDKRRGRDP  EMGGKPRRKN  PQEGLYNELQ  400
KDKMAEAYSE  IGMKGERRRG  KGHDGLYQGL  STATKDTYDA  440
LHMQALPPR.  450
```

FIG. 12

```
MWQLLLPTAL LLLVSAGMRT EDLPKAVVFL EPQWYRVLEK   40
DSVTLKCQGA YSPEDNSTQW FHNESLISSQ ASSYFIDAAT   80
VDDSGEYRCQ TNLSTLSDPV QLEVHIGWLL LQAPRWVFKE  120
EDPIHLRCHS WKNTALHKVT YLQNGKGRKY FHHNSDFYIP  160
KATLKDSGSY FCRGLFGSKN VSSETVNITI TQGLAVSTIS  200
SFFPPGYQVS FCLVMVLLFA VDTGLYFSVK TNIRSSTRDW  240
KDHKFKWRKD PQDKKRGRKK LLYIFKQPFM RPVQTTQEED  280
GCSCRFPEEE EGGCELRVKF SRSADAPAYQ QGQNQLYNEL  320
NLGRREEYDV LDKRRGRDPE MGGKPRRKNP QEGLYNELQK  360
DKMAEAYSEI GMKGERRRGK GHDGLYQGLS TATKDTYDAL  400
HMQALPPR.  409
```

FIG. 13
A
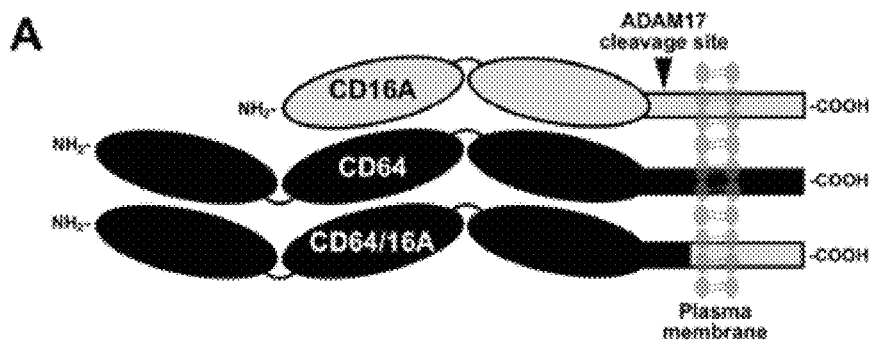
B
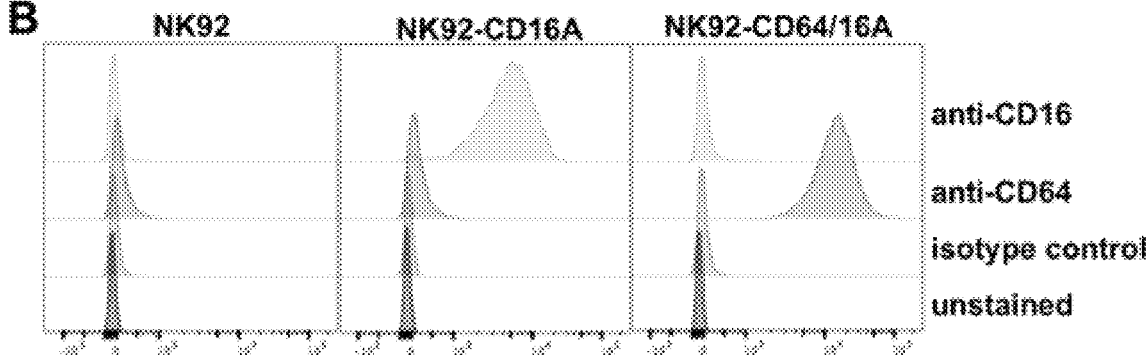
C
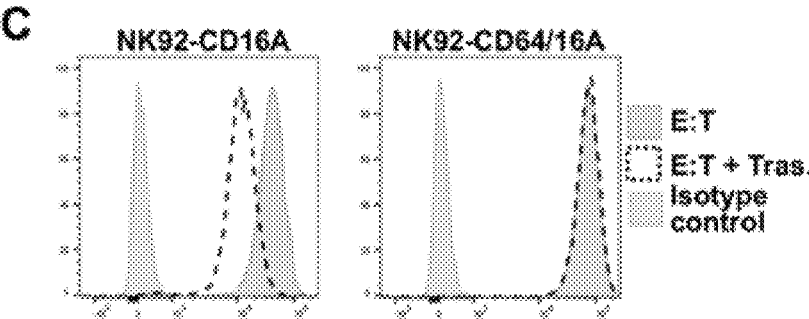

FIG. 17
A
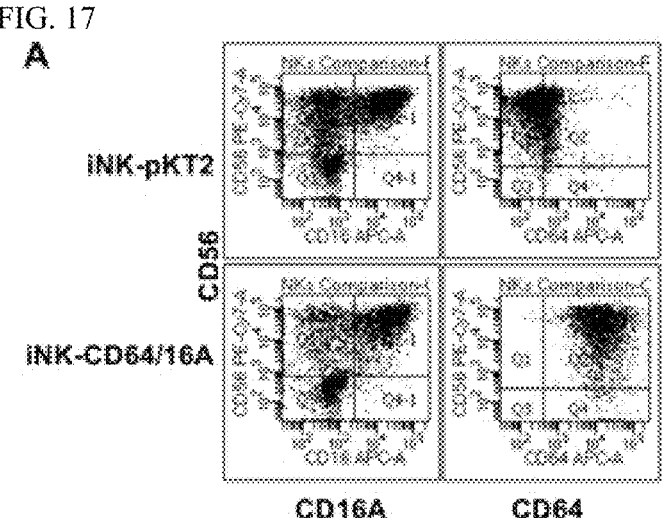
B
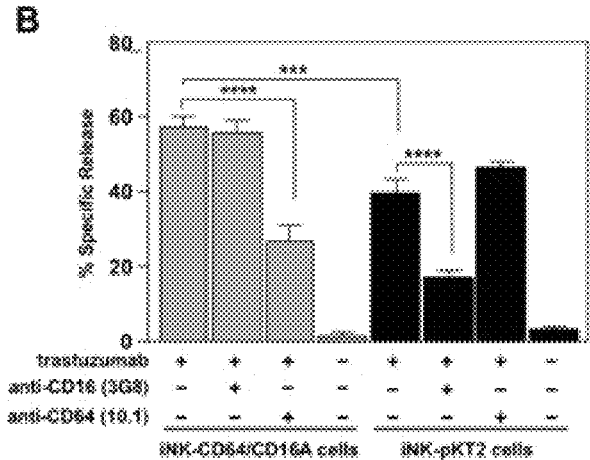
C
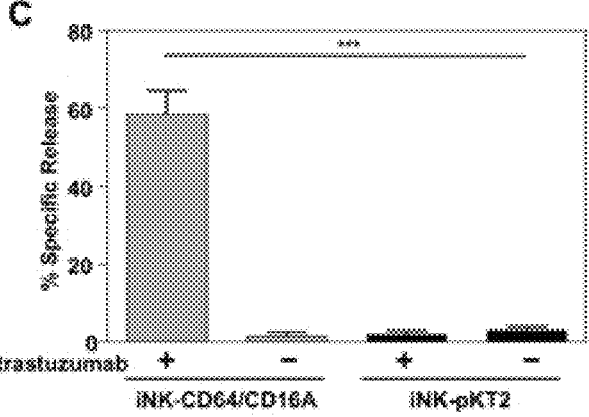

FIG. 18

```
Majority       MWQLXXXTALLLLLVSAGXXXXDKPKAVVXLEPXWXRVLXXDSVTLKCQGX
                        10        20        30        40        50 dogCD16A.pro   MWQLVSSTALLLLLVSAGT-QADVPKAVVVLEPKWNRVLTMDSVTLKCQGD  49
humCD16A.pro   MWQLLLPTALLLLLVSAGMRTEDLPKAVVFLEPQWYRVLEKDSVTLKCQGA  50

Majority       XXXXDNXTXWXHNXXXISXQXSXYXIXXAXXXXSGEYRCQTXXSXLSDPV
                        60        70        80        90       100 dogCD16A.pro   HLLRDNYT-WLHNGRPISNQISTYIIKNASIKNSGEYRCQTDQSKLSDPV  98
humCD16A.pro   YSPEDNSTQWFHNESLISSQASSYFIDAATVDDSGEYRCQTNLSTLSDPV  100

Majority       QLEVHXGWLLLQXPRXVPXEXXXIXLXCHSWKNTXXXXVXYXQNGXGXXX
                       110       120       130       140       150 dogCD16A.pro   QLEVHIGWLLLQVPRLVPQGGELIQLKCHSWKNTPVRNVQIFQNGRGKKF  148
humCD16A.pro   QLEVHIGWLLLQAPRWVPKEEDPIHLRCHSWKNTALHKVTYLQNGKGRKY  150

Majority       PXXNSXXXIPXATXXXXGSYFCRGXXGXKMXSSEXVNIXIKQGXXXXXXS
                       160       170       180       190       200 dogCD16A.pro   FYNSSEYHIPAATSEHNGSYFCRGIIGKKMESSEAVNIII-QGSSLPSTS  197
humCD16A.pro   FHHNSDFYIPKATLKDSGSYFCRGLPGSKNVSSETVNITITQGLAVSTIS  200

Majority       XXXXXXXQXXPXLVMXLLFAVDTGLYPXVXXXXRSSXXXXKXXKXXWXXX
                       210       220       230       240       250 dogCD16A.pro   LLLSHWPQIPFSLVMALLFAVDTGLYPAVQRDLSSMGNLKDSKVINSQG  247
humCD16A.pro   SFFPPGYQVSFCLVMVLLFAVDTGLYPSVKTNIRSSTRDWKDHKFKWRKD  250

Majority       XXXX dogCD16A.pro   S.                                                  249
humCD16A.pro   PQDK                                                254
```

Decoration 'Decoration #1': Shade (with deep red at 40% fill)
residues that match the Consensus exactly.

Decoration 'Decoration #1': Shade (with deep red at 40% fill) residues that match the Consensus exactly.

SEQUENCE LISTING

Sequence total quantity: 35
SEQ ID NO: 1              moltype = AA   length = 335
FEATURE                   Location/Qualifiers
source                    1..335
                          mol_type = protein
                          organism = synthetic construct
SEQUENCE: 1
MWFLTTLLLW VPVDGQVDTT KAVISLQPPW VSVFQEETVT LHCEVLHLPG SSSTQWFLNG   60
TATQTSTPSY RITSASVNDS GEYRCQRGLS GRSDPIQLEI HRGWLLLQVS SRVFTEGEPL  120
ALRCHAWKDK LVYNVLYYRN GKAFKFFHWN SNLTILKTNI SHNGTYHCSG MGKHRYTSAG  180
ISVTVKELFP APVLNASVTS PLLEGNLVTL SCETKLLLQR PGLQLYFSFY MGSKTLRGRN  240
TSSEYQILTA RREDSGLYWC EAATEDGNVL KRSPELELQV LGFFPPGYQV SFCLVMVLLF  300
AVDTGLYFSV KTNIRSSTRD WKDHKFKWRK DPQDK                             335

SEQ ID NO: 2              moltype = AA   length = 374
FEATURE                   Location/Qualifiers
source                    1..374
                          mol_type = protein
                          organism = synthetic construct
SEQUENCE: 2
MWFLTTLLLW VPVDGQVDTT KAVISLQPPW VSVFQEETVT LHCEVLHLPG SSSTQWFLNG   60
TATQTSTPSY RITSASVNDS GEYRCQRGLS GRSDPIQLEI HRGWLLLQVS SRVFTEGEPL  120
ALRCHAWKDK LVYNVLYYRN GKAFKFFHWN SNLTILKTNI SHNGTYHCSG MGKHRYTSAG  180
ISVTVKELFP APVLNASVTS PLLEGNLVTL SCETKLLLQR PGLQLYFSFY MGSKTLRGRN  240
TSSEYQILTA RREDSGLYWC EAATEDGNVL KRSPELELQV LGLQLPTPVW PHVLFYLAVG  300
IMFLVNTVLW VTIRKELKRK KKWDLEISLD SGHEKKVTSS LQEDRHLEEE LKCQEQKEEQ  360
LQEGVHRKEP QGAT                                                   374

SEQ ID NO: 3              moltype = AA   length = 449
FEATURE                   Location/Qualifiers
source                    1..449
                          mol_type = protein
                          organism = synthetic construct
SEQUENCE: 3
MWQLLLPTAL LLLVSAGMRT EDLPKAVVFL EPQWYRVLEK DSVTLKCQGA YSPEDNSTQW   60
FHNESLISSQ ASSYFIDAAT VDDSGEYRCQ TNLSTLSDPV QLEVHIGWLL LQAPRWVFKE  120
EDPIHLRCHS WKNTALHKVT YLQNGKGRKY FHHNSDFYIP KATLKDSGSY FCRGLFGSKN  180
VSSETVNITI TQGLAVSTIS SFFPPGYQVS FCLVMVLLFA VDTGLYFSVK TNIRSSTRDW  240
KDHKFKWRKD PQDKRSKRSR LLHSDYMNMT PRRPGPTRKH YQPYAPPRDF AAYRSKRGRK  300
KLLYIFKQPF MRPVQTTQEE DGCSCRFPEE EEGGCELRVK FSRSADAPAY QQGQNQLYNE  360
LNLGRREEYD VLDKRRGRDP EMGGKPRRKN PQEGLYNELQ KDKMAEAYSE IGMKGERRRG  420
KGHDGLYQGL STATKDTYDA LHMQALPPR                                   449

SEQ ID NO: 4              moltype = AA   length = 408
FEATURE                   Location/Qualifiers
source                    1..408
                          mol_type = protein
                          organism = synthetic construct
SEQUENCE: 4
MWQLLLPTAL LLLVSAGMRT EDLPKAVVFL EPQWYRVLEK DSVTLKCQGA YSPEDNSTQW   60
FHNESLISSQ ASSYFIDAAT VDDSGEYRCQ TNLSTLSDPV QLEVHIGWLL LQAPRWVFKE  120
EDPIHLRCHS WKNTALHKVT YLQNGKGRKY FHHNSDFYIP KATLKDSGSY FCRGLFGSKN  180
VSSETVNITI TQGLAVSTIS SFFPPGYQVS FCLVMVLLFA VDTGLYFSVK TNIRSSTRDW  240
KDHKFKWRKD PQDKKRGRKK LLYIFKQPFM RPVQTTQEED GCSCRFPEEE EGGCELRVKF  300
SRSADAPAYQ QGQNQLYNEL NLGRREEYDV LDKRRGRDPE MGGKPRRKNP QEGLYNELQK  360
DKMAEAYSEI GMKGERRRGK GHDGLYQGLS TATKDTYDAL HMQALPPR              408

SEQ ID NO: 5              moltype = AA   length = 248
FEATURE                   Location/Qualifiers
source                    1..248
                          mol_type = protein
                          organism = Canis lupus
SEQUENCE: 5
MWQLVSSTAL LLLVSAGTQA DVPKAVVVLE PKWNRVLTMD SVTLKCQGDH LLRDNYTWLH   60
NGRPISNQIS TYIIKNASIK NSGEYRCQTD QSKLSDPVQL EVHTGWLLLQ VPRLVFQEGE  120
LIQLKCHSWK NTPVRNVQYF QNGRGKKFFY NNSEYHIPAA TSEHNGSYFC RGIIGKKNES  180
SEAVNIIQG SSLPSTSLLL SHWPQIPFSL VMALLFAVDT GLYFAVQRDL RSSMGNLKNS  240
KVIWSQGS                                                          248

SEQ ID NO: 6              moltype = AA   length = 254
FEATURE                   Location/Qualifiers
source                    1..254
                          mol_type = protein
                          organism = Homo sapiens
SEQUENCE: 6
MWQLLLPTAL LLLVSAGMRT EDLPKAVVFL EPQWYRVLEK DSVTLKCQGA YSPEDNSTQW   60
FHNESLISSQ ASSYFIDAAT VDDSGEYRCQ TNLSTLSDPV QLEVHIGWLL LQAPRWVFKE  120
EDPIHLRCHS WKNTALHKVT YLQNGKGRKY FHHNSDFYIP KATLKDSGSY FCRGLFGSKN  180

-continued

```
VSSETVNITI TQGLAVSTIS SFFPPGYQVS FCLVMVLLFA VDTGLYFSVK TNIRSSTRDW    240
KDHKFKWRKD PQDK                                                      254

SEQ ID NO: 7             moltype = AA   length = 372
FEATURE                  Location/Qualifiers
source                   1..372
                         mol_type = protein
                         organism = Canis lupus
SEQUENCE: 7
MWLLTVLLLW VPAGAQTDPV KAVITLQPPW VSVFQEESVT LWCEGPHLPG DSSTQWFLNG    60
TATQTLTPRY RIAAASVNDN GEYRCQTGLS VLSDPIQLGI HRDWLILQVS GRVFTEGEPL    120
TLRCHGWNNK LVYNVLFYQN GTVLKFSPQN SEFTILKTTL HHNGIYHCSA MGKHRYESAG    180
VSITIKELFP APVLKASLSS PILEGHVVNL SCETKLLLQR PGLQLYFSFY MGSKTLLSRN    240
TSSEYQILTA KKEDSGLYWC EATTEDGNVV KRSPELELQV VGPQTLTPVW FHVLFYVAMG    300
MIFLVDTIFC MIIHKELQRK KKWNLEISLY SGLEKRVDSY LQKERDLEEP KYQELEQLQE    360
KTPQKPPEGE QQ                                                        372

SEQ ID NO: 8             moltype = AA   length = 374
FEATURE                  Location/Qualifiers
source                   1..374
                         mol_type = protein
                         organism = Homo sapiens
SEQUENCE: 8
MWFLTTLLLW VPVDGQVDTT KAVITLQPPW VSVFQEETVT LHCEVLHLPG SSSTQWFLNG    60
TATQTSTPSY RITSASVNDS GEYRCQRGLS GRSDPIQLEI HRGWLLLQVS SRVFTEGEPL    120
ALRCHAWKDK LVYNVLYYRN GKAFKFFHWN SNLTILKTNI SHNGTYHCSG MGKHRYTSAG    180
ISVTVKELFP APVLNASVTS PLLEGNLVTL SCETKLLLQR PGLQLYFSFY MGSKTLRGRN    240
TSSEYQILTA RREDSGLYWC EAATEDGNVL KRSPELELQV LGLQLPTPVW FHVLFYLAVG    300
IMFLVNTVLW VTIRKELKRK KKWDLEISLD SGHEKKVISS LQEDRHLEEE LKCQEQKEEQ    360
LQEGVHRKEP QGAT                                                      374

SEQ ID NO: 9             moltype = AA   length = 374
FEATURE                  Location/Qualifiers
source                   1..374
                         mol_type = protein
                         organism = synthetic construct
SEQUENCE: 9
MWFLTTLLLW VPVDGQVDTT KAVITLQPPW VSVFQEETVT LHCEVLHLPG SSSTQWFLNG    60
TATQTSTPSY RITSASVNDS GEYRCQRGLS GRSDPIQLEI HRGWLLLQVS SRVFTEGEPL    120
ALRCHAWKDK LVYNVLYYRN GKAFKFFHWN SNLTILKTNI SHNGTYHCSG MGKHRYTSAG    180
ISVTVKELFP APVLNASVTS PLLEGNLVTL SCETKLLLQR PGLQLYFSFY MGSKTLRGRN    240
TSSEYQILTA RREDSGLYWC EAATEDGNVL KRSPELELQV LGLQLPTPVW FHVLFYLAVG    300
IMFLVNTVLW VTIRKELKRK KKWDLEISLD SGHEKKVISS LQEDRHLEEE LKCQEQKEEQ    360
LQEGVHRKEP QGAT                                                      374

SEQ ID NO: 10            moltype = AA   length = 374
FEATURE                  Location/Qualifiers
source                   1..374
                         mol_type = protein
                         organism = synthetic construct
SEQUENCE: 10
MWFLTTLLLW VPVDGQVDTT KAVITLQPPW VSVFQEETVT LHCEVLHLPG SSSTQWFLNG    60
TATQTSTPSY RITSASVNDS GEYRCQRGLS GRSDPIQLEI HRGWLLLQVS SRVFTEGEPL    120
ALRCHAWKDK LVYNVLYYRN GKAFKFFHWN SNLTILKTNI SHNGTYHCSG MGKHRYTSAG    180
ISVTVKELFP APVLNASVTS PLLEGNLVTL SCETKLLLQR PGLQLYFSFY MGSKTLRGRN    240
TSSEYQILTA RREDSGLYWC EAATEDGNVL KRSPELELQV LGLQLPTPVW FHVLFYLAVG    300
IMFLVNTVLW VTIRKELKRK KKWNLEISLD SGHEKKVISS LQEDRHLEEE LKCQEQKEEQ    360
LQEGVHRKEP QGAT                                                      374

SEQ ID NO: 11            moltype = AA   length = 335
FEATURE                  Location/Qualifiers
source                   1..335
                         mol_type = protein
                         organism = synthetic construct
SEQUENCE: 11
MWFLTTLLLW VPVDGQVDTT KAVITLQPPW VSVFQEETVT LHCEVLHLPG SSSTQWFLNG    60
TATQTSTPSY RITSASVNDS GEYRCQRGLS GRSDPIQLEI HRGWLLLQVS SRVFTEGEPL    120
ALRCHAWKDK LVYNVLYYRN GKAFKFFHWN SNLTILKTNI SHNGTYHCSG MGKHRYTSAG    180
ISVTVKELFP APVLNASVTS PLLEGNLVTL SCETKLLLQR PGLQLYFSFY MGSKTLRGRN    240
TSSEYQILTA RREDSGLYWC EAATEDGNVL KRSPELELQV LGFFPPGYQV SFCLVMVLLF    300
AVDTGLYFSV KTNIRSSTRD WKDHKFKWRK DPQDK                               335

SEQ ID NO: 12            moltype = AA   length = 530
FEATURE                  Location/Qualifiers
source                   1..530
                         mol_type = protein
                         organism = synthetic construct
SEQUENCE: 12
MWFLTTLLLW VPVDGQVDTT KAVISLQPPW VSVFQEETVT LHCEVLHLPG SSSTQWFLNG    60
```

```
TATQTSTPSY RITSASVNDS GEYRCQRGLS GRSDPIQLEI HRGWLLLQVS SRVFTEGEPL     120
ALRCHAWKDK LVYNVLYYRN GKAFKFFHWN SNLTILKTNI SHNGTYHCSG MGKHRYTSAG     180
ISVTVKELFP APVLNASVTS PLLEGNLVTL SCETKLLLQR PGLQLYFSFY MGSKTLRGRN     240
TSSEYQILTA RREDSGLYWC EAATEDGNVL KRSPELELQV LGFFPPGYQV SFCLVMVLLF     300
AVDTGLYFSV KTNIRSSTRD WKDHKFKWRK DPQDKRSKRS RLLHSDYMNM TPRRPGPTRK     360
HYQPYAPPRD FAAYRSKRGR KKLLYIFKQP FMRPVQTTQE EDGCSCRFPE EEEGGCELRV     420
KFSRSADAPA YQQGQNQLYN ELNLGRREEY DVLDKRRGRD PEMGGKPRRK NPQEGLYNEL     480
QKDKMAEAYS EIGMKGERRR GKGHDGLYQG LSTATKDTYD ALHMQALPPR               530

SEQ ID NO: 13               moltype = AA  length = 460
FEATURE                     Location/Qualifiers
source                      1..460
                            mol_type = protein
                            organism = synthetic construct
SEQUENCE: 13
MWFLTTLLLW VPVDGQVDTT KAVITLQPPW VSVFQEETVT LHCEVLHLPG SSSTQWFLNG     60
TATQTSTPSY RITSASVNDS GEYRCQRGLS GRSDPIQLEI HRGWLLLQVS SRVFTEGEPL     120
ALRCHAWKDK LVYNVLYYRN GKAFKFFHWN SNLTILKTNI SHNGTYHCSG MGKHRYTSAG     180
ISVTVKELFP APVLNASVTS PLLEGNLVTL SCETKLLLQR PGLQLYFSFY MGSKTLRGRN     240
TSSEYQILTA RREDSGLYWC EAATEDGNVL KRSPELELQV LGFFPPGYQV SFCLVMVLLF     300
AVDTGLYFSV KTNIRSSTRD WKDHKFKWRK DPQDKRSKRS RLLHSDYMNM TPRRPGPTRK     360
HYQPYAPPRD FAAYRSKRGR KKLLYIFKQP FMRPVQTTQE EDGCSCRFPE EEEGGCELRL     420
KIQVRKAAIT SYEKSDGVYT GLSTRNQETY ETLKHEKPPQ                          460

SEQ ID NO: 14               moltype = AA  length = 440
FEATURE                     Location/Qualifiers
source                      1..440
                            mol_type = protein
                            organism = synthetic construct
SEQUENCE: 14
MWFLTTLLLW VPVDGQVDTT KAVITLQPPW VSVFQEETVT LHCEVLHLPG SSSTQWFLNG     60
TATQTSTPSY RITSASVNDS GEYRCQRGLS GRSDPIQLEI HRGWLLLQVS SRVFTEGEPL     120
ALRCHAWKDK LVYNVLYYRN GKAFKFFHWN SNLTILKTNI SHNGTYHCSG MGKHRYTSAG     180
ISVTVKELFP APVLNASVTS PLLEGNLVTL SCETKLLLQR PGLQLYFSFY MGSKTLRGRN     240
TSSEYQILTA RREDSGLYWC EAATEDGNVL KRSPELELQV LGFFPPGYQV SFCLVMVLLF     300
AVDTGLYFSV KTNIRSSTRD WKDHKFKWRK DPQDKRSKRS RLLHSDYMNM TPRRPGPTRK     360
HYQPYAPPRD FAAYRSKRGR KKLLYIFKQP FMRPVQTTQE EDGCSCRFPE EEEGGCELAR     420
PRRSPAQEDG KVYINMPGRG                                               440

SEQ ID NO: 15               moltype = AA  length = 467
FEATURE                     Location/Qualifiers
source                      1..467
                            mol_type = protein
                            organism = synthetic construct
SEQUENCE: 15
MWFLTTLLLW VPVDGQVDTT KAVITLQPPW VSVFQEETVT LHCEVLHLPG SSSTQWFLNG     60
TATQTSTPSY RITSASVNDS GEYRCQRGLS GRSDPIQLEI HRGWLLLQVS SRVFTEGEPL     120
ALRCHAWKDK LVYNVLYYRN GKAFKFFHWN SNLTILKTNI SHNGTYHCSG MGKHRYTSAG     180
ISVTVKELFP APVLNASVTS PLLEGNLVTL SCETKLLLQR PGLQLYFSFY MGSKTLRGRN     240
TSSEYQILTA RREDSGLYWC EAATEDGNVL KRSPELELQV LGFFPPGYQV SFCLVMVLLF     300
AVDTGLYFSV KTNIRSSTRD WKDHKFKWRK DPQDKRSKRS RLLHSDYMNM TPRRPGPTRK     360
HYQPYAPPRD FAAYRSKRGR KKLLYIFKQP FMRPVQTTQE EDGCSCRFPE EEEGGCELGR     420
LVPRGRGAAE AATRKQRITE TESPYQELQG QRSDVYSDLN TQRPYYK                  467

SEQ ID NO: 16               moltype = AA  length = 510
FEATURE                     Location/Qualifiers
source                      1..510
                            mol_type = protein
                            organism = synthetic construct
SEQUENCE: 16
MWFLTTLLLW VPVDGQVDTT KAVITLQPPW VSVFQEETVT LHCEVLHLPG SSSTQWFLNG     60
TATQTSTPSY RITSASVNDS GEYRCQRGLS GRSDPIQLEI HRGWLLLQVS SRVFTEGEPL     120
ALRCHAWKDK LVYNVLYYRN GKAFKFFHWN SNLTILKTNI SHNGTYHCSG MGKHRYTSAG     180
ISVTVKELFP APVLNASVTS PLLEGNLVTL SCETKLLLQR PGLQLYFSFY MGSKTLRGRN     240
TSSEYQILTA RREDSGLYWC EAATEDGNVL KRSPELELQV LGLQLPTPFW VLVVVGGVLA     300
CYSLLVTVAF IIFWVRSKRS RLLHSDYMNM TPRRPGPTRK HYQPYAPPRD FAAYRSKRGR     360
KKLLYIFKQP FMRPVQTTQE EDGCSCRFPE EEEGGCELRV KFSRSADAPA YQQGQNQLYN     420
ELNLGRREEY DVLDKRRGRD PEMGGKPRRK NPQEGLYNEL QKDKMAEAYS EIGMKGERRR     480
GKGHDGLYQG LSTATKDTYD ALHMQALPPR                                    510

SEQ ID NO: 17               moltype = AA  length = 343
FEATURE                     Location/Qualifiers
source                      1..343
                            mol_type = protein
                            organism = synthetic construct
SEQUENCE: 17
MWFLTTLLLW VPVDGQVDTT KAVITLQPPW VSVFQEETVT LHCEVLHLPG SSSTQWFLNG     60
TATQTSTPSY RITSASVNDS GEYRCQRGLS GRSDPIQLEI HRGWLLLQVS SRVFTEGEPL     120
ALRCHAWKDK LVYNVLYYRN GKAFKFFHWN SNLTILKTNI SHNGTYHCSG MGKHRYTSAG     180
```

```
ISVTVKELFP APVLNASVTS PLLEGNLVTL SCETKLLLQR PGLQLYFSFY MGSKTLRGRN  240
TSSEYQILTA RREDSGLYWC EAATEDGNVL KRSPELELQV LGAPREKYWL QFFIPLLVVI  300
LFAVDTGLFI STQQQVTFLL KIKRTRKGFR LLNPHPKPNP KNN                    343

SEQ ID NO: 18             moltype = AA  length = 335
FEATURE                   Location/Qualifiers
source                    1..335
                          mol_type = protein
                          organism = synthetic construct
SEQUENCE: 18
MWFLTTLLLW VPVDGQVDTT KAVITLQPPW VSVFQEETVT LHCEVLHLPG SSSTQWFLNG  60
TATQTSTPSY RITSASVNDS GEYRCQRGLS GRSDPIQLEI HRGWLLLQVS SRVFTEGEPL  120
ALRCHAWKDK LVYNVLYYRN GKAFKFFHWN SNLTILKTNI SHNGTYHCSG MGKHRYTSAG  180
ISVTVKELFP APVLNASVTS PLLEGNLVTL SCETKLLLQR PGLQLYFSFY MGSKTLRGRN  240
TSSEYQILTA RREDSGLYWC EAATEDGNVL KRSPELELQV LGFFPPGYQV SFCLVMVLLF  300
AVDTGLYFSV KTNIRGAGRD WKDHKFKWRK DPQDK                             335

SEQ ID NO: 19             moltype = AA  length = 561
FEATURE                   Location/Qualifiers
source                    1..561
                          mol_type = protein
                          organism = synthetic construct
SEQUENCE: 19
MWFLTTLLLW VPVDGQVDTT KAVITLQPPW VSVFQEETVT LHCEVLHLPG SSSTQWFLNG  60
TATQTSTPSY RITSASVNDS GEYRCQRGLS GRSDPIQLEI HRGWLLLQVS SRVFTEGEPL  120
ALRCHAWKDK LVYNVLYYRN GKAFKFFHWN SNLTILKTNI SHNGTYHCSG MGKHRYTSAG  180
ISVTVKELFP APVLNASVTS PLLEGNLVTL SCETKLLLQR PGLQLYFSFY MGSKTLRGRN  240
TSSEYQILTA RREDSGLYWC EAATEDGNVL KRSPELELQV LGSNLFVASW IAVMIIFRIG  300
MAVAIFCCFF FPSGGSGGGS GWRRKRKEKQ SETSPKEFLT IYEDVKDLKT RRNHEQEQTF  360
PGGGSTIYSM IQSQSSAPTS QEPAYTLYSL IQPSRKSGSR KRNHSPSFNS TIYEVIGKSQ  420
PKAQNPARLS RKELENFDVY SGGSGGGSGR VKFSRSADAP AYKQGQNQLY NELNLGRREE  480
YDVLDKRRGR DPEMGGKPRR KNPQEGLYNE LQKDKMAEAY SEIGMKGERR RGKGHDGLYQ  540
GLSTATKDTY DALHMQALPP R                                           561

SEQ ID NO: 20             moltype = AA  length = 575
FEATURE                   Location/Qualifiers
source                    1..575
                          mol_type = protein
                          organism = synthetic construct
SEQUENCE: 20
MWFLTTLLLW VPVDGQVDTT KAVITLQPPW VSVFQEETVT LHCEVLHLPG SSSTQWFLNG  60
TATQTSTPSY RITSASVNDS GEYRCQRGLS GRSDPIQLEI HRGWLLLQVS SRVFTEGEPL  120
ALRCHAWKDK LVYNVLYYRN GKAFKFFHWN SNLTILKTNI SHNGTYHCSG MGKHRYTSAG  180
ISVTVKELFP APVLNASVTS PLLEGNLVTL SCETKLLLQR PGLQLYFSFY MGSKTLRGRN  240
TSSEYQILTA RREDSGLYWC EAATEDGNVL KRSPELELQV LGFFPPGYQV SFCLVMVLLF  300
AVDTGLYFSV KTNIRSSTRD WKDHKFKWRK DPQDKWRRKR KEKQSETSPK EFLTIYEDVK  360
DLKTRRNHEQ EQTFPGGGST IYSMIQSQSS APTSQEPAYT LYSLIQPSRK SGSRKRNHSP  420
SFNSTIYEVI GKSQPKAQNP ARLSRKELEN FDVYSGGSGG GSGRVKFSRS ADAPAYKQGQ  480
NQLYNELNLG RREEYDVLDK RRGRDPEMGG KPRRKNPQEG LYNELQKDKM AEAYSEIGMK  540
GERRRGKGHD GLYQGLSTAT KDTYDALHMQ ALPPR                            575

SEQ ID NO: 21             moltype = AA  length = 505
FEATURE                   Location/Qualifiers
source                    1..505
                          mol_type = protein
                          organism = synthetic construct
SEQUENCE: 21
MWFLTTLLLW VPVDGQVDTT KAVITLQPPW VSVFQEETVT LHCEVLHLPG SSSTQWFLNG  60
TATQTSTPSY RITSASVNDS GEYRCQRGLS GRSDPIQLEI HRGWLLLQVS SRVFTEGEPL  120
ALRCHAWKDK LVYNVLYYRN GKAFKFFHWN SNLTILKTNI SHNGTYHCSG MGKHRYTSAG  180
ISVTVKELFP APVLNASVTS PLLEGNLVTL SCETKLLLQR PGLQLYFSFY MGSKTLRGRN  240
TSSEYQILTA RREDSGLYWC EAATEDGNVL KRSPELELQV LGFFPPGYQV SFCLVMVLLF  300
AVDTGLYFSV KTNIRSSTRD WKDHKFKWRK DPQDKWRRKR KEKQSETSPK EFLTIYEDVK  360
DLKTRRNHEQ EQTFPGGGST IYSMIQSQSS APTSQEPAYT LYSLIQPSRK SGSRKRNHSP  420
SFNSTIYEVI GKSQPKAQNP ARLSRKELEN FDVYSGGSGG GSGRLKIQVR KAAITSYEKS  480
DGVYTGLSTR NQETYETLKH EKPPQ                                       505

SEQ ID NO: 22             moltype = AA  length = 485
FEATURE                   Location/Qualifiers
source                    1..485
                          mol_type = protein
                          organism = synthetic construct
SEQUENCE: 22
MWFLTTLLLW VPVDGQVDTT KAVITLQPPW VSVFQEETVT LHCEVLHLPG SSSTQWFLNG  60
TATQTSTPSY RITSASVNDS GEYRCQRGLS GRSDPIQLEI HRGWLLLQVS SRVFTEGEPL  120
ALRCHAWKDK LVYNVLYYRN GKAFKFFHWN SNLTILKTNI SHNGTYHCSG MGKHRYTSAG  180
ISVTVKELFP APVLNASVTS PLLEGNLVTL SCETKLLLQR PGLQLYFSFY MGSKTLRGRN  240
TSSEYQILTA RREDSGLYWC EAATEDGNVL KRSPELELQV LGFFPPGYQV SFCLVMVLLF  300
AVDTGLYFSV KTNIRSSTRD WKDHKFKWRK DPQDKWRRKR KEKQSETSPK EFLTIYEDVK  360
```

-continued

```
DLKTRRNHEQ EQTFPGGGST IYSMIQSQSS APTSQEPAYT LYSLIQPSRK SGSRKRNHSP   420
SFNSTIYEVI GKSQPKAQNP ARLSRKELEN FDVYSGGSGG GSGARPRRSP AQEDGKVYIN   480
MPGRG                                                               485

SEQ ID NO: 23           moltype = AA  length = 512
FEATURE                 Location/Qualifiers
source                  1..512
                        mol_type = protein
                        organism = synthetic construct
SEQUENCE: 23
MWFLTTLLLW VPVDGQVDTT KAVITLQPPW VSVFQEETVT LHCEVLHLPG SSSTQWFLNG   60
TATQTSTPSY RITSASVNDS GEYRCQRGLS GRSDPIQLEI HRGWLLLQVS SRVFTEGEPL   120
ALRCHAWKDK LVYNVLYYRN GKAFKFFHWN SNLTILKTNI SHNGTYHCSG MGKHRYTSAG   180
ISVTVKELFP APVLNASVTS PLLEGNLVTL SCETKLLLQR PGLQLYFSFY MGSKTLRGRN   240
TSSEYQILTA RREDSGLYWC EAATEDGNVL KRSPELELQV LGFFPPGYQV SFCLVMVLLF   300
AVDTGLYFSV KTNIRSSTRD WKDHKFKWRK DPQDKWRRKR KEKQSETSPK EFLTIYEDVK   360
DLKTRRNHEQ EQTFPGGGST IYSMIQSQSS APTSQEPAYT LYSLIQPSRK SGSRKRNHSP   420
SFNSTIYEVI GKSQPKAQNP ARLSRKELEN FDVYSGGSGG GSGGRLVPRG RGAAEAATRK   480
QRITETESPY QELQGQRSDV YSDLNTQRPY YK                                 512

SEQ ID NO: 24           moltype = AA  length = 615
FEATURE                 Location/Qualifiers
source                  1..615
                        mol_type = protein
                        organism = synthetic construct
SEQUENCE: 24
MWFLTTLLLW VPVDGQVDTT KAVITLQPPW VSVFQEETVT LHCEVLHLPG SSSTQWFLNG   60
TATQTSTPSY RITSASVNDS GEYRCQRGLS GRSDPIQLEI HRGWLLLQVS SRVFTEGEPL   120
ALRCHAWKDK LVYNVLYYRN GKAFKFFHWN SNLTILKTNI SHNGTYHCSG MGKHRYTSAG   180
ISVTVKELFP APVLNASVTS PLLEGNLVTL SCETKLLLQR PGLQLYFSFY MGSKTLRGRN   240
TSSEYQILTA RREDSGLYWC EAATEDGNVL KRSPELELQV LGLQLPTPVW FHVLFYLAVG   300
IMFLVNTVLW VTIRKELKRK KKWDLEISLD SGHEKKVISS LQEDRHLEEE LKCQEQKEEQ   360
LQEGVHRKEP QGATGWRRKR KEKQSETSPK EFLTIYEDVK DLKTRRNHEQ EQTFPGGGST   420
IYSMIQSQSS APTSQEPAYT LYSLIQPSRK SGSRKRNHSP SFNSTIYEVI GKSQPKAQNP   480
ARLSRKELEN FDVYSGGSGG GSGRVKFSRS ADAPAYKQGQ NQLYNELNLG RREEYDVLDK   540
RRGRDPEMGG KPRRKNPQEG LYNELQKDKM AEAYSEIGMK GERRRGKGHD GLYQGLSTAT   600
KDTYDALHMQ ALPPR                                                   615

SEQ ID NO: 25           moltype = AA  length = 248
FEATURE                 Location/Qualifiers
source                  1..248
                        mol_type = protein
                        organism = Canis lupus
SEQUENCE: 25
MWQLVSSTAL LLLVSAGTQA DVPKAVVVLE PKWNRVLTMD SVTLKCQGDH LLRDNYTWLH   60
NGRPISNQIS TYIIKNASIK NSGEYRCQTD QSKLSDPVQL EVHTGWLLLQ VPRLVFQEGE   120
LIQLKCHSWK NTPVRNVQYF QNGRGKKFFY NNSEYHIPAA TSEHNGSYFC RGIIGKKNES   180
SEAVNIIIQG SSLPSTSLLL SHWPQIPFSL VMALLFAVDT GLYFAVQRDL RSSMGNLKNS   240
KVIWSQGS                                                           248

SEQ ID NO: 26           moltype = AA  length = 372
FEATURE                 Location/Qualifiers
source                  1..372
                        mol_type = protein
                        organism = Canis lupus
SEQUENCE: 26
MWLLTVLLLW VPAGAQTDPV KAVITLQPPW VSVFQEESVT LWCEGPHLPG DSSTQWFLNG   60
TATQTLTPRY RIAAASVNDN GEYRCQTGLS VLSDPIQLGI HRDWLILQVS GRVFTEGEPL   120
TLRCHGWNNK LVYNVLFYQN GTVLKFSPQN SEFTILKTTL HHNGIYHCSA MGKHRYESAG   180
VSITIKELFP APVLKASLSS PILEGHVVNL SCETKLLLQR PGLQLYFSFY MGSKTLLSRN   240
TSSEYQILTA KKEDSGLYWC EATTEDGNVV KRSPELELQV VGPQTLTPVW FHVLFYVAMG   300
MIFLVDTIFC MIIHKELQRK KKWNLEISLY SGLEKRVDSY LQKERDLEEP KYQELEQLQE   360
KTPQKPPEGE QQ                                                      372

SEQ ID NO: 27           moltype = AA  length = 287
FEATURE                 Location/Qualifiers
source                  1..287
                        mol_type = protein
                        organism = Canis lupus
SEQUENCE: 27
MWLLTVLLLW VPAGAQTDWL ILQVSGRVFT EGEPLTLRCH GWNNKLVYNV LFYQNGTVLK   60
FSPQNSEFTI LKTTLHHNGI YHCSAMGKHR YESAGVSITI KELFPAPVLK ASLSSPILEG   120
HVVNLSCETK LLLQRPGLQL YFSFYMGSKT LLSRNTSSEY QILTAKKEDS GLYWCEATTE   180
DGNVVKRSPE LELQVVGPQT LTPVWFHVLF YVAMGMIFLV DTIFCMIIHK ELQRKKKWNL   240
EISLYSGLEK RVDSYLQKER DLEEPKYQEL EQLQEKTPQK PPEGEQQ                287

SEQ ID NO: 28           moltype = DNA  length = 34
FEATURE                 Location/Qualifiers
source                  1..34
```

-continued

```
                            mol_type = other DNA
                            organism = synthetic construct
SEQUENCE: 28
cgggaattcg gagacaacat gtggttcttg acaa                                        34

SEQ ID NO: 29              moltype = DNA  length = 42
FEATURE                    Location/Qualifiers
source                     1..42
                            mol_type = other DNA
                            organism = synthetic construct
SEQUENCE: 29
ttggtaccca ggtggaaaga agccaagcac ttgaagctcc aa                                42

SEQ ID NO: 30              moltype = DNA  length = 42
FEATURE                    Location/Qualifiers
source                     1..42
                            mol_type = other DNA
                            organism = synthetic construct
SEQUENCE: 30
ttggagcttc aagtgcttgg cttctttcca cctgggtacc aa                                42

SEQ ID NO: 31              moltype = DNA  length = 33
FEATURE                    Location/Qualifiers
source                     1..33
                            mol_type = other DNA
                            organism = synthetic construct
SEQUENCE: 31
ccggaattct catttgtctt gagggtcctt tct                                          33

SEQ ID NO: 32              moltype = DNA  length = 34
FEATURE                    Location/Qualifiers
source                     1..34
                            mol_type = other DNA
                            organism = synthetic construct
SEQUENCE: 32
cgggaattcg gagacaacat gtggttcttg acaa                                        34

SEQ ID NO: 33              moltype = DNA  length = 33
FEATURE                    Location/Qualifiers
source                     1..33
                            mol_type = other DNA
                            organism = synthetic construct
SEQUENCE: 33
ccggaattct catttgtctt gagggtcctt tct                                          33

SEQ ID NO: 34              moltype = AA  length = 254
FEATURE                    Location/Qualifiers
source                     1..254
                            mol_type = protein
                            organism = synthetic construct
VARIANT                    5
                            note = X= V or L
VARIANT                    6
                            note = X= S or L
VARIANT                    7
                            note = X= S or P
VARIANT                    18
                            note = X= T or M
VARIANT                    19
                            note = X= absent or R
VARIANT                    20
                            note = X= Q or T
VARIANT                    21
                            note = X= A or E
VARIANT                    23
                            note = X= V or L
VARIANT                    29
                            note = X= V or F
VARIANT                    33
                            note = X= K or Q
VARIANT                    35
                            note = X= N or Y
VARIANT                    39
                            note = X= T or E
VARIANT                    40
                            note = X= M or K
VARIANT                    50
                            note = X= D or A
VARIANT                    51
```

-continued

```
                        note = X= H or Y
VARIANT                 52
                        note = X= L or S
VARIANT                 53
                        note = X= L or P
VARIANT                 54
                        note = X= R or E
VARIANT                 57
                        note = X= Y or S
VARIANT                 59
                        note = X= absent or Q
VARIANT                 61
                        note = X= L or F
VARIANT                 64
                        note = X= G or E
VARIANT                 65
                        note = X= R or S
VARIANT                 66
                        note = X= P or L
VARIANT                 69
                        note = X= N or S
VARIANT                 71
                        note = X= I or A
VARIANT                 73
                        note = X= T or S
VARIANT                 75
                        note = X= I or F
VARIANT                 77
                        note = X= K or D
VARIANT                 78
                        note = X= N or A
VARIANT                 80
                        note = X= S or T
VARIANT                 81
                        note = X= I or V
VARIANT                 82
                        note = X= K or D
VARIANT                 83
                        note = X= N or D
VARIANT                 92
                        note = X= D or N
VARIANT                 93
                        note = X= Q or L
VARIANT                 95
                        note = X= K or T
VARIANT                 106
                        note = X= T or I
VARIANT                 113
                        note = X= V or A
VARIANT                 116
                        note = X= L or W
VARIANT                 119
                        note = X= Q or K
VARIANT                 121
                        note = X= G or E
VARIANT                 122
                        note = X= E or D
VARIANT                 123
                        note = X= L or P
VARIANT                 125
                        note = X= Q or H
VARIANT                 127
                        note = X= K or R
VARIANT                 135
                        note = X= P or A
VARIANT                 136
                        note = X= V or L
VARIANT                 137
                        note = X= R or H
VARIANT                 138
                        note = X= N or K
VARIANT                 140
                        note = X= Q or T
VARIANT                 142
                        note = X= F or L
VARIANT                 146
                        note = X= R or K
VARIANT                 148
                        note = X= K or R
```

-continued

| | |
|---|---|
| VARIANT | 150 |
| | note = X= F or Y |
| VARIANT | 152 |
| | note = X= Y or H |
| VARIANT | 153 |
| | note = X= N or H |
| VARIANT | 156 |
| | note = X= E or D |
| VARIANT | 157 |
| | note = X= Y or F |
| VARIANT | 158 |
| | note = X= H or Y |
| VARIANT | 161 |
| | note = X= A or K |
| VARIANT | 164 |
| | note = X= S or L |
| VARIANT | 165 |
| | note = X= E or K |
| VARIANT | 166 |
| | note = X= H or D |
| VARIANT | 167 |
| | note = X= N or S |
| VARIANT | 175 |
| | note = X= I or L |
| VARIANT | 176 |
| | note = X= I or F |
| VARIANT | 178 |
| | note = X= K or S |
| VARIANT | 181 |
| | note = X= E or V |
| VARIANT | 185 |
| | note = X= A or T |
| VARIANT | 189 |
| | note = X= I or T |
| VARIANT | 191 |
| | note = X= absent or T |
| VARIANT | 194 |
| | note = X= S or L |
| VARIANT | 195 |
| | note = X= S or A |
| VARIANT | 196 |
| | note = X= L or V |
| VARIANT | 197 |
| | note = X= P or S |
| VARIANT | 198 |
| | note = X= S or T |
| VARIANT | 199 |
| | note = X= T or I |
| VARIANT | 201 |
| | note = X= L or S |
| VARIANT | 202 |
| | note = X= L or F |
| VARIANT | 203 |
| | note = X= L or F |
| VARIANT | 204 |
| | note = X= S or P |
| VARIANT | 205 |
| | note = X= H or P |
| VARIANT | 206 |
| | note = X= W or G |
| VARIANT | 207 |
| | note = X= P or Y |
| VARIANT | 209 |
| | note = X= I or V |
| VARIANT | 210 |
| | note = X= P or S |
| VARIANT | 212 |
| | note = X= S or C |
| VARIANT | 216 |
| | note = X= A or V |
| VARIANT | 228 |
| | note = X= A or S |
| VARIANT | 230 |
| | note = X= Q or K |
| VARIANT | 231 |
| | note = X= R or T |
| VARIANT | 232 |
| | note = X= D or N |
| VARIANT | 233 |

-continued

```
                          note = X= L or I
VARIANT                   237
                          note = X= M or T
VARIANT                   238
                          note = X= G or R
VARIANT                   239
                          note = X= N or D
VARIANT                   240
                          note = X= L or W
VARIANT                   242
                          note = X= N or D
VARIANT                   243
                          note = X= S or H
VARIANT                   245
                          note = X= V or F
VARIANT                   246
                          note = X= I or K
VARIANT                   248
                          note = X= S or R
VARIANT                   249
                          note = X= Q or K
VARIANT                   250
                          note = X= G or D
VARIANT                   251
                          note = X= S or P
VARIANT                   252
                          note = X= absent or Q
VARIANT                   253
                          note = X= absent or D
VARIANT                   254
                          note = X= absent or K
SEQUENCE: 34
MWQLXXXTAL LLLVSAGXXX XDXPKAVVXL EPXWXRVLXX DSVTLKCQGX XXXXDNXTXW   60
XHNXXXISXQ XSXYXIXXAX XXXSGEYRCQ TXXSXLSDPV QLEVHXGWLL LQXPRXVFXE   120
XXXIXLXCHS WKNTXXXXVX YXQNGXGXKX FXXNSXXXIP XATXXXXGSY FCRGXXGXKN   180
XSSEXVNIXI XQGXXXXXXS XXXXXXXQXX FXLVMXLLFA VDTGLYFXVX XXXRSSXXXX   240
KXXKXXWXXX XXXX                                                    254

SEQ ID NO: 35            moltype = AA  length = 372
FEATURE                  Location/Qualifiers
source                   1..372
                         mol_type = protein
                         organism = synthetic construct
VARIANT                  19
                         note = X= absent, P or T
VARIANT                  20
                         note = X= absent, V or T
VARIANT                  38
                         note = X= absent, S or T
VARIANT                  42
                         note = X= absent, W or H
VARIANT                  45
                         note = X= absent, G or V
VARIANT                  46
                         note = X= absent, P or L
VARIANT                  51
                         note = X= absent, D or S
VARIANT                  66
                         note = X= absent, L or S
VARIANT                  69
                         note = X= absent, R or S
VARIANT                  73
                         note = X= absent, A or T
VARIANT                  74
                         note = X= absent, A or S
VARIANT                  80
                         note = X= absent, N or S
VARIANT                  87
                         note = X= absent, T or R
VARIANT                  91
                         note = X= absent, V or G
VARIANT                  92
                         note = X= absent, L or R
VARIANT                  99
                         note = X= absent, G or E
VARIANT                  103
                         note = X= absent, D or G
SEQUENCE: 35
MWLLTVLLLW VPAGAQTDXX KAVITLQPPW VSVFQEEXVT LXCEXXHLPG XSSTQWFLNG   60
```

-continued

```
TATQTXTPXY RIXXASVNDX GEYRCQXGLS XXSDPIQLXI HRXWLILQVS GRVFTEGEPL  120
TLRCHGWNNK LVYNVLFYQN GTVLKFSPQN SEFTILKTTL HHNGIYHCSA MGKHRYESAG  180
VSITIKELFP APVLKASLSS PILEGHVVNL SCETKLLLQR PGLQLYFSFY MGSKTLLSRN  240
TSSEYQILTA KKEDSGLYWC EATTEDGNVV KRSPELELQV VGPQTLTPVW FHVLFYVAMG  300
MIFLVDTIFC MIIHKELQRK KKWNLEISLY SGLEKRVDSY LQKERDLEEP KYQELEQLQE  360
KTPQKPPEGE QQ                                                     372
```

TREATMENTS ADMINISTERING CHIMERIC IgG Fc RECEPTOR COMPRISING AN EXTRACELLULAR DOMAIN OF CD64

CROSS-REFERENCE TO RELATED APPLICATION

This application is a divisional of U.S. application Ser. No. 16/758,142, filed Apr. 22, 2020, which is a National Stage Application under 35 U.S.C. § 371 that claims the benefit of Application Serial No. PCT/US2018/057689, filed Oct. 26, 2018, which also claims the benefit of U.S. Provisional Application Ser. No. 62/577,425, filed Oct. 26, 2017. The disclosures of the prior applications are considered part of (and are incorporated by reference in) the disclosure of this application.

GOVERNMENT FUNDING

This invention was made with government support under CA203348 awarded by National Institutes of Health. The government has certain rights in the invention.

SEQUENCE LISTING

This application contains a Sequence Listing that has been submitted electronically as an XML file named "09531-0458002_updatedSL_ST26.XML." The XML file, created on Sep. 5, 2025, is 89,556 bytes in size. The material in the XML file is hereby incorporated by reference in its entirety.

SUMMARY

This disclosure describes, in one aspect, this disclosure describes an immune cell that expresses a heterologous IgG Fc receptor.

In some embodiments, the heterologous IgG Fc receptor can be a chimeric IgG Fc receptor. Generally, the chimeric IgG Fc receptor includes an extracellular domain, a transmembrane domain, and an intracellular domain. The extracellular domain generally includes a sufficient portion of CD64 to bind to an IgG Fc region. The intracellular domain of the chimeric IgG Fc receptor includes a sufficient portion of an Fc receptor immunoreceptor tyrosine-based activation motif (ITAM) to initiate cell signaling when an IgG Fc region binds to the extracellular domain.

In some of these embodiments, the intracellular domain includes at least a portion of the intracellular region of CD16A. In other embodiments, the intracellular domain can include at least a portion of the intracellular region of CD27, CD28, CD134 (OX40), CD137 (4-1BB), FcRγ, or CD3ζ.

In some embodiments, the chimeric IgG Fc receptor can include the CD16A extracellular cleavage site. In other embodiments, the extracellular domain of the chimeric IgG Fc receptor can lack the CD16A extracellular cleavage site.

In some embodiments, the heterologous IgG Fc receptor can include an IgG Fc receptor not natively expressed by the immune cell. In some of these embodiments, the immune cell may be a natural killer (NK) cell genetically modified to express CD64.

In another aspect, this disclosure describes a polynucleotide that encodes any embodiment of the heterologous IgG Fc receptors summarized above.

In another aspect, this disclosure describes an immune cell that is genetically modified to include the polynucleotide that encodes an embodiment of the heterologous IgG Fc receptors summarized above.

In another aspect, this disclosure describes a method of killing a tumor cell. Generally, the method includes contacting the tumor cell with an antibody that specifically binds to the tumor cell and contacting the tumor cell with any embodiment of the recombinant immune cell summarized above under conditions effective for the recombinant immune cell to kill the tumor cell.

In another aspect, this disclosure describes a method of treating a subject having a tumor. Generally, the method includes administering to the subject an antibody that specifically binds to cells of the tumor and administering to the subject a composition that includes any embodiment of the recombinant immune cell summarized above under conditions effective for the recombinant immune cell to kill cells of the tumor.

In another aspect, this disclosure describes a composition that include a complex formed between a therapeutic antibody and any embodiment of the recombinant immune cell summarized above in which the heterologous IgG Fc receptor is bound to the Fc portion of the therapeutic antibody.

In another aspect, this disclosure describes a method of treating a subject having a tumor. Generally, the method includes administering to the subject any embodiment of the composition summarized immediately wherein the therapeutic antibody specifically binds to cells of the tumor.

The above summary is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 4. NK92 cells expressing CD64/CD16A induce higher levels of ADCC than wildtype CD16A. (A) A standard ADCC assay was performed in which trastuzumab (herceptin) was included in the assay. (B) A standard ADCC assay was performed in which the NK92-CD64/CD16A and NK92-CD16A cells were pre-incubated with trastuzumab and then the mAb was washed away prior to the effector cells being incubated with the SKOV-3 target cells.

FIG. 9. Amino acid sequence of an exemplary CD64/CD16A chimeric IgG Fc receptor (SEQ ID NO:1).

FIG. 10. Amino acid sequence of CD64 IgG Fc receptor (SEQ ID NO:2).

FIG. 11. Amino acid sequence of an exemplary CD16A-CD28-BB-(chain chimeric IgG Fc receptor (SEQ ID NO:3).

FIG. 12. Amino acid sequence of an exemplary CD16A-BB-(chain chimeric IgG Fc receptor (SEQ ID NO:4).

FIG. 13. Expression of CD64/16A by NK92 cells. (A) Schematic representation of the cell membrane forms of CD16A, CD64, and CD64/16A. CD16A undergoes ectodomain shedding by ADAM17 at a membrane proximal location, as indicated, which is not present in CD64 and CD64/16A. (B) NK92 parental cells, NK92-CD16A cells, and NK92-CD64/16A cells were stained with an anti-CD16, anti-CD64, or an isotype-matched negative control mAb and examined by flow cytometry. (C) NK92-CD16A and NK92-CD64/16A cells were incubated with SKOV-3 cells with or without trastuzumab (5 μg/ml) at 37° C. (E:T=1:1) for two hours. The NK92-CD16A and NK92-CD64/16A cells were then stained with an anti-CD16 mAb or an anti-CD64 mAb, respectively, and examined by flow cytometry. Nonspecific antibody labeling was determined using the appropriate isotype-negative control mAb. Data is representative of at least three independent experiments.

FIG. 17. INK-CD64/16A cells show enhanced ADCC compared to iNK-pKT2 control cells. (A) NK cells derived from empty vector (iNK-pKT2) or CD64/16A (INK-CD64/16A) transduced iPSCs were stained for CD56, CD64, and CD16A, as indicated. (B) iNK-pKT2 and iNK-CD64/16A cells were incubated with SKOV-3 cells (E:T=10:1) in the presence or absence of trastuzumab (5 μg/ml), the function blocking anti-CD16 mAb 3G8 (5 μg/ml), and the function blocking anti-CD64 mAb 10.1 (5 μg/ml), as indicated, for two hours at 37° C. Data is shown as mean±SD of three independent experiments. Statistical significance is indicated as * p<0.001;  p<0.0001. (C) iNK-pKT2 and iNK-CD64/16A cells were incubated in the presence or absence of trastuzumab (5 μg/ml), washed, and exposed to SKOV-3 cells (E:T=10:1) for two hours at 37° C. Data is shown as mean±SD of three independent experiments. Statistical significance is indicated as * p<0.001.

FIG. 18. Sequence alignment of canine CD16A (SEQ ID NO:5) and human CD16A (SEQ ID NO:6). The sequence designated "Majority is SEQ ID NO:34.

5

6

Figure 20:
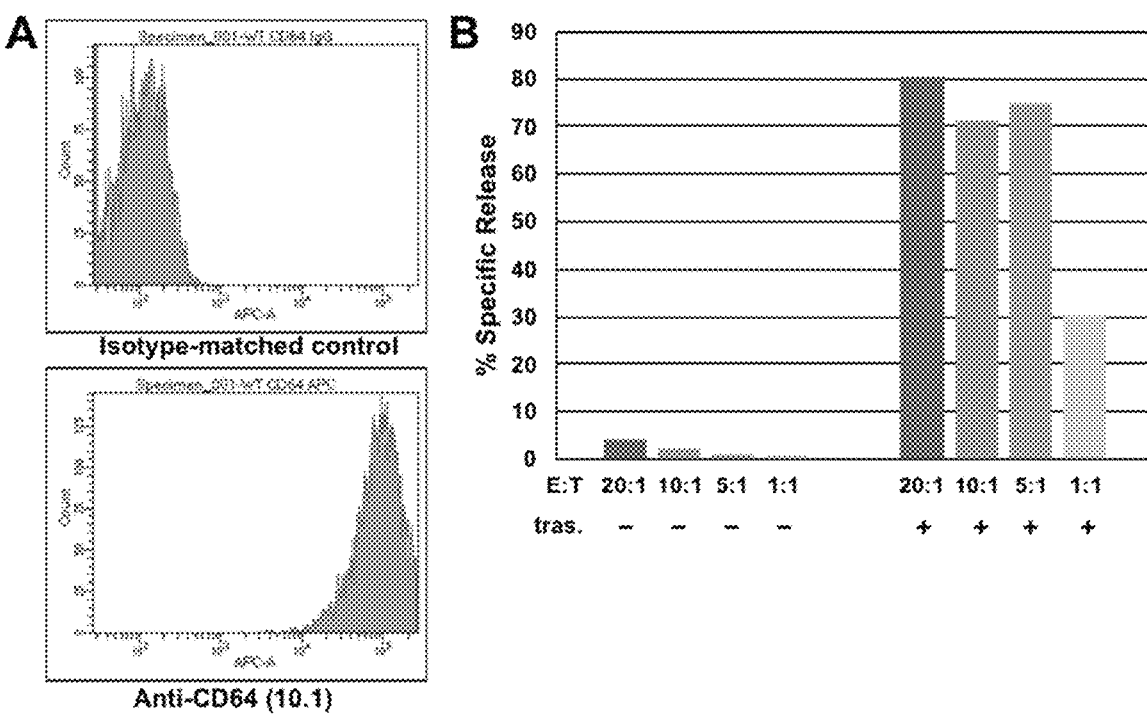

FIG. 20. NK92 cells expressing wildtype human CD64 mediate ADCC. (A) NK92-CD64 cells were stained with an isotype-matched negative control mAb or the anti-CD64 mAb (clone 10.1) and examined by flow cytometry. (B) NK92-CD64 cells were incubated with SKOV-3 cells (at the indicated E:T ratios) in the presence or absence of trastuzumab (tras.) (5 µg/ml) for two hours at 37° C. Representative data from at least three independent experiments are shown.

DETAILED DESCRIPTION OF ILLUSTRATIVE EMBODIMENTS

This disclosure describes recombinant immune cells, methods of making the recombinant immune cells, and methods of using the recombinant immune cells. Generally, the recombinant immune cells are genetically modified to include a heterologous IgG Fc receptor. In some cases, the heterologous IgG Fc receptor can be a chimeric receptor engineered include domains from two or more receptors. In other embodiments, the heterologous may be an IgG Fc receptor that is not natively expressed by the immune cell. Generally, the recombinant immune cells provide a sustained cytotoxic immune response against a target—for example, a tumor cell—that is targeted for killing by the immune cell because the target binds a therapeutic antibody that is recognized by the IgG Fc receptor.

A mechanism of cell-mediated immune defense involves the engagement of antibodies attached to target cells by Fc receptors expressed by leukocytes, which results in target cell killing. This process is referred to antibody-dependent cell-mediated cytotoxicity (ADCC).

Therapeutic monoclonal antibodies (mAbs) have been generated against a variety of tumor antigens and tested in clinical trials for treating infectious diseases, chronic diseases, and cancers including, for example, AML, breast cancer, ovarian cancer, gastric cancer, neuroblastoma, and lymphoma. Many clinically successful mAbs use ADCC as a mechanism of action. A limitation of antibody therapy, however, is the development of resistance in patients and the non-responsiveness of some malignancies.

This disclosure describes an approach for augmenting Fc receptor interactions with therapeutic antibodies. The approach involves a chimeric receptor that includes a CD16A domain and a CD64 domain.

Figure 1:
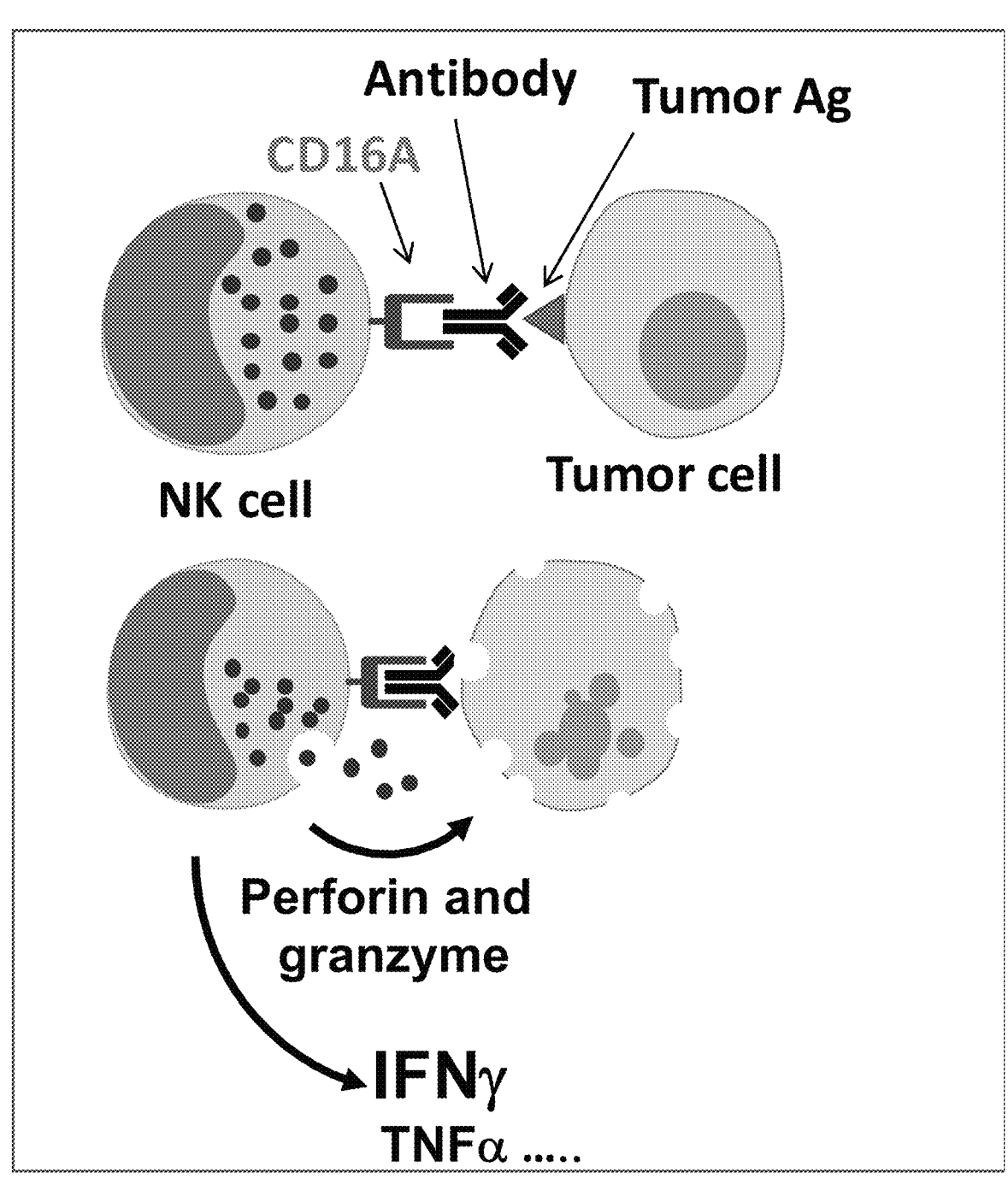
FIG. 1. Antibody-dependent cell-mediated cytotoxicity (ADCC).

CD16A (FcγRIIIA) is an IgG Fc receptor expressed by human natural killer (NK) cells, a population of cytotoxic lymphocytes, and is their sole means of recognizing IgG bound to tumor cells or virus-infected cells. CD16A is a potent activating receptor that induces ADCC by NK cells (FIG. 1). The CD16A transmembrane region is responsible for the association with CD35 and/or FcR γ-chain (FcRγ) that contain immunoreceptor tyrosine-based activation motifs (FIG. 2; FIG. 13A), and the CD16A cytoplasmic domain interacts with intracellular molecules critical for receptor functions. CD16A is a low affinity FcγR with limited capacity to engage therapeutic mAb-coated target cells. CD16A also undergoes a rapid downregulation in expression upon cell activation that markedly reduces its cell surface density and avidity for IgG. CD16A downregulation occurs by a proteolytic event at an extracellular site proximal to the plasma membrane and is referred to as ectodomain shedding. The location of this cleavage site has been reported (Jing et al., 2015. *PLoS One* 10:e0121788) and is shown schematically in FIG. 2 and FIG. 13A.

CD64 (FcγRI) is another IgG Fc receptor, and is expressed by monocytes, macrophages, and activated neutrophils. CD64 is a high affinity IgG receptor. This receptor does not undergo ectodomain shedding upon cell activation and does not naturally transduce signals for ADCC in NK cells.

This disclosure describes a chimeric FcγR that includes a CD16A domain and a CD64 domain. The chimeric receptor includes the extracellular region of human CD64 and the cytoplasmic region of human CD16A, an exemplary embodiment of which is shown schematically in FIG. 2 and FIG. 13A as CD64/16A. In various embodiments, the chimeric CD64/CD16A receptor can include the CD64 transmembrane region or the CD16A transmembrane region. The CD64/16A construct has been engineered so that it lacks the CD16A extracellular cleavage site and thus is not susceptible to ectodomain shedding (FIG. 2; FIG. 13A), but includes at least a portion of the CD16A intracellular region that is involved in intracellular signaling.

Figure 19:
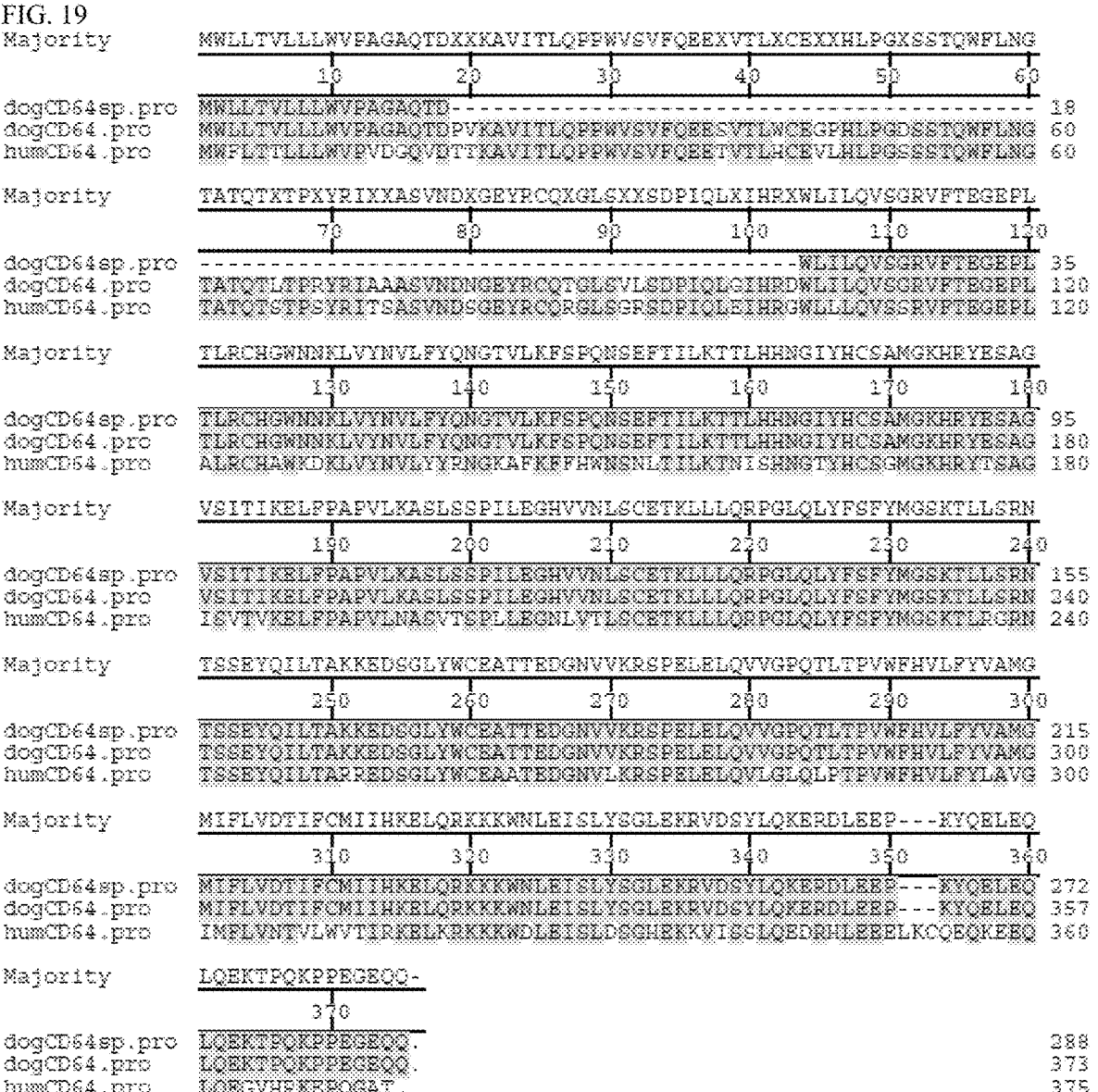
FIG. 19. Sequence alignment of canine CD64sp #19 ("dogCD64sp.pro"; SEQ ID NO: 27), canine CD64 ("dogCD64.pro"; SEQ ID NO:7), and human CD64 ("humCD64.pro"; SEQ ID NO:8). The sequence designated "Majority" is SEQ ID NO: 35.

Also, while described herein in the context of an exemplary embodiment in which the CD64 domain and the CD16A contain amino acid sequences of human CD64 and human CD16A, respectively, the chimeric FcγR described herein can include an amino acid sequence that is, or is derived from, any suitable CD64 or CD16A natively expressed by any species. FIG. 18 and FIG. 19 provide amino acid sequence alignments of human and canine amino acid sequences for CD16A (FIG. 18) and CD64 (FIG. 19).

As used herein, the amino acid sequence of a domain is "derived from" a the amino acid sequence of a reference polypeptide if the amino acid sequence of the domain possesses a specified amount of sequence similarity and/or sequence identity compared to the amino acid sequence of the reference polypeptide. Sequence similarity of can be determined by aligning the residues of the two polypeptides (for example, the domain amino acid sequence and the amino acid sequence of the reference CD16A or CD64 polypeptide) to optimize the number of identical amino acids along the lengths of their sequences. Gaps in either or both sequences are permitted in making the alignment in order to optimize the number of identical amino acids, although the amino acids in each sequence must nonetheless remain in their proper order.

A pair-wise comparison analysis of amino acid sequences can be carried out using the BESTFIT algorithm in the GCG package (version 10.2, Madison WI). Alternatively, polypeptides may be compared using the Blastp program of the BLAST 2 search algorithm, as described by Tatiana et al., (*FEMS Microbiol Lett,* 174, 247-250 (1999)), and available on the National Center for Biotechnology Information (NCBI) website. The default values for all BLAST 2 search parameters may be used, including matrix=BLOSUM62; open gap penalty=11, extension gap penalty=1, gap x_dropoff=50, expect=10, wordsize=3, and filter on.

The amino acid sequence of a domain is "derived from" a the amino acid sequence of a reference polypeptide if the amino acid sequence of the domain possesses a specified degree of amino acid sequence "identity" or amino acid sequence "similarity." Amino acid sequence identity refers to the presence of identical amino acids. Amino acid sequence similarity refers to the presence of not only identical amino acids but also the presence of conservative substitutions. A conservative substitution for an amino acid may be selected from other members of the class to which the substituted amino acid belongs. For example, it is well-known in the art of protein biochemistry that an amino acid belonging to a grouping of amino acids having a particular size or characteristic (such as charge, hydrophobicity and hydrophilicity) can be substituted for another amino acid without altering the activity of a protein, particularly in regions of the protein that are not directly associated with biological activity. For example, nonpolar (hydrophobic) amino acids include alanine, leucine, isoleucine, valine, proline, phenylalanine, tryptophan, and tyrosine. Polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Conservative substitutions include, for example, Lys for Arg and vice versa to maintain a positive charge; Glu for Asp and vice versa to maintain a negative charge; Ser for Thr so that a free-OH is maintained; and Gln for Asn to maintain a free —NH$_2$. Likewise, biologically active analogs of a polypeptide containing deletions or additions of one or more contiguous or noncontiguous amino acids that do not eliminate a functional activity of the polypeptide are also contemplated.

The amino acid sequence of a CD16A domain or a CD64 domain is "derived from" a reference amino acid sequence if the domain amino acid sequence has at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence similarity to the reference amino acid sequence.

The amino acid sequence of a CD16A domain or a CD64 domain is "derived from" a reference amino acid sequence if the domain amino acid sequence has at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the reference amino acid sequence.

For the purpose of determining whether a domain amino acid sequence is "derived from" a specified reference amino acid sequence, exemplary suitable reference polypeptides include human CD16A (SEQ ID NO:6), canine CD16A (SEQ ID NO:5), human CD64 (SEQ ID NO:8), canine CD64 (SEQ ID NO:7), canine CD64sp (SEQ ID NO:25), or the corresponding domains of any of the constructs listed in Table 1.

Figure 2:
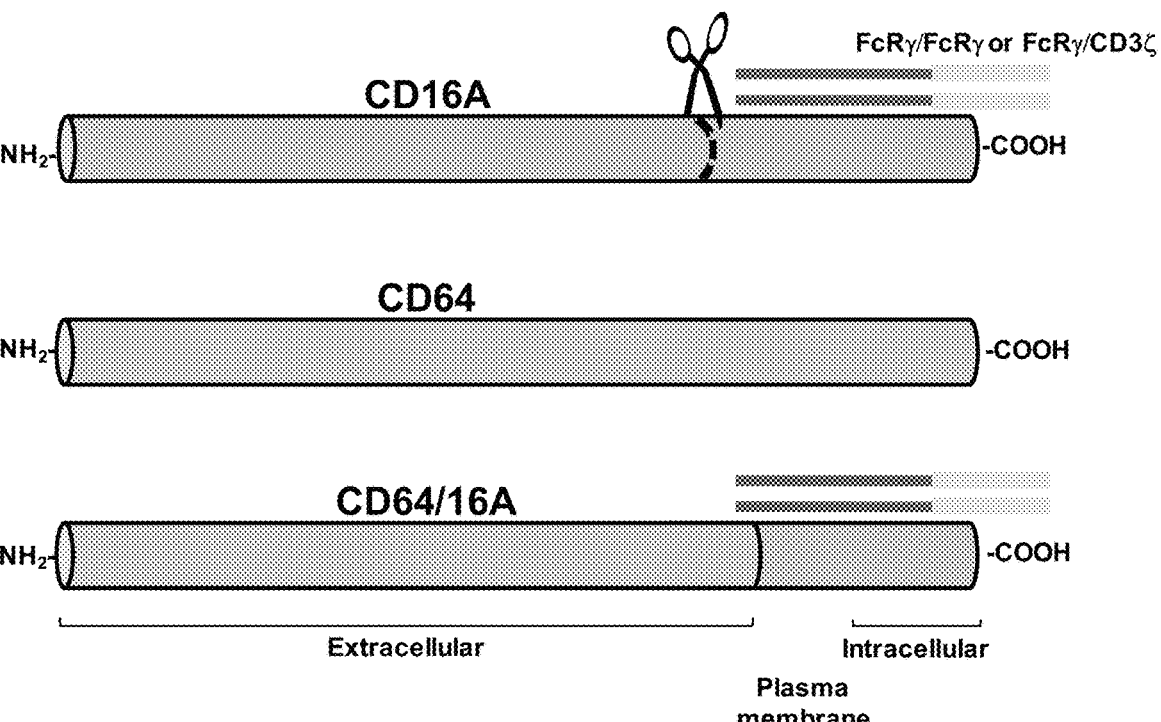
FIG. 2. Wildtype CD16A, wildtype CD64, and the CD64/16A chimeric construct. The scissors and dashed line shown for CD16A represent the extracellular proteolytic site for ectodomain shedding.

Also, while described herein in the context of an exemplary embodiment, illustrated in FIG. 2 and FIG. 13A, the chimeric receptor may be designed to include a different fusion points between CD64 and CD16A that that shown in FIG. 2 and FIG. 13A, to include the CD16A cleavage region, modified functional motifs in regions of CD64 or CD16A, and/or adding an additional signaling domain, such as, for example, a signaling domain of CD27, CD28, CD134 (OX40), CD137 (4-1BB), FcRγ, or CD35. The chimeric receptor may therefore be designed to increase the proliferation of NK cells or other effector cells, increase survival of NK cells or other effector cells, increase potency of NK cells or other effector cells, and/or decrease NK cell exhaustion in vivo.

In certain embodiments, the chimeric FcγR can be modified to include a cytoplasmic domain or a signaling domain that confers additional functionality to the chimeric receptor. For example, a chimeric FcγR can include a functional portion of CD28, which transduces signals involved in T-cell proliferation, survival, and cytokine production. As another example, a chimeric FcγR can include a functional portion of 4-1BB, which contributes to the clonal expansion, survival, and development of hematopoietic cells. As another example, a chimeric FcγR can include a functional portion of the CD39 cytoplasmic domain, which contains three immunoreceptor tyrosine-based activation motifs (ITAMs) that trigger intracellular signal-transduction pathways for ADCC, cytokine production, and cell proliferation and survival. As another example, a chimeric FcγR can include a functional portion of the FcRy cytoplasmic domain, which contains an ITAM that preferentially recruits Syk kinase to mediate intracellular signals for ADCC, cytokine production, and cell proliferation and survival. As another example, a chimeric FcγR can include a functional portion of the DAP10 cytoplasmic domain, which contains a YxxM motif that specifically activates phosphatidylinositol 3-kinase-dependent signaling pathways for cytotoxicity, cell survival, and proliferation of NK and T cells. As another example, a chimeric FcγR can include a functional portion of the DAP12 cytoplasmic domain, which contains an ITAM that triggers signals for cytotoxicity, survival, and proliferation of NK cells and T cells. As another example, a chimeric FcγR can include a functional portion of the NKG2D (or CD314) transmembrane domain, which specifically associates with DAP10 to mediate signaling pathways for cytotoxicity, cell survival, and proliferation of NK and T cells. As another example, a chimeric FcγR can include a functional portion of the 2B4 (NKR2B4 or CD244) cytoplasmic domain, which transduces signals of cytolytic granule polarization involved in enhanced cytotoxicity of NK cells. As another example, a chimeric FcγR can include a functional portion of the high affinity IgE receptor FcεR transmembrane and cytoplasmic domains, which are constitutively associated with its β-subunit and FcR γ-chain (FcRγ) to mediate the most potent degranulation signals in myeloid cells that initiates the allergic responses, which could be exploited for cancer therapy with the recombinant high affinity IgG Fc receptors.

Exemplary constructs that include exemplary cytoplasmic domain and/or signaling domain modifications are listed in Table 1.

TABLE 1

| Code | Domains (EC/TM/CY/SDs)* | Comments | SEQ ID NO: |
|---|---|---|---|
| rCD64#1 | 64/64/64/— | | 9 |
| rCD64#2 | 64/64/mut64/— | CD64 cytoplasmic domain mutation | 10 |
| rCD64#3 | 64/16A/16A/— | | 11 |
| rCD64#4 | 64/16A/16A/28-BB-CD3ç | | 12 |
| rCD64#5 | 64/16A/16A/28-BB-FcRγ | | 13 |
| rCD64#6 | 64/16A/16A/28-BB-Dap10 | | 14 |
| rCD64#7 | 64/16A/16A/28-BB-Dap12 | | 15 |
| rCD64#8 | 64/28/28/BB-CD3ç | | 16 |
| rCD64#9 | 64/FcεR/FcεR/— | | 17 |

TABLE 1-continued

| Code | Domains (EC/TM/CY/SDs)* | Comments | SEQ ID NO: |
|---|---|---|---|
| rCD64#10 | 64/16A/mut16A/— | Mutation on PKC phosphorylation site | 18 |
| rCD64#11 | 64/G2D/2B4/CD3ç | | 19 |
| rCD64#12 | 64/16A/16A/2B4-CD3ç | | 20 |
| rCD64#13 | 64/16A/16A/2B4-FcRγ | | 21 |
| rCD64#14 | 64/16A/16A/2B4-Dap10 | | 22 |
| rCD64#15 | 64/16A/16A/2B4-Dap12 | | 23 |
| rCD64#16 | 64/64/64/2B4-CD3ç | | 24 |

*EC: Extracellular domain;
TM: Transmembrane domain;
CY: Cytoplasmic domain;
SD: Signaling domain.
64: CD64, High affinity IgG Fc receptor FcγRI;
mutCD64: High affinity IgG Fc receptor FcγR1 with cytoplasmic mutation that results in higher levels of cytokine production and degranulation;
16A, C16A, Low affinity IgG Fc receptor FcγRIIIA;
—: no signaling domain;
28: CD28, a co-stimulatory receptor for cell proliferation and activation;
BB: 4.1BB or CD137;
CD3ç: CD3 ç-chain or CD247;
FcRγ: FcR γ-chain;
D10: DAP10 signaling adaptor;
D12: DAP12 signaling adaptor;
FceR: High affinity IgE Fc receptor;
16-PKC⁻: CD16A cytoplasmic domain with mutations on PKC phosphorylation site to disrupt cytokine productions mediated by CD16A;
G2D: NKG2D or CD314;
2B4: NKR2B4 or CD244.

The CD64/16A chimeric receptor can be encoded by a cDNA that can be transcribed and translated from an expression vector introduced into a host cell to produce a recombinant cell. The host cell can include a suitable leukocyte-like cell or a primary leukocyte. Suitable leukocyte-like cells include, but are not limited to, a hematopoietic cell line or an induced pluripotent stem cell. Suitable primary leukocytes include, but are not limited to, NK cells, monocytes, macrophages, neutrophils, or T lymphocytes. The expression of CD64/16A by genetically-engineered leukocytes can increase the recombinant cell's effector function in killing target cells—e.g., tumor cells and virus-infected cells—in the presence of natural and therapeutic antibodies compared to the unmodified host cell. Because the CD64/16A chimeric receptor binds to IgG with high affinity, it may also be feasible to attach therapeutic mAbs to effector cells expressing the construct prior to their administration into patients. Hence, CD64/16A with an attached therapeutic mAb would provide the effector cells with a targeting element to direct them to cancer locations.

Figure 3:
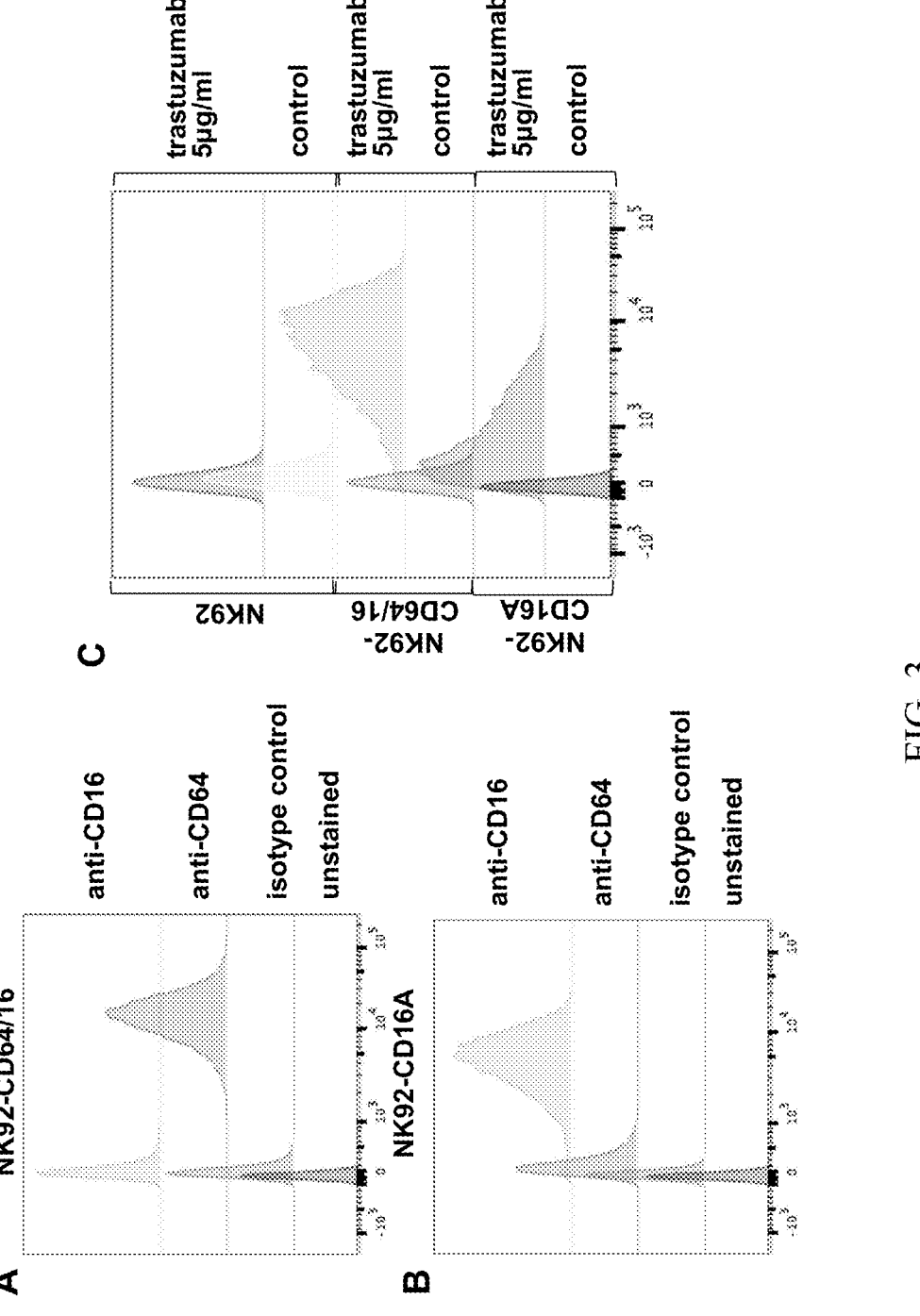
FIG. 3. NK92 cells expressing either wildtype CD16A or CD64/16A. (A) NK92-CD64/16A cells were stained with anti-CD16, anti-CD64, or control antibodies. (B) NK92-CD16A cells were stained with anti-CD16, anti-CD64, or control antibodies. (C) NK92-CD64/16A, NK92-CD16A, or NK92 parent cells were incubated with trastuzumab then anti-human IgG-APC second stage antibody or anti-human IgG-APC second stage antibody alone (control). All antibody staining levels were determined by flow cytometry.

NK92 cells are a human NK cell line that lacks expression of endogenous CD16A. NK cells were generated that express in a stable manner wildtype CD16A, wildtype CD64, or the exemplary chimeric receptor CD64/16A. NK92 cells expressing CD64/16A could be stained with an anti-CD64 mAb, but not with an anti-CD16 mAb (FIG. 3A). NK92-CD16A cells could be stained with an anti-CD16 mAb, but not with an anti-CD64 mAb (FIG. 3B). NK92 cells expressing CD64 could be stained with an anti-CD64 mAb, but not by and isotype-matched negative control mAb (FIG. 20A).

FIG. 3C shows the ability of NK92 cells expressing CD64/16A or CD16A to bind trastuzumab, a therapeutic mAb specific to HER2/EGFR2 overexpressed by certain malignancies. Non-transduced NK92 cells, NK92-CD64/16A cells, and NK92-CD16A cells were incubated with trastuzumab (5 µg/ml) for two hours at room temperature, washed to remove unbound antibody, incubated with an anti-human IgG second stage antibody conjugated to a fluorophore, and then examined by flow cytometry. NK92-hCD64/16A cells bound much higher levels of trastuzumab than did NK92-CD16A cells and NK92 cells.

FIG. 4 presents data that shows the exemplary chimeric receptor CD64/16A conferred NK92 cells with an ADCC effector function. NK92 cells expressing CD64/16A or wild-type CD16A were incubated with the human ovarian cancer cell line SKOV-3 (20:1 ratio) in the presence or absence of trastuzumab at various concentrations (0.005 µg/ml, 0.05 µg/ml. 0.5 µg/ml, or 5 µg/ml). NK92 cells expressing either CD64/16A or wildtype CD16A demonstrated SKOV-3 cytotoxicity in the presence of trastuzumab. NK92 cells expressing CD64/16A had higher levels of target cell killing than did NK92-CD16A cells at all trastuzumab concentrations examined (FIG. 4A). NK92 cells expressing either CD64 also demonstrated SKOV-3 cytotoxicity in the presence of trastuzumab (FIG. 20B). In addition, NK92-CD64/16A and NK92-CD16A cells were pretreated with trastuzumab at 5 µg/ml or 10 µg/ml for two hours, washed to remove unbound antibody, and then incubated with SKOV-3 cells. In this assay, NK92-CD64/16A cells demonstrated a marked enhancement in target cell killing when compared to NK92-CD16A cells (FIG. 4B).

Figure 5:
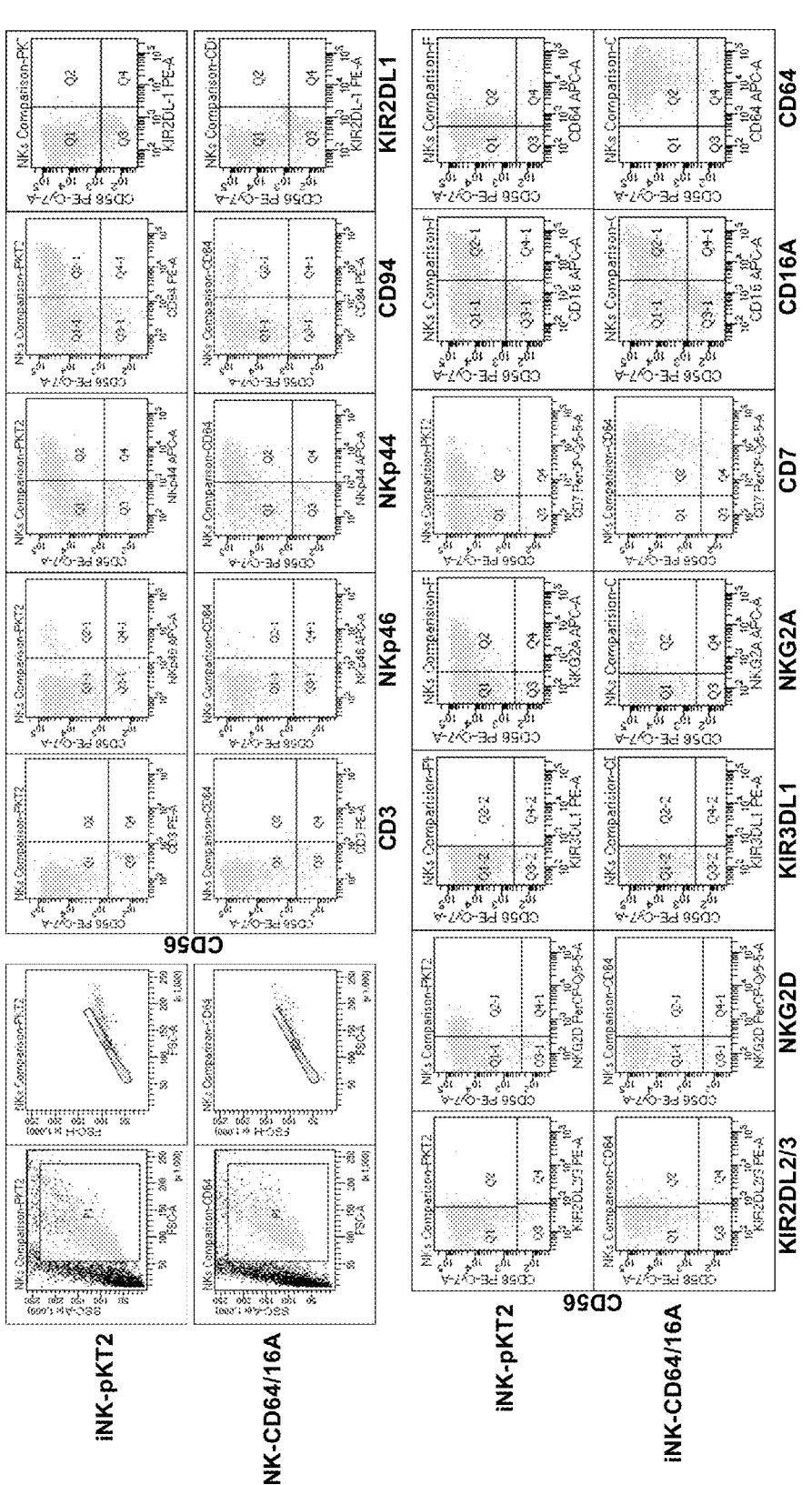
FIG. 5. Flow cytometry data comparing phenotypic markers expressed by iNK-CD64/CD16A and iNK-pKT2 cells.

CD64/16A also was expressed in iPSCs and these cells were then differentiated into NK cells (referred to here as iNK cells). As shown in FIG. 5, iNK cells transduced with either CD64/16A or the empty vector (pKT2) as a control were compared for their expression of several NK cell markers. iNK-CD64/16A and iNK-pKT2 cells are CD56 and CD3, indicating that they are indeed NK cells. They also expressed similar levels of various NK cell markers. iNK-CD64/16A and iNK-pKT2 cells were found to express similar levels of CD16A, whereas only iNK-CD64/16A were stained by an anti-CD64 mAb (FIG. 5).

Figure 6:
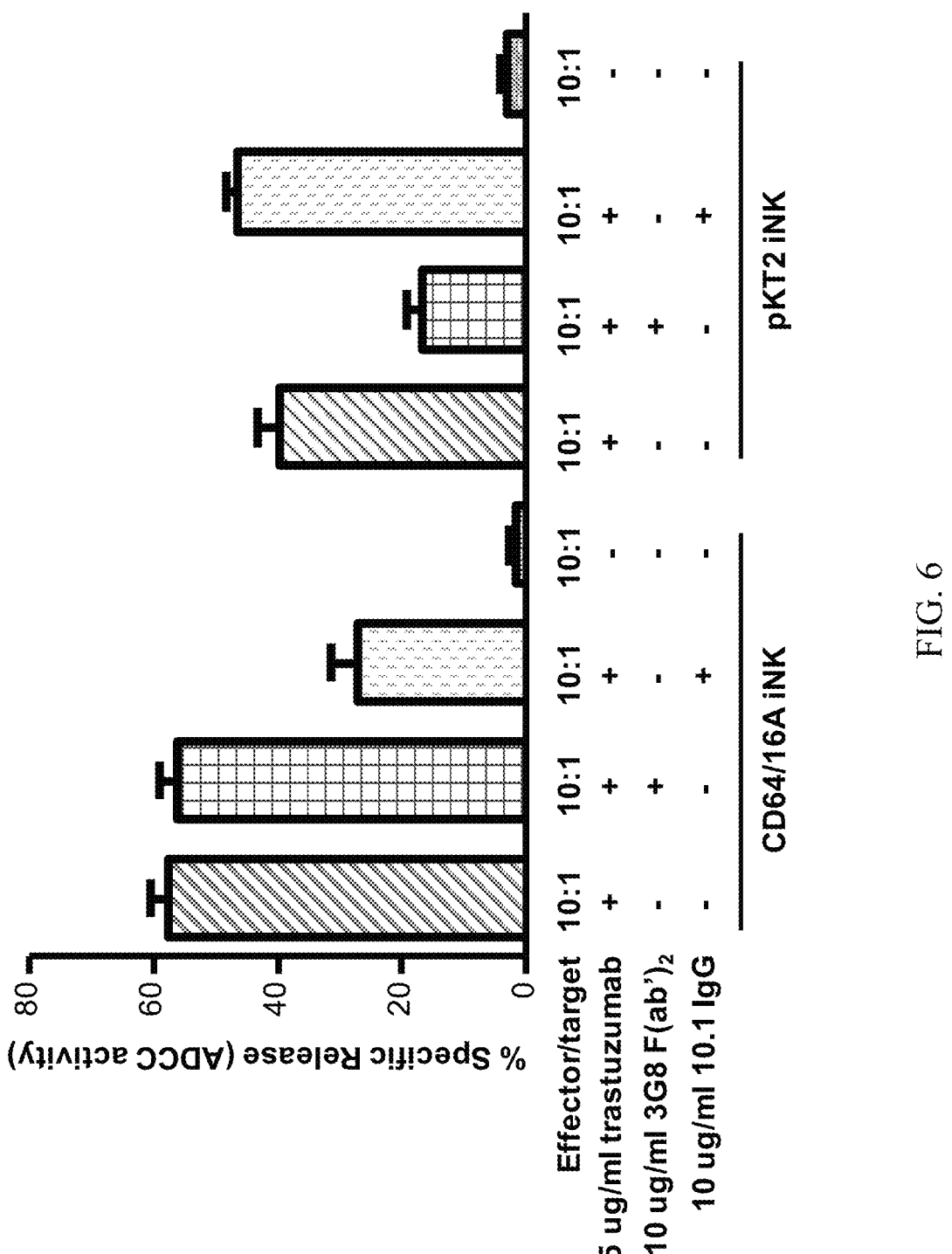
FIG. 6. Bar graph with data showing iNK-CD64/CD16A cells induce higher levels of ADCC than iNK-CD16A cells using SKOV-3 target cells.

INK-CD64/16A and iNK-pKT2 cells were evaluated for ADCC, as described above for the NK92 cells. iNK-CD64/16A and iNK-pKT2 cells were incubated with SKOV-3 cells at 10:1 ratio in the presence or absence of trastuzumab (5 µg/ml). iNK-CD64/16A cells demonstrated increased SKOV-3 cytotoxicity in the presence of trastuzumab and higher levels of ADCC when compared to iNK-pKT2 cells (FIG. 6).

Figure 7:
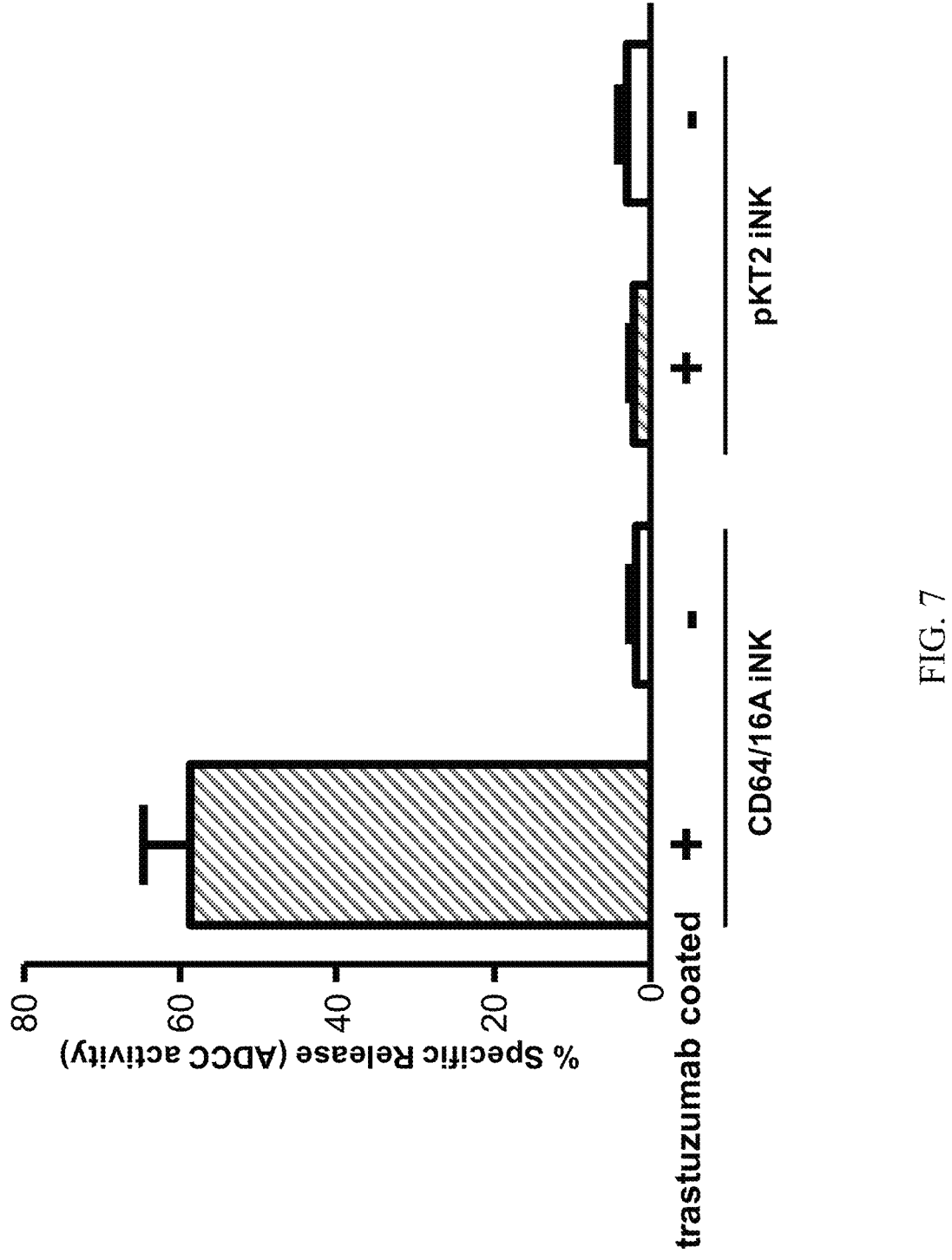
FIG. 7. Bar graph with data showing iNK-CD64/CD16A, but not iNK-CD16A cells can be pre-loaded with a therapeutic mAb and mediate ADCC.
Figure 8:
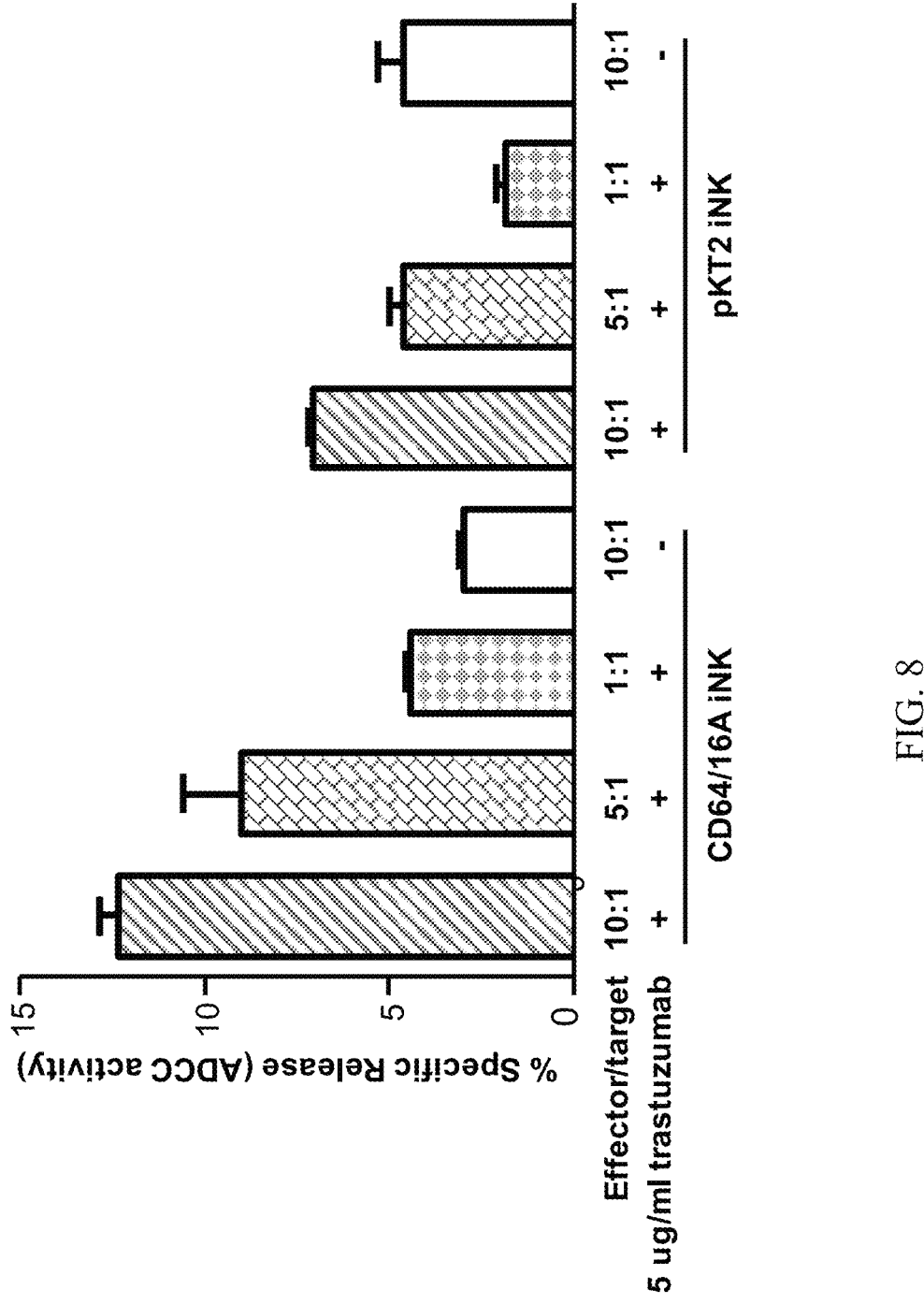
FIG. 8. Bar graph with data showing iNK-CD64/CD16A cells induce higher levels of ADCC than iNK-CD16A cells using MA148 target cells.

Although the iNK-CD64/16A and iNK-pKT2 cells expressed similar levels of CD16A (FIG. 5), the function blocking anti-CD16 mAb 3G8 only blocked ADCC by the iNK-pKT2 cells (FIG. 6). Conversely, the function blocking anti-CD64 mAb 10.1 only blocked ADCC by the iNK-CD64/16A cells (FIG. 6). INK-CD64/16A and iNK-pKT2 cells were also pretreated with trastuzumab at 10 µg/ml for two hours, washed to remove unbound antibody, and then incubated with SKOV-3 cells. In this assay, iNK-CD64/16A cells demonstrated a distinct enhancement in target cell killing when compared to iNK-pKT2 cells (FIG. 7). MA148 is a human ovarian cancer cell line that expresses considerably lower levels of HER2 when compared to SKOV-3 cells. ADCC was evaluated in iNK-CD64/16A and iNK-pKT2 cells when exposed to MA148 cells at various ratios in the presence or absence of trastuzumab (5 µg/ml). Again, iNK-CD64/16A cells demonstrated significantly higher levels of tumor cell killing than did iNK-pKT2 cells at all effector to target cell ratios when in the presence of trastuzumab (FIG. 8).

The chimeric receptor CD64/16A (FIG. 2; FIG. 13A) was stably expressed in the human NK cell line NK92. These cells lack endogenous FcγRs but transduced cells expressing exogenous CD16A can mediate ADCC. As shown in FIG. 13B, an anti-CD64 mAb stained NK92 cells expressing CD64/16A cells, but not parent NK92 cells or NK92 cells expressing CD16A. An anti-CD16 mAb stained NK92 cells expressing CD16A, but not NK92 cells expressing CD64/16A or parent NK92 cells (FIG. 13B). CD16A undergoes ectodomain shedding by ADAM17 upon NK cell activation resulting in its rapid downregulation in expression. CD16A and its isoform CD16B on neutrophils is cleaved by ADAM17, and this occurs at an extracellular region proximal to the cell membrane. The ADAM17 cleavage region of CD16A is not present in CD64 or CD64/16A (FIG. 13A). CD16A underwent a >50% decrease in expression upon NK92 stimulation by ADCC, whereas CD64/16A demonstrated little to no downregulation (FIG. 13C).

Figure 14:
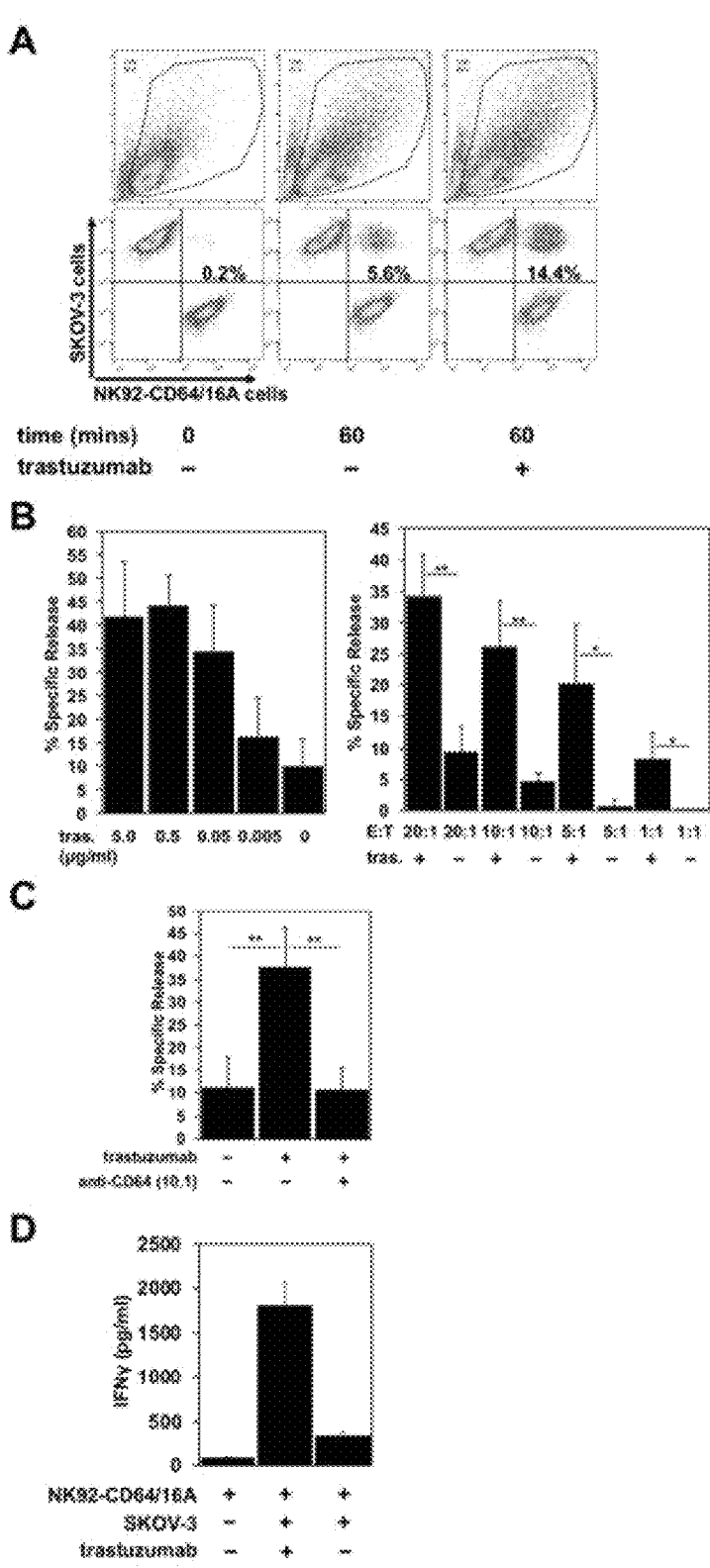
FIG. 14. CD64/16A promotes target cell conjugation, ADCC, and IFNγ production. (A) NK92-CD64/16A cells expressing eGFP and SKOV-3 cells labeled CellTrace Violet were mixed at an E:T ratio of 1:2 with or without trastuzumab (5 μg/ml), incubated at 37° C. for 60 minutes, fixed, and then analyzed by flow cytometry. Representative data from at least three independent experiments are shown. (B) NK92-CD64/16A cells were incubated with SKOV-3 cells (E:T=20:1) and trastuzumab (tras.) at the indicated concentrations (left panel), or with SKOV-3 cells at the indicated E:T ratios in the presence or absence of trastuzumab (5 μg/ml) (right panel) for two hours at 37° C. Data are represented as % specific release and the mean±SD of three independent experiments is shown. Statistical significance is indicated as *p<0.05,  p<0.01. (C) NK92-CD64/16A cells were incubated with SKOV-3 cells (E:T=20:1) in the presence or absence of trastuzumab (5 μg/ml) and the anti-CD64 mAb 10.1 (10 μg/ml), as indicated, for two hours at 37° C. Data are represented as % specific release and the mean±SD of three independent experiments is shown. Statistical significance is indicated as  p<0.01. (D) NK92-CD64/16A cells were incubated with SKOV-3 cells (E:T=1:1) with or without trastuzumab (5 μg/ml) for two hours at 37° C. Secreted IFNγ levels were quantified by ELISA. Data is shown as mean of two independent experiments.

To evaluate the function of CD64/16A, the ability of CD64/16A to initiate E:T conjugation, induce ADCC, and stimulate cytokine production upon NK cell engagement of antibody-bound tumor cells was examined. Prior to the release of its granule contents, an NK cell forms a stable conjugate with a target cell. NK92-CD64/16A cell and SKOV-3 cell conjugation were examined using a two-color flow cytometric approach. SKOV-3 cells are an ovarian cancer cell line that express HER2, and this assay was performed in the absence and presence of the anti-HER2 therapeutic mAb trastuzumab. The bicistronic vector containing CD64/16A also expressed eGFP and its fluorescence was used to identify the NK92 cells. SKOV-3 cells were labeled with the fluorescent dye CellTrace Violet. E:T conjugation resulted in two-color events that were evaluated by flow cytometry. Incubating NK92-CD64/16A cells with SKOV-3 cells resulted in a very low level of conjugation after initial exposure that increased after 60 minutes of exposure (FIG. 14A). However, in the presence of trastuzumab, NK92-CD64/16A cell and SKOV-3 conjugation was appreciably enhanced (FIG. 14A). This increase in conjugation corresponded with higher levels of target cell killing. As shown in FIG. 14B, SKOV-3 cell cytotoxicity by NK92-CD64/16A cells varied depending on the trastuzumab concentration and E:T ratio. To confirm the role of CD64/16A in the induction of target cell killing, the ADCC assay was performed in the presence and absence of the anti-CD64 mAb 10.1 (FIG. 14C), which blocks IgG binding. Cytokine production is also induced during ADCC and NK cells are major producers of IFNγ. NK92-CD64/16A cells exposed to SKOV-3 cells and trastuzumab produced considerably higher levels of IFNγ than when exposed to SKOV-3 cells alone (FIG. 14D). Taken together, the above findings demonstrate that the CD64 component of the recombinant receptor engages tumor-bound antibody, and that the CD16A component promotes intracellular signaling leading to degranulation and cytokine production.

Figure 15:
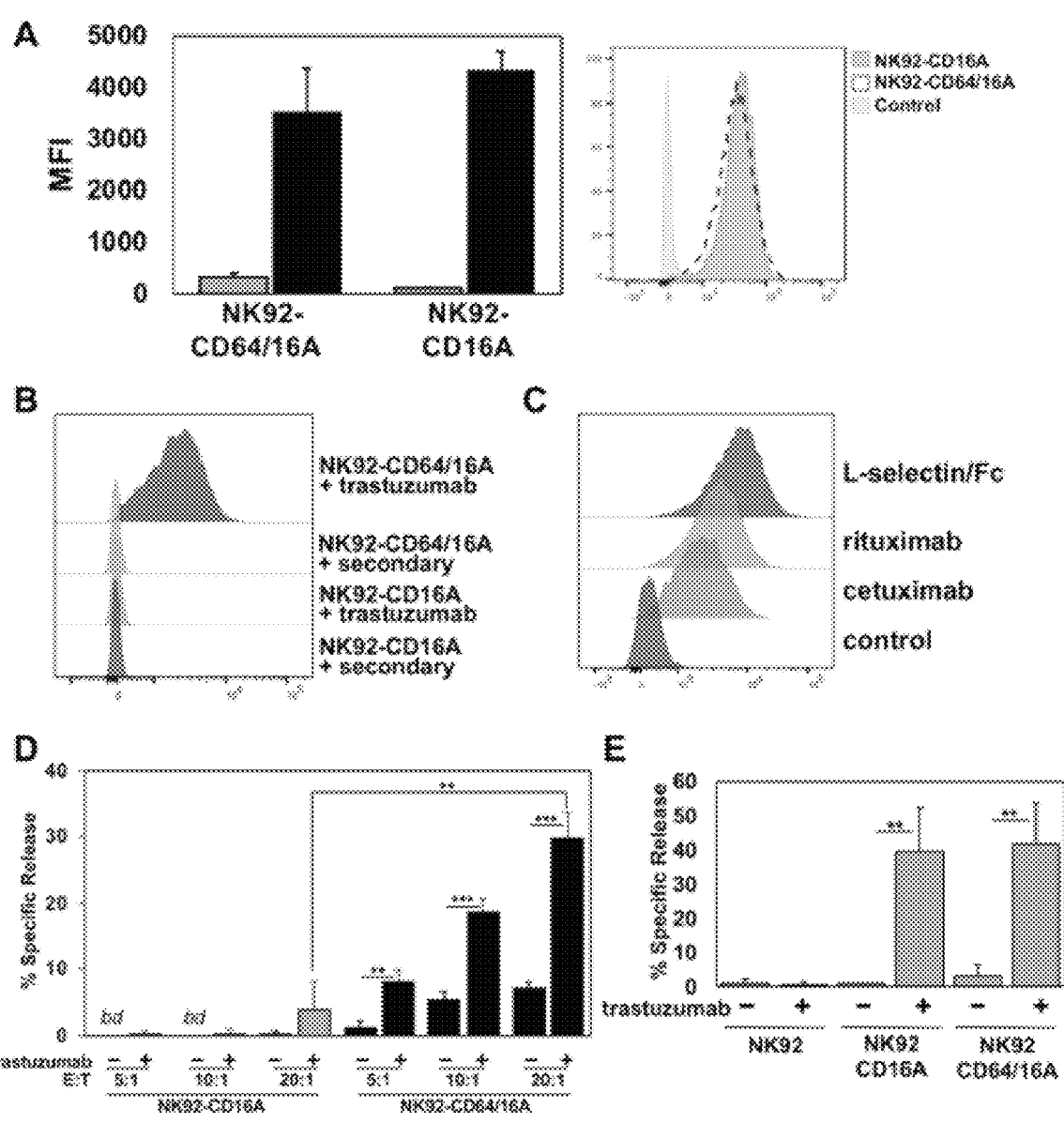
FIG. 15. CD64/16A attaches to soluble tumor-targeting mAbs and IgG fusion proteins. (A) Relative expression levels of CD16A and CD64/16A on NK92 cells were determined by cell staining with anti-CD16 and anti-CD64 mAbs (black bars), respectively, or an isotype-matched negative control antibody (gray bars). The bar graph shows mean fluorescence intensity (MFI)±SD of three independent experiments. Representative flow cytometric data are shown in the histogram overlay. In the right panel the dashed line histogram shows CD64 staining of NK92-CD64/16A cells, the right shaded histogram shows CD16A staining of NK92-CD16A cells, and the green-filled left shaded histogram shows isotype control antibody staining of the NK92-CD16A cells. (B) NK92-CD16A and NK92-CD64/16A cells were incubated with or without trastuzumab (5 μg/ml) for two hours at 37° C., washed, stained with a fluorophore-conjugated anti-human secondary antibody, and analyzed by flow cytometry. Data is representative of at least three independent experiments. (C) NK92-CD64/16A cells were incubated with cetuximab or rituximab (5 μg/ml for each), washed, and then stained with a fluorophore-conjugated anti-human secondary antibody. Control represents cells stained with the anti-human secondary antibody only. NK92-CD64/16A cells were also incubated with L-selectin/Fc (5 μg/ml), washed, and then stained with a fluorophore-conjugated anti-L-selectin mAb. NK92 cells lack expression of endogenous L-selectin (data not shown). All staining was analyzed by flow cytometry. Data shown are representative of three independent experiments. (D) NK92-CD16A and NK92-CD64/16A cells were incubated in the presence or absence of trastuzumab (5 μg/ml), washed, and exposed to SKOV-3 cells at the indicated E:T cell ratios for two hours at 37° C. Data is shown as mean±SD of three independent experiments. Statistical significance is indicated as  p<0.01, * p<0.001. bd=below detection, (i.e., <spontaneous release by negative control cells). (E) NK92-CD16A and NK92-CD64/16A cells were incubated with SKOV-3 cells (E:T=10:1) in the presence or absence of trastuzumab (5 μg/ml), as indicated, for two hours at 37° C. Data is shown as mean±SD of three independent experiments. Statistical significance is indicated as ** p<0.01.

CD64 is distinguished from the other FcγR members by its unique third extracellular domain, which contributes to its high affinity and stable binding to soluble monomeric IgG. NK92 cells expressing CD64/16A or the CD16A-176V higher affinity variant were compared for their ability to capture soluble therapeutic mAbs. The NK92 cell transductants examined expressed similar levels of CD64/16A and CD16A (FIG. 15A). NK92 cell transductants were incubated with trastuzumab for two hours, excess antibody was washed away, stained with a fluorophore-conjugated anti-human IgG antibody, and then evaluated by flow cytometry. As shown in FIG. 15B, NK92-CD64/16A cells captured considerably higher levels of trastuzumab than did the NK92-CD16A cells (8.1 fold increase ±1.3, mean±SD of three independent experiments). Moreover, the NK92-CD64/16A cells efficiently captured the tumor-targeting mAbs cetuximab and rituximab, as well as the fusion protein L-selectin/Fc (FIG. 15C).

NK92-CD64/16A cells with a captured tumor-targeting mAb were tested to determine whether the cells mediated ADCC. For this assay, equal numbers of NK92-CD64/16A and NK92-CD16A cells were incubated with the same concentration of soluble trastuzumab, washed, and exposed to SKOV-3 cells. Target cell killing by NK92-CD64/16A cells with captured trastuzumab was significantly higher than NK92-CD64/16A cells alone, and was superior to NK92-CD16A cells treated with or without trastuzumab at all E:T ratios examined (FIG. 15D). In contrast, SKOV-3 cytotoxicity by NK92-CD16A and NK92-CD64/16A cells was not significantly different when trastuzumab was present and not washed out (FIG. 15E), thus demonstrating equivalent cytotoxicity by both transductants. Taken together, these findings show that NK92 cells expressing CD64/16A can stably bind soluble anti-tumor mAbs and IgG fusion proteins, and that these can serve as targeting elements to kill cancer cells.

Expression and Function of CD64/16A in iPSC-Derived NK Cells

Figure 16:
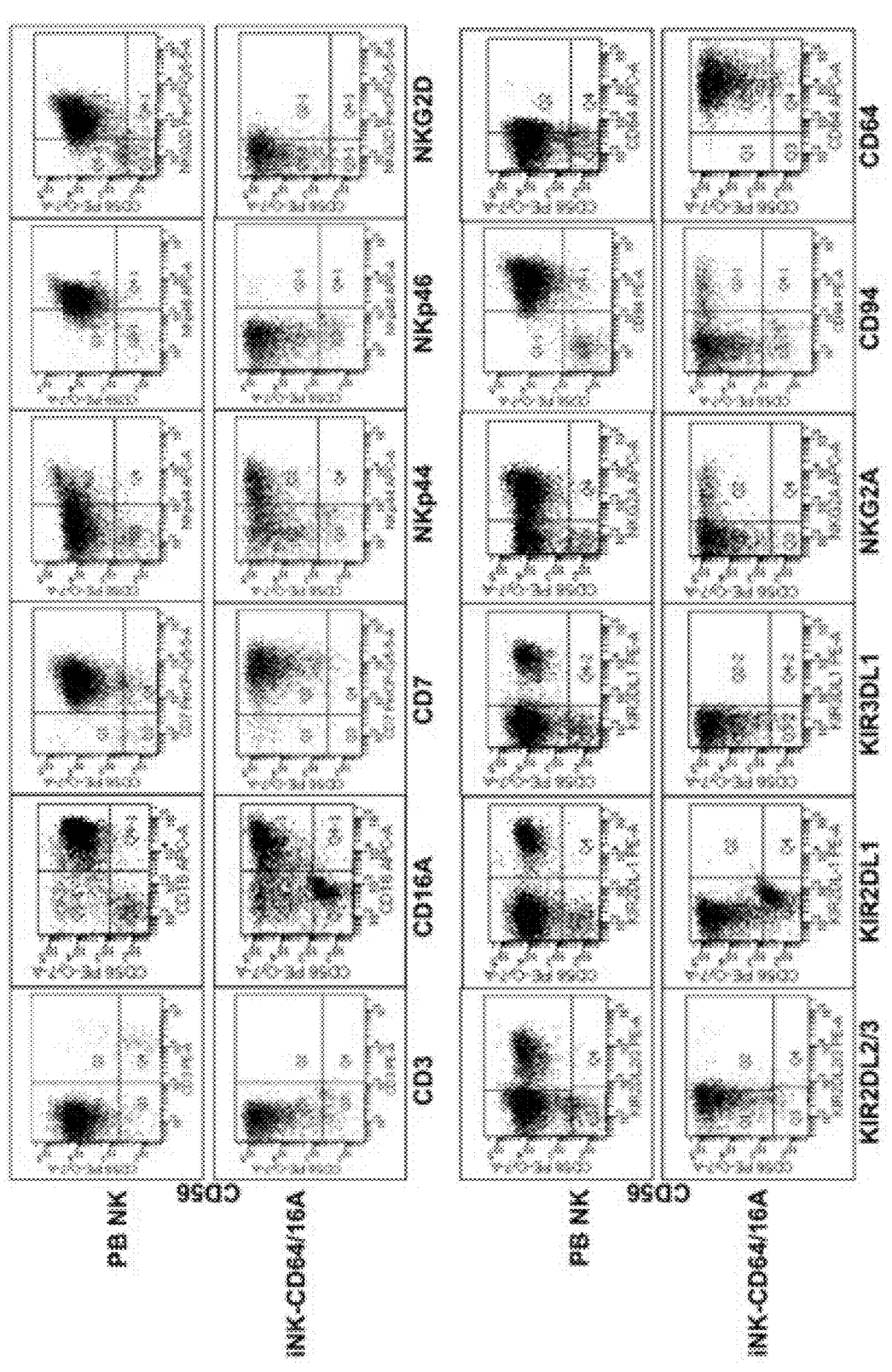
FIG. 16. Generation of iNK cells expressing CD64/CD16A. iPSCs were transduced to stably express CD64/16A, differentiated into NK cells, and then expanded using K562-mbIL21-41BBL feeder cells. iNK-CD64/16A cells and freshly isolated peripheral blood (PB) NK cells enriched from adult peripheral blood were stained for CD56, CD3 and various inhibitory and activating receptors, as indicated. CD64/16A expression was determined by staining the cells with an anti-CD64 mAb. Representative data from at least three independent experiments are shown.

Undifferentiated iPSCs were transduced to express CD64/16A using a Sleeping Beauty transposon plasmid for non-random gene insertion and stable expression. iPSCs were differentiated into hematopoietic cells and then iNK cells as described in the EXAMPLE 2. CD34 CD43 CD45 cells were generated, further differentiated into iNK cells, and these cells were expanded for analysis using recombinant IL-2 and aAPCs. CD56⁺ CD3⁻ is a hallmark phenotype of human NK cells, and these cells composed the majority of our differentiated cell population (FIG. 16). Expression of activating and inhibitory receptors on the iNK cells also were assessed and compared to expression by peripheral blood NK cells. Certain receptors, such as CD16A, were expressed by similar proportions of the two NK cell populations. The expanded iNK cells, however, lacked expression of the inhibitory KIR receptors KIR2DL2/3, KIR2DL1, and KIR3DL1 and also certain activating receptors (NKp46 and NKG2D) (FIG. 16). Another difference compared to peripheral blood NK cells was that the iNK cells were stained with an anti-CD64 mAb (FIG. 16), demonstrating the expression of CD64/16A.

To assess the function of CD64/16A in iNK cells, iNK cells derived from iPSCs transduced with either an pKT2 empty vector or pKT2-CD64/16A were compared. The NK cell markers mentioned above were expressed at similar levels and proportions by two iNK cell populations (data not shown), including CD16A (FIG. 17A), but only iNK-CD64/16A cells were stained by an anti-CD64 mAb (FIG. 17A). Both iNK tranductants demonstrated increased SKOV-3 cell killing when in the presence of trastuzumab, yet iNK-CD64/16A cells mediated significantly higher levels of ADCC than did the iNK-pKT2 control cells (FIG. 17B). The anti-CD16 function blocking mAb 3G8, but not the anti-CD64 mAb 10.1, effectively inhibited ADCC by the iNK-pKT2 cells (FIG. 17B). Conversely, 10.1, but not 3G8, blocked ADCC by the iNK-CD64/16A cells (FIG. 17B). These findings show that the iNK cells were cytolytic effectors responsive to CD16A and CD64/16A engagement of antibody-bound tumor cells.

Also, iNK-CD64/16A and iNK-pKT2 cells were treated with soluble trastuzumab, excess antibody was washed away, and the cells were exposed to SKOV-3 cells. Under these conditions, ADCC by the iNK-CD64/16A cells was strikingly higher than the iNK-pKT2 cells (FIG. 17C), further establishing that CD64/16A can capture soluble anti-tumor mAbs that serve as a targeting element for tumor cell killing.

Taken together, the data show that CD64/16A binds therapeutic mAbs with higher affinity than CD16A. Moreover, CD64/16A expressed in NK92 cells and iNK cells confers cells with the ability to mediate higher levels of ADCC than NK92 cells and iNK cells expressing wildtype or endogenous CD16A, respectively. NK cells expressing CD64/16A facilitated cell conjugation with antibody-bound tumor cells, cytotoxicity, and IFNγ production, demonstrating function by both components of the recombinant FcγR. NK92 cells and iNK cells expressing CD64/16A can be pre-loaded with a therapeutic mAb prior to their exposure to target cells. Cells expressing the chimeric receptor and preloaded with therapeutic antibody may allow one to modify engineered NK cells with different therapeutic mAbs for targeting elements of multiple types of cancer. Finally, CD64/16A lacks the ADAM17 cleavage region found in CD16A and it did not undergo the same level of downregulation in expression during ADCC.

CD64/16A was shown to be functional in two NK cell platforms, the NK92 cell line and primary NK cells derived from iPSCs. NK92 cells lack inhibitory KIR receptors and show high levels of natural cytotoxicity compared to other NK cell lines derived from patients. NK92 cells have been broadly used to express modified genes to direct their cytolytic effector function, have been evaluated in preclinical studies, and are undergoing clinical testing in cancer patients. iPSCs are also very amendable to genetic engineering and can be differentiated into NK cells expressing various receptors to direct their effector functions. The iNK cells generated in this study lacked several inhibitory and activating receptors that are indicators of an immature state. In some applications, therapeutic iNK cells lacking inhibitory receptors and certain activating receptors may allow for more directed and/or effective tumor cell killing by engineered receptors.

The iNK cells expressed endogenous CD16A and mediated ADCC, thus they were cytotoxic effector cells. An individual NK cell can kill multiple tumor cells in different manners. This includes by a process of sequential contacts and degranulations, referred to as serial killing, and by the localized dispersion of its granule contents that kills surrounding tumor cells, referred to as bystander killing. Inhibiting CD16A shedding has been reported to slow NK cell detachment from target cells and reduce serial killing by NK cells in vitro. Due to the CD64 component and its lack of ectodomain shedding, NK cells expressing CD64/16A could be less efficient at serial killing and more efficient at bystander killing.

NK cells expressing CD64/16A have several potential advantages as a therapeutic in combination with a therapeutic antibody. Modifying NK cells expressing CD64/16A with an antibody can reduce the dosage of therapeutic antibodies administered to patients. Fusion proteins containing a human IgG Fc region, such as L-selectin/Fc, also can be captured by CD64/16A and this may provide further options for directing the tissue and tumor antigen targeting of engineered NK cells. The NK92 and iNK cell platforms for adoptive cell therapies also can be readily genetically modified on a clonal level and expanded into clinical-scalable cell numbers to produce engineered NK cells with improved effector activities as an off-the-shelf therapeutic for cancer immunotherapy.

In some embodiments, iPSC-derived NK cells that express CD64/16A can exhibit increased in vivo anti-cancer activity in the presence of therapeutic mAbs. For example, NOD/SCID/γc$^{-/-}$ (NSG) mice and human cancer cell lines that are stably engineered to express firefly luciferase can be used for bioluminescent imaging to test iNK cell activity against cancer cells. The SKOV-3 and MA148 ovarian cancer cell line cans serve as model in vivo targets. NSG female mice can be subjected to sublethal irradiation, then injected intraperitoneally with tumor cells for bioluminescent imaging to quantify tumor growth or regression. Mice are given IL-2 and/or IL-15 every other day for four weeks to promote in vivo survival of the NK cells. Therapeutic antibody (e.g., trastuzumab) can be administered—e.g., once weekly for four weeks. Tumor growth/regression can be monitored by, for example, bioluminescent imaging and weighing the mice. Mice also can be bled (e.g., weekly) to quantify human NK cell survival, and one can further evaluate the expression/cell surface levels of various effector function markers by FACS. Evidence of metastasis can be determined by, for example, harvesting internal organs and examining the internal organs for metastasis.

In some embodiments, the number of cells in the therapeutic composition is at least 0.1 ×10$^5$ cells, at least 1×10$^5$ cells, at least 5×10$^5$ cells, at least 1×10$^6$ cells, at least 5×10$^6$ cells, at least 1×10$^7$ cells, at least 5×10$^7$ cells, at least 1×10$^8$ cells, at least 5×10$^8$ cells, at least 1×10$^9$ cells, or at least 5×10$^9$ cells, per dose. In some embodiments, the number of cells in the therapeutic composition is about 0.1×10$^5$ cells to about 1×10$^6$ cells, per dose; about 0.5×10$^6$ cells to about 1×10$^7$ cells, per dose; about 0.5×10$^7$ cells to about 1×10$^8$ cells, per dose; about 0.5×10$^8$ cells to about 1×10$^9$ cells, per dose; about 1×10$^9$ cells to about 5×10$^9$ cells, per dose; about 0.5×10$^9$ cells to about 8×10$^9$ cells, per dose; about 3×10$^9$ cells to about 3×10$^{10}$ cells, per dose, or any range in-between. Generally, 1×10$^8$ cells/dose translates to 1.67×10$^6$ cells/kg for a 60 kg patient.

In one embodiment, the number of cells in the therapeutic composition is the number of immune cells in a partial or single cord of blood, or is at least 0.1×10$^5$ cells/kg of bodyweight, at least 0.5×10$^5$ cells/kg of bodyweight, at least 1×10$^5$ cells/kg of bodyweight, at least 5×10$^5$ cells/kg of bodyweight, at least 10×10$^5$ cells/kg of bodyweight, at least 0.75×10$^6$ cells/kg of bodyweight, at least 1.25×10$^6$ cells/kg of bodyweight, at least 1.5×10$^6$ cells/kg of bodyweight, at least 1.75×10$^6$ cells/kg of bodyweight, at least 2×10$^6$ cells/kg of bodyweight, at least 2.5 ×10$^6$ cells/kg of bodyweight, at least 3×10$^6$ cells/kg of bodyweight, at least 4×10$^6$ cells/kg of bodyweight, at least 5×10$^6$ cells/kg of bodyweight, at least 10×10$^6$ cells/kg of bodyweight, at least 15×10$^6$ cells/kg of bodyweight, at least 20×10$^6$ cells/kg of bodyweight, at least 25×10$^6$ cells/kg of bodyweight, at least 30×10$^6$ cells/kg of bodyweight, 1×10$^8$ cells/kg of bodyweight, 5×10$^8$ cells/kg of bodyweight, or 1×10$^9$ cells/kg of bodyweight.

In one embodiment, a dose of cells is delivered to a subject. In one illustrative embodiment, the effective amount of cells provided to a subject is at least 2×10$^6$ cells/kg, at least 3×10$^6$ cells/kg, at least 4×10$^6$cells/kg, at least 5×10$^6$ cells/kg, at least 6×10$^6$ cells/kg, at least 7×10$^6$ cells/kg, at least 8×10$^6$ cells/kg, at least 9×10$^6$ cells/kg, or at least 10 ×10$^6$ cells/kg, or more cells/kg, including all intervening doses of cells.

In another illustrative embodiment, the effective amount of cells provided to a subject is about 2×10$^6$ cells/kg, about 3×10$^6$ cells/kg, about 4×10$^6$cells/kg, about 5×10$^6$ cells/kg, about 6×10$^6$ cells/kg, about 7×10$^6$ cells/kg, about 8×10$^6$ cells/kg, about 9×10$^6$ cells/kg, or about 10 ×10$^6$ cells/kg, or more cells/kg, including all intervening doses of cells.

In another illustrative embodiment, the effective amount of cells provided to a subject is from about 2×10$^6$ cells/kg to about 10×10$^6$ cells/kg, about 3×10$^6$ cells/kg to about 10 ×10$^6$ cells/kg, about 4×10$^6$ cells/kg to about 10×10$^6$ cells/kg, about 5×10$^6$ cells/kg to about 10 ×10$^6$ cells/kg, 2×10$^6$ cells/kg to about 6×10$^6$ cells/kg, 2×10$^6$ cells/kg to about 7×10$^6$ cells/kg, 2 ×10$^6$ cells/kg to about 8×10$^6$ cells/kg, 3×10$^6$ cells/kg to about 6×10$^6$ cells/kg, 3×10$^6$ cells/kg to about 7×10$^6$ cells/kg, 3×10$^6$ cells/kg to about 8×10$^6$ cells/kg, 4×10$^6$ cells/kg to about 6 ×10$^6$ cells/kg, 4×10$^6$ cells/kg to about 7×10$^6$ cells/kg, 4×10$^6$ cells/kg to about 8×10$^6$ cells/kg, 5 ×10$^6$ cells/kg to about 6×10$^6$ cells/kg, 5×10$^6$ cells/kg to about 7×10$^6$ cells/kg, 5×10$^6$ cells/kg to about 8×10$^6$ cells/kg, or 6×10$^6$cells/kg to about 8×10$^6$ cells/kg, including all intervening doses of cells.

Some variation in dosage will necessarily occur depending on the condition of the subject being treated. The person responsible for administration will, in any event, determine the appropriate dose for the individual subject.

In some embodiments, the therapeutic use of cells is a single-dose treatment. In some embodiments, the therapeutic use of derived hematopoietic lineage cells is a multi-dose treatment. In some embodiments, the multi-dose treatment is one dose every day, every 3 days, every 7 days, every 10 days, every 15 days, every 20 days, every 25 days, every 30 days, every 35 days, every 40 days, every 45 days, or every 50 days, or any number of days in-between.

A compositions that includes a population of cells described herein can be sterile, and can be suitable and ready for administration (i.e., can be administered without any further processing) to human patients. A cell-based composition that is ready for administration means that the composition does not require any further processing or manipulation prior to transplant or administration to a subject. In some embodiments, such a population of cells can include an isolated population of cells that are expanded and/or modulated prior to administration with one or more agents.

In certain embodiments, the primary stimulatory signal and the co-stimulatory signal for the therapeutic cells can be provided by different protocols. For example, the agents providing each signal can be in solution or coupled to a surface. When coupled to a surface, the agents can be coupled to the same surface (i.e., in "cis" formation) or to separate surfaces (i.e., in "trans" formation). Alternatively, one agent can be coupled to a surface and the other agent in solution. In one embodiment, the agent providing the co-stimulatory signal can be bound to a cell surface and the agent providing the primary activation signal is in solution or coupled to a surface. In certain embodiments, both agents can be in solution. In another embodiment, the agents can be in soluble form, and then cross-linked to a surface, such as a cell expressing Fc receptors or an antibody or other binding agent that will bind to the agents such as disclosed in U.S. Patent Application Publication Nos. 20040101519 and 20060034810 for artificial antigen presenting cells (aAPCs) that are contemplated for use in activating and expanding T lymphocytes.

The therapeutic compositions suitable for administration to a patient can include one or more pharmaceutically acceptable carriers (additives) and/or diluents (e.g., pharmaceutically acceptable medium, for example, cell culture medium), or other pharmaceutically acceptable components. Pharmaceutically acceptable carriers and/or diluents are determined in part by the particular composition being administered, as well as by the particular method used to administer the therapeutic composition. Accordingly, there is a wide variety of suitable formulations of therapeutic compositions (see, e.g., Remington's Pharmaceutical Sciences, 17th ed. 1985, the disclosure of which is hereby incorporated by reference in its entirety) well known to those of skill in the art.

In particular embodiments, therapeutic cell compositions having an isolated population the cells as described herein also have a pharmaceutically acceptable cell culture medium, or pharmaceutically acceptable carriers and/or diluents. A therapeutic composition comprising a population of the cells as disclosed herein can be administered separately by intravenous, intraperitoneal, enteral, or tracheal administration methods or in combination with other suitable compounds to affect the desired treatment goals.

These pharmaceutically acceptable carriers and/or diluents can be present in amounts sufficient to maintain a pH of the therapeutic composition of between about 3 and about 10. As such, the buffering agent can be as much as about 5% on a weight to weight basis of the total composition. Electrolytes such as, but not limited to, sodium chloride and potassium chloride can also be included in the therapeutic composition. In one aspect, the pH of the therapeutic composition is in the range from about 4 to about 10. Alternatively, the pH of the therapeutic composition is in the range from about 5 to about 9, from about 6 to about 9, or from about 6.5 to about 8. In another embodiment, the therapeutic composition includes a buffer having a pH in one of said pH ranges. In another embodiment, the therapeutic composition has a pH of about 7.

Alternatively, the therapeutic composition has a pH in a range from about 6.8 to about 7.4. In still another embodiment, the therapeutic composition has a pH of about 7.4.

This disclosure also provides the use of a pharmaceutically acceptable cell culture medium in particular compositions and/or cultures of cells as described herein. Such compositions are suitable for administration to human subjects. Generally speaking, any medium that supports the maintenance, growth, and/or health of the iPSC-derived immune cells are suitable for use as a pharmaceutical cell culture medium. In particular embodiments, the pharmaceutically acceptable cell culture medium is a serum free, and/or feeder-free medium. In various embodiments, the serum-free medium is animal-free, and can optionally be protein-free. Optionally, the medium can contain biopharmaceutically acceptable recombinant proteins. Animal-free medium refers to medium wherein the components are derived from non-animal sources. Recombinant proteins replace native animal proteins in animal-free medium and the nutrients are obtained from synthetic, plant or microbial sources. Protein-free medium, in contrast, is defined as substantially free of protein. One having ordinary skill in the art would appreciate that the above examples of media are illustrative and in no way limit the formulation of suitable media suitable and that there are many alternative suitable media known and available to those in the art.

In the preceding description and following claims, the term "and/or" means one or all of the listed elements or a combination of any two or more of the listed elements; the terms "comprises," "comprising," and variations thereof are to be construed as open ended—i.e., additional elements or steps are optional and may or may not be present; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Example 1

Generation of Human CD64/16A Expression Constructs

Total RNA was isolated from peripheral blood leukocytes (PBL) using TRIzol total RNA isolation reagent (Invitrogen, Thermo Fisher Scientific, Carlsbad, CA). Human PBL cDNA was synthesized with the SuperScript Preamplification System (Invitrogen, Thermo Fisher Scientific, Carlsbad, CA). The CD64/16A includes a human CD64 extracellular domain (CD64-EC) and CD16A transmembrane and cytoplasmic domains (CD16A-TM-CY). The chimeric construct was generated by overlapping PCR to create EcoR I-flanked RT-PCR products of chimeric cDNA. CD64-EC cDNA fragment (885 bps) was amplified from human PBL cDNA using the forward primer 5'-CGG GAA TTC GGA GAC AAC ATG TGG TTC TTG ACA A-3' (SEQ ID NO: 28) and reverse primer 5'-TTG GTA CCC AGG TGG AAA GAA GCC AAG CAC TTG AAG CTC CAA-3'; SEQ ID NO:29). CD16A-TM-CY cDNA fragment (195 bps) was amplified from human PBL cDNA using the forward primer 5'-TTG GAG CTT CAA GTG CTT GGC TTC TTT CCA CCT GGG TAC CAA-3' (SEQ ID NO:30) and reverse primer 5'-CCG GAA TTC TCA TTT GTC TTG AGG GTC CTT TCT-3' (SEQ ID NO:31). The PCR fragments of CD64-EC cDNA and CD16A-TM-CY cDNA were purified with QIAquick gel extraction kit (Qiagen, Hilden, Germany) and mixed together with the forward primer 5'-CGG GAA TTC GGA GAC AAC ATG TGG TTC TTG ACA A-3' (SEQ ID NO:32) and the reverse primer 5'-CCG GAA TTC TCA TTT GTC TTG AGG GTC CTT TCT-3' (SEQ ID NO:33). For all primers listed above, underlined nucleotides are the EcoR I cutting site) to generate RT-PCR products for the chimeric receptor. RT-PCR was performed with Pfx50 DNA polymerase (Invitrogen, Thermo Fisher Scientific, Carlsbad, CA). The resultant CD64/CD16a cDNA was inserted into retrovirus expression vector pBMN-IRES-EGFP (Addgene, Cambridge, MA) and pKT2 Sleeping Beauty transposon vector (Jing et al. 2015. *PLoS One* 10:e0121788; Hermanson et al. 2016. *Stem Cells* 34:93-101). The sequences of all cloned constructs were confirmed by direct sequencing from both directions on an ABI 377 sequencer with ABI BigDye terminator cycle sequencing kit (Applied Biosystems, Thermo Fisher Scientific, Foster City, CA).

Stable Expression of CD64/16A in NK Cells

NK92 cells, a human NK cell line that is deficient for endogenous CD16A expression, were stably transduced with pBMN-IRES-EGFP retrovirus expression constructs containing CD64/16A or wildtype CD16A cDNA using retrovirus infection procedures described previously (Jing et al. 2015. *PLoS One* 10:e0121788). Human iPSCs (UCBiPS7, derived from umbilical cord blood CD34 cells) were stably transduced with the CD64/16A-pKT2 expression construct using a Sleeping Beauty transposon system, as previously described (Jing et al. 2015. *PLoS One* 10:e0121788). The transduced iPSC cells were differentiated into hematopoietic cells then mature NK cell as previously described (Jing et al. 2015. *PLoS One* 10:e0121788). eGFP fluorescence and surface expressions of CD64, CD16, and various NK cell phenotypic markers were determine using flow cytometry analysis.

Example 2

Antibodies

All mAbs to human hematopoietic and leukocyte phenotypic markers are described in Table 2. All isotype-matched negative control mAbs were purchased from BioLegend (San Diego, CA). APC-conjugated F(ab')2 donkey anti-human or goat anti-mouse IgG (H+L) were purchased from Jackson ImmunoResearch Laboratories (West Grove, PA). The human IgG1 mAbs trastuzumab/Herceptin and rituximab/Rituxan, manufactured by Genentech (South San Francisco, CA), and cetuximab/Erbitux, manufactured by Bristol-Myers Squibb (Lawrence, NJ), were purchased through the University of Minnesota Boynton Pharmacy. Recombinant human L-selectin/IgG1 Fc chimera was purchased from R&D Systems (Minneapolis, MN).

TABLE 2

| Antibodies | | | |
|---|---|---|---|
| Antigen | Clone | Fluorophore | Company |
| CD56 | HCD56 | PE-CY7 | BioLegend, San Diego, CA |
| CD3 | HIT3a | PE | BioLegend |
| CD16 | 3G8 | APC | BioLegend |
| CD16 | 3G8 | none | Ancell, Bayport, MN |
| CD7 | CD7-6B7 | PE/CY5 | BioLegend |

TABLE 2-continued

| | Antibodies | | |
|---|---|---|---|
| Antigen | Clone | Fluorophore | Company |
| CD336/NKp44 | P44-8 | APC | BioLegend |
| CD335/NKp46 | 9E2 | APC | BioLegend |
| CD159a/NKG2A | Z199 | APC | Beckman Coulter, Brea, CA |
| CD314/NKG2D | 1D11 | PerCP/Cy5.5 | BioLegend |
| CD158a/KIR2DL1 | HP-MA4 | PE | BioLegend |
| CD158b1/KIR2DL2/L3 | DX27 | PE | BioLegend |
| CD158e1/KIR3DL1 | DX9 | PE | BioLegend |
| CD94 | DX22 | PE | BioLegend |
| CD64 | 10.1 | APC | BioLegend |
| CD64 | 10.1 | none | Ancell |
| CD34 | 561 | PE | BioLegend |
| CD45 | 2D1 | APC | BioLegend |
| CD43 | CD43-10G7 | APC | BioLegend |
| CD62L/L-selectin | LAM1-116 | APC | Ancell |

Generation of Human CD64/16A

Total RNA was isolated from human peripheral blood leukocytes using TRIzol total RNA isolation reagent (Invitrogen, Carlsbad, CA) and cDNA was synthesized with the SuperScript preamplification system (Invitrogen, Carlsbad, CA). The recombinant CD64/16A is comprised of human CD64 extracellular domain and CD16A transmembrane and cytoplasmic domains. PCR fragments for CD64 (885 bps) and CD16A (195 bps) were amplified from the generated cDNA. The PCR fragments were purified and mixed together with the forward primer 5'-CGG GAA TTC GGA GAC AAC ATG TGG TTC TTG ACA A-3' (SEQ ID NO:28), the reverse primer 5'-CCG GAA TTC TCA TTT GTC TTG AGG GTC CTT TCT-3' (SEQ ID NO: 31), and Pfx50 DNA polymerase (Invitrogen) to generate the recombinant CD64/16A receptor. For both primers, underlined nucleotides are EcoR I sites. CD64/CD16A and CD16A cDNA (CD16A-176V variant) was inserted into the retroviral expression vector pBMN-IRES-EGFP and virus was generated for NK92 cell transduction, as previously described (Jing et al., 2015. PLoS One 10 (3):e0121788). Additionally, CD64/CD16A cDNA was inserted into the pKT2 sleeping beauty transposon vector and used along with SB 100× transposase for iPSC transduction, as previously described (Jing et al., 2015. PLoS One 10 (3): e0121788). The nucleotide sequences of all constructs were confirmed by direct sequencing from both directions on an ABI 377 sequencer with ABI BigDye terminator cycle sequencing kit (Applied Biosystems, Foster City, CA).

Cells

This study was carried out in accordance with and approved by the Institutional Review Board at the University of Minnesota. All subjects gave written informed consent in accordance with the Declaration of Helsinki. Fresh human peripheral blood leukocytes from plateletpheresis were obtained from Innovative Blood Resources (St. Paul, MN). Peripheral blood mononuclear cells were further enriched using Ficoll-Paque Plus (GE Healthcare Bio-Sciences AB, Uppsala, Sweden) and NK cells were purified by negative depletion using an EasySep human NK cell kit (StemCell Technologies, Cambridge, MA), as per the manufacturer's instructions, with >95% viability and 90-95% enrichment of CD56 CD3 lymphocytes. Viable cell counting was performed using a Countess II automated cell counter (Life Technologies Corporation, Bothell, WA). The human NK cell line NK92 and the ovarian cancer cell line SKOV-3 were obtained from ATCC (Manassas, VA) and cultured per the manufacturer's directions. The NK92 cells required IL-2 for growth (500 IU/ml), which was obtained from R&D Systems (Minneapolis, MN). For all assays described below, cells were used when in log growth phase.

The iPSCs UCBiPS7, derived from umbilical cord blood CD34 cells, have been previously characterized and were cultured and differentiated into hematopoietic progenitor cells as described with some modifications (Jing et al., 2015. PLoS One 10:e0121788; Ni et al., 2013. Methods in molecular biology 1029:33-41; Knorr et al., 2013. Stem Cells Transl Med 2 (4): 274-283; Ni et al., 2014. Stem Cells 32 (4): 1021-1031; Hermanson et al., 2016. Stem Cells 34 (1): 93-101). iPSCs culture and hematopoietic differentiation was performed using TeSR-E8 medium and a STEMdiff Hematopoietic Kit (StemCell Technologies, Cambridge, MA), which did not require the use of mouse embryonic fibroblast feeder cells, TrypLE adaption, spin embryoid body formation, or CD34 cell enrichment. iPSC cells during passage were dissociated with Gentle Cell Dissociation Reagent (StemCell Technologies, Cambridge, MA), and iPSC aggregates >50 µm in diameter were counted with a hemocytometer and diluted to 20-40 aggregates/ml with TeSR-E8 medium. Each well of a 12-well plate was pre-coated with Matrigel Matrix (Corning Inc., Tewksbury, MA) and seeded with 40-80 aggregates in 2 ml of TeSR-E8 medium. Cell aggregates were cultured for 24 hours before differentiation with the STEMdiff Hematopoietic Kit (Stem-Cell Technologies, Cambridge, MA) according to the manufacturer's instructions. At day 12 of hematopoietic progenitor cell differentiation, the percentage of hematopoietic progenitor cells was determined using flow cytometric analysis with anti-CD34, anti-CD45, and anti-CD43 mAbs. NK cell differentiation was performed as previously described (Woll et al., 2009. Blood 113 (24): 6094-6101). The iPSC-derived NK cells (referred to here as iNK cells) were expanded for examination using γ-irradiated K562-mbIL21-41BBL feeder cells (1:2 ratio) in cell expansion medium [60% DMEM, 30% Ham's F12, 10% human AB serum (Valley Biomedical, Winchester, VA), 20 M 2-mercaptoethanol, 50 µM ethanolamine, 20 µg/ml ascorbic Acid, 5 ng/ml sodium selenite, 10 mM HEPES, and 100-250 IU/ml IL-2 (R&D Systems)], as described previously (Jing et al., 2015. PLoS One 10:e0121788; Knorr et al., 2013. Stem Cells Transl Med 2 (4): 274-283; Ni et al., 2014. Stem Cells 32 (4): 1021-1031; Hermanson et al., 2016. Stem Cells 34 (1): 93-101).

Cell Staining, Flow Cytometry, and ELISA

For cell staining, nonspecific antibody binding sites were blocked and cells were stained with the indicated antibodies and examined by flow cytometry, as previously described (Romee et al, 2013. *Blood* 121 (18): 3599-3608; Jing et al., 2015. *PLoS One* 10:e0121788; Mishra et al., 2018. *Cancer Immunol Immunother* 67 (9): 1407-1416). For controls, fluorescence minus one was used as well as appropriate isotype-matched antibodies since the cells of interest expressed FcRs.

An FSC-A/SSC-A plot was used to set an electronic gate on leukocyte populations and an FSC-A/FSC-H plot was used to set an electronic gate on single cells. A Zombie viability kit was used to assess live vs. dead cells, as per the manufacturer's instructions (BioLegend, San Diego, CA).

To assess the capture of soluble trastuzumab, rituximab, cetuximab, or L-selectin/Fc chimera, transduced NK cells were incubated with 5 μg/ml of antibody for two hours at 37° C. in MEM-α basal media (Thermo Fisher Scientific, Waltham, MA) supplemented with IL-2 (200 IU/ml), HEPES (10 mM), and 2-mercaptoethanol (0.1 mM), washed with MEM-α basal media, and then stained on ice for 30 minutes with a 1:200 dilution of APC-conjugated F(ab')2 donkey anti-human IgG (H+L). To detect recombinant human L-selectin/Fc binding, cells were stained with the anti-L-selectin mAb APC-conjugated Lam1-116.

To compare CD16A, CD64, and CD64/16A staining levels on NK92 cells, the respective transductants were stained with a saturating concentration of unconjugated anti-CD16 (3G8) or anti-CD64 (10.1) mAbs (5 μg/ml), washed extensively with dPBS (USB Corporation, Cleveland, OH) containing 2% goat serum and 2 mM sodium azide, and then stained with APC-conjugated F(ab')2 goat anti-mouse IgG (H+L). This approach was used since directly conjugated anti-CD16 and anti-CD64 mAbs can vary in their levels of fluorophore labeling. ELISA was performed by a cytometric bead-based Flex Set assay for human IFNγ (BD Biosciences, San Jose, CA) per the manufacturer's instructions. All flow cytometric analyses were performed on a FACSCelesta instrument (BD Biosciences). Data was analyzed using FACSDIVA v8 (BD Biosciences) and FlowJo v10 (Ashland, OR).

Cell-cell conjugation assay and ADCC The pBMN-IRES-EGFP vector used to express CD64/16A in NK92 cells also expresses eGFP. These cells were incubated for two hours at 37° C. in MEM-α basal media (Thermo Fisher Scientific, Waltham, MA) supplemented with IL-2 (200 IU/ml), HEPES (10 mM), and 2-mercaptoethanol (0.1 mM). SKOV-3 cells were labeled with CellTrace Violet (Molecular Probes, Eugene, OR) per the manufacturer's instructions, incubated with 5 g/ml trastuzumab for 30 minutes and washed with the MEM-α basal media. NK92 cells and SKOV-3 cells were then resuspended in the supplemented MEM-α basal media at $1 \times 10^6$ and $2 \times 10^6$/ml, respectively. For a 1:2 E:T ratio, 100 μl of each cell type was mixed together, centrifuged for one minute at 20×g and incubated at 37° C. for the indicated time points. After each time point, the cells were gently vortexed for three seconds and immediately fixed with 4° C. 1% paraformaldehyde in dPBS. Samples were immediately analyzed by flow cytometry. The percentage of conjugated NK cells was calculated by gating on eGFP and CellTrace Violet double-positive events.

To evaluate ADCC, a DELFIA EuTDA-based cytotoxicity assay was used according to the manufacturer's instructions (PerkinElmer, Waltham, MA). Briefly, target cells were labeled with Bis (acetoxymethyl)-2-2:6,2 terpyridine 6,6 dicarboxylate (BATDA) for 30 minutes in their culture medium, washed in culture medium, and pipetted into a 96-well non-tissue culture-treated U-bottom plates at a density of $8 \times 10^4$ cells/well. A tumor targeting mAb was added at the indicated concentrations of 5 μg/mL and NK cells were added at the indicated effector:target (E:T) ratios. The plates were centrifuged at 400×g for one minute and then incubated for two hours in a humidified 5% $CO_2$ atmosphere at 37° C. At the end of the incubation, the plates were centrifuged at 500×g for five minutes and supernatants were transferred to a 96-well DELFIA Yellow Plate (PerkinElmer, Waltham, MA) and combined with europium. Fluorescence was measured by time-resolved fluorometry using a BMG Labtech CLARIOstar plate reader (Cary, NC). BATDA-labeled target cells alone with or without therapeutic antibodies were cultured in parallel to assess spontaneous lysis and in the presence of 2% Triton-X to measure maximum lysis. The level of ADCC for each sample was calculated using the formula: Percent Specific Release=(Experimental release counts-Spontaneous release counts)/(Maximal release-Spontaneous release counts)×100%. For each experiment, measurements were conducted in triplicate using three replicate wells.

Statistical Analyses

Statistical analyses were performed by use of GraphPad Prism (GraphPad Software, La Jolla, CA, USA). After assessing for approximate normal distribution, all variables were summarized as mean±SD. Comparison between two groups was done with Student's t-test, with p<0.05 taken as statistically significant.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

SEQUENCE LISTING FREE TEXT
rCD64#1 (pCDH-CD64) peptide sequence
                                    (SEQ ID NO: 9)
MWFLTTLLLW VPVDGQVDTT KAVITLQPPW VSVFQEETVT

LHCEVLHLPG SSSTQWFLNG TATQTSTPSY RITSASVNDS

GEYRCQRGLS GRSDPIQLEI HRGWLLLQVS SRVFTEGEPL

ALRCHAWKDK LVYNVLYYRN GKAFKFFHWN SNLTILKTNI

SHNGTYHCSG MGKHRYTSAG ISVTVKELFP APVLNASVTS

PLLEGNLVTL SCETKLLLQR PGLQLYFSFY MGSKTLRGRN

TSSEYQILTA RREDSGLYWC EAATEDGNVL KRSPELELQV

LGLQLPTPVW FHVLFYLAVG IMFLVNTVLW VTIRKELKRK

KKWDLEISLD SGHEKKVISS LQEDRHLEEE LKCQEQKEEQ

LQEGVHRKEP QGAT rCD64#2 (pCDH-mutCD64) peptide sequence
                                    (SEQ ID NO: 10)
MWFLTTLLLW VPVDGQVDTT KAVITLQPPW VSVFQEETVT

LHCEVLHLPG SSSTQWFLNG TATQTSTPSY RITSASVNDS

GEYRCQRGLS GRSDPIQLEI HRGWLLLQVS SRVFTEGEPL

ALRCHAWKDK LVYNVLYYRN GKAFKFFHWN SNLTILKTNI

SHNGTYHCSG MGKHRYTSAG ISVTVKELFP APVLNASVTS

PLLEGNLVTL SCETKLLLQR PGLQLYFSFY MGSKTLRGRN

TSSEYQILTA RREDSGLYWC EAATEDGNVL KRSPELELQV

LGLQLPTPVW FHVLFYLAVG IMFLVNTVLW VTIRKELKRK

KKWNLEISLD SGHEKKVISS LQEDRHLEEE LKCQEQKEEQ

LQEGVHRKEP QGAT rCD64#3 (pCDH-CD64/16) peptide sequence
                                    (SEQ ID NO: 11)
MWFLTTLLLW VPVDGQVDTT KAVITLQPPW VSVFQEETVT

LHCEVLHLPG SSSTQWFLNG TATQTSTPSY RITSASVNDS

GEYRCQRGLS GRSDPIQLEI HRGWLLLQVS SRVFTEGEPL

ALRCHAWKDK LVYNVLYYRN GKAFKFFHWN SNLTILKTNI

SHNGTYHCSG MGKHRYTSAG ISVTVKELFP APVLNASVTS

PLLEGNLVTL SCETKLLLQR PGLQLYFSFY MGSKTLRGRN

TSSEYQILTA RREDSGLYWC EAATEDGNVL KRSPELELQV

LGFFPPGYQV SFCLVMVLLF AVDTGLYFSV KTNIRSSTRD

WKDHKFKWRK DPQDK rCD64#4 (pCDH-CD64/16-28-BB-Z) peptide sequence
                                    (SEQ ID NO: 12)
MWFLTTLLLW VPVDGQVDTT KAVISLQPPW VSVFQEETVT

LHCEVLHLPG SSSTQWFLNG TATQTSTPSY RITSASVNDS

GEYRCQRGLS GRSDPIQLEI HRGWLLLQVS SRVFTEGEPL

ALRCHAWKDK LVYNVLYYRN GKAFKFFHWN SNLTILKTNI

SHNGTYHCSG MGKHRYTSAG ISVTVKELFP APVLNASVTS

PLLEGNLVTL SCETKLLLQR PGLQLYFSFY MGSKTLRGRN

TSSEYQILTA RREDSGLYWC EAATEDGNVL KRSPELELQV

-continued

LGFFPPGYQV SFCLVMVLLF AVDTGLYFSV KTNIRSSTRD

WKDHKFKWRK DPQDKRSKRS RLLHSDYMNM TPRRPGPTRK

HYQPYAPPRD FAAYRSKRGR KKLLYIFKQP FMRPVQTTQE

EDGCSCRFPE EEEGGCELRV KFSRSADAPA YQQGQNQLYN

ELNLGRREEY DVLDKRRGRD PEMGGKPRRK NPQEGLYNEL

QKDKMAEAYS EIGMKGERRR GKGHDGLYQG LSTATKDTYD

ALHMQALPPR rCD64#5 (pCDH-CD64/16-28-BB-G) peptide sequence
                                    (SEQ ID NO: 13)
MWFLTTLLLW VPVDGQVDTT KAVITLQPPW VSVFQEETVT

LHCEVLHLPG SSSTQWFLNG TATQTSTPSY RITSASVNDS

GEYRCQRGLS GRSDPIQLEI HRGWLLLQVS SRVFTEGEPL

ALRCHAWKDK LVYNVLYYRN GKAFKFFHWN SNLTILKTNI

SHNGTYHCSG MGKHRYTSAG ISVTVKELFP APVLNASVTS

PLLEGNLVTL SCETKLLLQR PGLQLYFSFY MGSKTLRGRN

TSSEYQILTA RREDSGLYWC EAATEDGNVL KRSPELELQV

LGFFPPGYQV SFCLVMVLLF AVDTGLYFSV KTNIRSSTRD

WKDHKFKWRK DPQDKRSKRS RLLHSDYMNM TPRRPGPTRK

HYQPYAPPRD FAAYRSKRGR KKLLYIFKQP FMRPVQTTQE

EDGCSCRFPE EEEGGCELRL KIQVRKAAIT SYEKSDGVYT

GLSTRNQETY ETLKHEKPPQ rCD64#6 (pCDH-CD64/16-28-BB-D10) peptide sequence
                                    (SEQ ID NO: 14)
MWFLTTLLLW VPVDGQVDTT KAVITLQPPW VSVFQEETVT

LHCEVLHLPG SSSTQWFLNG TATQTSTPSY RITSASVNDS

GEYRCQRGLS GRSDPIQLEI HRGWLLLQVS SRVFTEGEPL

ALRCHAWKDK LVYNVLYYRN GKAFKFFHWN SNLTILKTNI

SHNGTYHCSG MGKHRYTSAG ISVTVKELFP APVLNASVTS

PLLEGNLVTL SCETKLLLQR PGLQLYFSFY MGSKTLRGRN

TSSEYQILTA RREDSGLYWC EAATEDGNVL KRSPELELQV

LGFFPPGYQV SFCLVMVLLF AVDTGLYFSV KTNIRSSTRD

WKDHKFKWRK DPQDKRSKRS RLLHSDYMNM TPRRPGPTRK

HYQPYAPPRD FAAYRSKRGR KKLLYIFKQP FMRPVQTTQE

EDGCSCRFPE EEEGGCELAR PRRSPAQEDG KVYINMPGRG rCD64#7 (pCDH-CD64/16-28-BB-D12) peptide sequence
                                    (SEQ ID NO: 15)
MWFLTTLLLW VPVDGQVDTT KAVITLQPPW VSVFQEETVT

LHCEVLHLPG SSSTQWFLNG TATQTSTPSY RITSASVNDS

GEYRCQRGLS GRSDPIQLEI HRGWLLLQVS SRVFTEGEPL

ALRCHAWKDK LVYNVLYYRN GKAFKFFHWN SNLTILKTNI

SHNGTYHCSG MGKHRYTSAG ISVTVKELFP APVLNASVTS

PLLEGNLVTL SCETKLLLQR PGLQLYFSFY MGSKTLRGRN

TSSEYQILTA RREDSGLYWC EAATEDGNVL KRSPELELQV

LGFFPPGYQV SFCLVMVLLF AVDTGLYFSV KTNIRSSTRD

-continued

WKDHKFKWRK DPQDKRSKRS RLLHSDYMNM TPRRPGPTRK

HYQPYAPPRD FAAYRSKRGR KKLLYIFKQP FMRPVQTTQE

EDGCSCRFPE EEEGGCELGR LVPRGRGAAE AATRKQRITE

TESPYQELQG QRSDVYSDLN TQRPYYK rCD64#8 (pCDH-CD64-28-28-BB-Z) peptide sequence
(SEQ ID NO: 16)
MWFLTTLLLW VPVDGQVDTT KAVITLQPPW VSVFQEETVT

LHCEVLHLPG SSSTQWFLNG TATQTSTPSY RITSASVNDS

GEYRCQRGLS GRSDPIQLEI HRGWLLLQVS SRVFTEGEPL

ALRCHAWKDK LVYNVLYYRN GKAFKFFHWN SNLTILKTNI

SHNGTYHCSG MGKHRYTSAG ISVTVKELFP APVLNASVTS

PLLEGNLVTL SCETKLLLQR PGLQLYFSFY MGSKTLRGRN

TSSEYQILTA RREDSGLYWC EAATEDGNVL KRSPELELQV

LGLQLPTPFW VLVVVGGVLA CYSLLVTVAF IIFWVRSKRS

RLLHSDYMNM TPRRPGPTRK HYQPYAPPRD FAAYRSKRGR

KKLLYIFKQP FMRPVQTTQE EDGCSCRFPE EEEGGCELRV

KFSRSADAPA YQQGQNQLYN ELNLGRREEY DVLDKRRGRD

PEMGGKPRRK NPQEGLYNEL QKDKMAEAYS EIGMKGERRR

GKGHDGLYQG LSTATKDTYD ALHMQALPPR rCD64#9 (pCDH-CD64-FceR) peptide sequence
(SEQ ID NO: 17)
MWFLTTLLLW VPVDGQVDTT KAVITLQPPW VSVFQEETVT

LHCEVLHLPG SSSTQWFLNG TATQTSTPSY RITSASVNDS

GEYRCQRGLS GRSDPIQLEI HRGWLLLQVS SRVFTEGEPL

ALRCHAWKDK LVYNVLYYRN GKAFKFFHWN SNLTILKTNI

SHNGTYHCSG MGKHRYTSAG ISVTVKELFP APVLNASVTS

PLLEGNLVTL SCETKLLLQR PGLQLYFSFY MGSKTLRGRN

TSSEYQILTA RREDSGLYWC EAATEDGNVL KRSPELELQV

LGAPREKYWL QFFIPLLVVI LFAVDTGLFI STQQQVTFLL

KIKRTRKGFR LLNPHPKPNP KNN rCD64#10 (pCDH-CD64/16-PKC⁻) peptide sequence
(SEQ ID NO: 18)
MWFLTTLLLW VPVDGQVDTT KAVITLQPPW VSVFQEETVT

LHCEVLHLPG SSSTQWFLNG TATQTSTPSY RITSASVNDS

GEYRCQRGLS GRSDPIQLEI HRGWLLLQVS SRVFTEGEPL

ALRCHAWKDK LVYNVLYYRN GKAFKFFHWN SNLTILKTNI

SHNGTYHCSG MGKHRYTSAG ISVTVKELFP APVLNASVTS

PLLEGNLVTL SCETKLLLQR PGLQLYFSFY MGSKTLRGRN

TSSEYQILTA RREDSGLYWC EAATEDGNVL KRSPELELQV

LGFFPPGYQV SFCLVMVLLF AVDTGLYFSV KTNIRGAGRD

WKDHKFKWRK DPQDK

-continued rCD64#11 (pCDH-CD64-G2D-2B4-Z) peptide sequence
(SEQ ID NO: 19)
MWFLTTLLLW VPVDGQVDTT KAVITLQPPW VSVFQEETVT

LHCEVLHLPG SSSTQWFLNG TATQTSTPSY RITSASVNDS

GEYRCQRGLS GRSDPIQLEI HRGWLLLQVS SRVFTEGEPL

ALRCHAWKDK LVYNVLYYRN GKAFKFFHWN SNLTILKTNI

SHNGTYHCSG MGKHRYTSAG ISVTVKELFP APVLNASVTS

PLLEGNLVTL SCETKLLLQR PGLQLYFSFY MGSKTLRGRN

TSSEYQILTA RREDSGLYWC EAATEDGNVL KRSPELELQV

LGSNLFVASW IAVMIIFRIG MAVAIFCCFF FPSGGSGGGS

GWRRKRKEKQ SETSPKEFLT IYEDVKDLKT RRNHEQEQTF

PGGGSTIYSM IQSQSSAPTS QEPAYTLYSL IQPSRKSGSR

KRNHSPSFNS TIYEVIGKSQ PKAQNPARLS RKELENFDVY

SGGSGGGSGR VKFSRSADAP AYKQGQNQLY NELNLGRREE

YDVLDKRRGR DPEMGGKPRR KNPQEGLYNE LQKDKMAEAY

SEIGMKGERR RGKGHDGLYQ GLSTATKDTY DALHMQALPP

R rCD64#12 (pCDH-CD64/16-2B4-Z) peptide sequence
(SEQ ID NO: 20)
MWFLTTLLLW VPVDGQVDTT KAVITLQPPW VSVFQEETVT

LHCEVLHLPG SSSTQWFLNG TATQTSTPSY RITSASVNDS

GEYRCQRGLS GRSDPIQLEI HRGWLLLQVS SRVFTEGEPL

ALRCHAWKDK LVYNVLYYRN GKAFKFFHWN SNLTILKTNI

SHNGTYHCSG MGKHRYTSAG ISVTVKELFP APVLNASVTS

PLLEGNLVTL SCETKLLLQR PGLQLYFSFY MGSKTLRGRN

TSSEYQILTA RREDSGLYWC EAATEDGNVL KRSPELELQV

LGFFPPGYQV SFCLVMVLLF AVDTGLYFSV KTNIRSSTRD

WKDHKFKWRK DPQDKWRRKR KEKQSETSPK EFLTIYEDVK

DLKTRRNHEQ EQTFPGGGST IYSMIQSQSS APTSQEPAYT

LYSLIQPSRK SGSRKRNHSP SFNSTIYEVI GKSQPKAQNP

ARLSRKELEN FDVYSGGSGG GSGRVKFSRS ADAPAYKQGQ

NQLYNELNLG RREEYDVLDK RRGRDPEMGG KPRRKNPQEG

LYNELQKDKM AEAYSEIGMK GERRRGKGHD GLYQGLSTAT

KDTYDALHMQ ALPPR rCD64#13 (pCDH-CD64/16-2B4-G) peptide sequence
(SEQ ID NO: 21)
MWFLTTLLLW VPVDGQVDTT KAVITLQPPW VSVFQEETVT

LHCEVLHLPG SSSTQWFLNG TATQTSTPSY RITSASVNDS

GEYRCQRGLS GRSDPIQLEI HRGWLLLQVS SRVFTEGEPL

ALRCHAWKDK LVYNVLYYRN GKAFKFFHWN SNLTILKTNI

SHNGTYHCSG MGKHRYTSAG ISVTVKELFP APVLNASVTS

PLLEGNLVTL SCETKLLLQR PGLQLYFSFY MGSKTLRGRN

TSSEYQILTA RREDSGLYWC EAATEDGNVL KRSPELELQV

```
LGFFPPGYQV SFCLVMVLLF AVDTGLYFSV KTNIRSSTRD

WKDHKFKWRK DPQDKWRRKR KEKQSETSPK EFLTIYEDVK

DLKTRRNHEQ EQTFPGGGST IYSMIQSQSS APTSQEPAYT

LYSLIQPSRK SGSRKRNHSP SFNSTIYEVI GKSQPKAQNP

ARLSRKELEN FDVYSGGSGG GSGRLKIQVR KAAITSYEKS

DGVYTGLSTR NQETYETLKH EKPPQ
``` rCD64#14 (pCDH-CD64/16-2B4-D10) peptide sequence
(SEQ ID NO: 22)
```
MWFLTTLLLW VPVDGQVDTT KAVITLQPPW VSVFQEETVT

LHCEVLHLPG SSSTQWFLNG TATQTSTPSY RITSASVNDS

GEYRCQRGLS GRSDPIQLEI HRGWLLLQVS SRVFTEGEPL

ALRCHAWKDK LVYNVLYYRN GKAFKFFHWN SNLTILKTNI

SHNGTYHCSG MGKHRYTSAG ISVTVKELFP APVLNASVTS

PLLEGNLVTL SCETKLLLQR PGLQLYFSFY MGSKTLRGRN

TSSEYQILTA RREDSGLYWC EAATEDGNVL KRSPELELQV

LGFFPPGYQV SFCLVMVLLF AVDTGLYFSV KTNIRSSTRD

WKDHKFKWRK DPQDKWRRKR KEKQSETSPK EFLTIYEDVK

DLKTRRNHEQ EQTFPGGGST IYSMIQSQSS APTSQEPAYT

LYSLIQPSRK SGSRKRNHSP SFNSTIYEVI GKSQPKAQNP

ARLSRKELEN FDVYSGGSGG GSGARPRRSP AQEDGKVYIN

MPGRG
``` rCD64#15 (pCDH-CD64/16-2B4-D12) peptide sequence
(SEQ ID NO: 23)
```
MWFLTTLLLW VPVDGQVDTT KAVITLQPPW VSVFQEETVT

LHCEVLHLPG SSSTQWFLNG TATQTSTPSY RITSASVNDS

GEYRCQRGLS GRSDPIQLEI HRGWLLLQVS SRVFTEGEPL

ALRCHAWKDK LVYNVLYYRN GKAFKFFHWN SNLTILKTNI

SHNGTYHCSG MGKHRYTSAG ISVTVKELFP APVLNASVTS

PLLEGNLVTL SCETKLLLQR PGLQLYFSFY MGSKTLRGRN

TSSEYQILTA RREDSGLYWC EAATEDGNVL KRSPELELQV

LGFFPPGYQV SFCLVMVLLF AVDTGLYFSV KTNIRSSTRD

DPQDKWRRKR KEKQSETSPK WKDHKFKWRK EFLTIYEDVK

DLKTRRNHEQ EQTFPGGGST IYSMIQSQSS APTSQEPAYT

LYSLIQPSRK SGSRKRNHSP SFNSTIYEVI GKSQPKAQNP

ARLSRKELEN FDVYSGGSGG GSGGRLVPRG RGAAEAATRK

QRITETESPY QELQGQRSDV YSDLNTQRPY YK
``` rCD64#16 (pCDH-CD64-64-2B4-Z) peptide sequence
(SEQ ID NO: 24)
```
MWFLTTLLLW VPVDGQVDTT KAVITLQPPW VSVFQEETVT

LHCEVLHLPG SSSTQWFLNG TATQTSTPSY RITSASVNDS

GEYRCQRGLS GRSDPIQLEI HRGWLLLQVS SRVFTEGEPL

ALRCHAWKDK LVYNVLYYRN GKAFKFFHWN SNLTILKTNI

SHNGTYHCSG MGKHRYTSAG ISVTVKELFP APVLNASVTS

PLLEGNLVTL SCETKLLLQR PGLQLYFSFY MGSKTLRGRN
```

```
TSSEYQILTA RREDSGLYWC EAATEDGNVL KRSPELELQV

LGLQLPTPVW FHVLFYLAVG IMFLVNTVLW VTIRKELKRK

KKWDLEISLD SGHEKKVISS LQEDRHLEEE LKCQEQKEEQ

LQEGVHRKEP QGATGWRRKR KEKQSETSPK EFLTIYEDVK

DLKTRRNHEQ EQTFPGGGST IYSMIQSQSS APTSQEPAYT

LYSLIQPSRK SGSRKRNHSP SFNSTIYEVI GKSQPKAQNP

ARLSRKELEN FDVYSGGSGG GSGRVKFSRS ADAPAYKQGQ

NQLYNELNLG RREEYDVLDK RRGRDPEMGG KPRRKNPQEG

LYNELQKDKM AEAYSEIGMK GERRRGKGHD GLYQGLSTAT

KDTYDALHMQ ALPPR
```

Canine CD16#17 (pCDH-caCD16) peptide sequence
(SEQ ID NO: 25)
```
MWQLVSSTAL LLLVSAGTQA DVPKAVVVLE PKWNRVLTMD

SVTLKCQGDH LLRDNYTWLH NGRPISNQIS TYIIKNASIK

NSGEYRCQTD QSKLSDPVQL EVHTGWLLLQ VPRLVFQEGE

LIQLKCHSWK NTPVRNVQYF QNGRGKKFFY NNSEYHIPAA

TSEHNGSYFC RGIIGKKNES SEAVNIIIQG SSLPSTSLLL

SHWPQIPFSL VMALLFAVDT GLYFAVQRDL RSSMGNLKNS

KVIWSQGS
```

Canine CD64#18 (pCDH-caCD64) peptide sequence
(SEQ ID NO: 26)
```
MWLLTVLLLW VPAGAQTDPV KAVITLQPPW VSVFQEESVT

LWCEGPHLPG DSSTQWFLNG TATQTLTPRY RIAAASVNDN

GEYRCQTGLS VLSDPIQLGI HRDWLILQVS GRVFTEGEPL

TLRCHGWNNK LVYNVLFYQN GTVLKFSPQN SEFTILKTTL

HHNGIYHCSA MGKHRYESAG VSITIKELFP APVLKASLSS

PILEGHVVNL SCETKLLLQR PGLQLYFSFY MGSKTLLSRN

TSSEYQILTA KKEDSGLYWC EATTEDGNVV KRSPELELQV

VGPQTLTPVW FHVLFYVAMG MIFLVDTIFC MIIHKELQRK

KKWNLEISLY SGLEKRVDSY LQKERDLEEP KYQELEQLQE

KTPQKPPEGE QQ
```

Canine CD64sp#19 (pCDH-caCD64sp) peptide
sequence
(SEQ ID NO: 27)
```
MWLLTVLLLW VPAGAQTDWL ILQVSGRVFT EGEPLTLRCH

GWNNKLVYNV LFYQNGTVLK FSPQNSEFTI LKTTLHHNGI

YHCSAMGKHR YESAGVSITI KELFPAPVLK ASLSSPILEG

HVVNLSCETK LLLQRPGLQL YFSFYMGSKT LLSRNTSSEY

QILTAKKEDS GLYWCEATTE DGNVVKRSPE LELQVVGPQT

LTPVWFHVLF YVAMGMIFLV DTIFCMIIHK ELQRKKKWNL

EISLYSGLEK RVDSYLQKER DLEEPKYQEL EQLQEKTPQK

PPEGEQQ
```

What is claimed is:

1. A method of treating a subject having a tumor, wherein said method comprises: administering, to said subject, recombinant immune cells preloaded with an IgG antibody that specifically binds to cells of said tumor, wherein said recombinant immune cells comprise a chimeric IgG Fc receptor comprising:

(i) an extracellular domain comprising a CD64 extracellular domain that binds to an IgG Fc region of said IgG antibody;

(ii) a transmembrane domain; and (iii) an intracellular domain of CD16A comprising an Fc receptor immunoreceptor tyrosine-based activation motif (ITAM), and wherein said recombinant immune cells kill cells of said tumor within said subject.

2. The method of claim 1, wherein said subject is a human.

3. The method of claim 1, wherein said CD64 extracellular domain and said intracellular domain of CD16A are derived from a canine species.

4. The method of claim 1, wherein said recombinant immune cells are NK cells.

5. The method of claim 4, wherein said NK cells are NK cells derived from induced pluripotent stem cells.

6. The method of claim 1, wherein said recombinant immune cells are T cells.

7. The method of claim 6, wherein said T cells are T cells derived from induced pluripotent stem cells.

8. The method of claim 1, wherein said intracellular domain comprises a signaling domain.

9. The method of claim 8, wherein the signaling domain comprises a signaling domain of CD27, CD28, CD134 (OX40), CD137 (4-1 BB), FcεR1, NKG2D, CD244 (2B4), FcRγ, DAP10, DAP12, or CD35.

* * * * *